United States Patent
Kim et al.

(10) Patent No.: US 7,989,472 B2
(45) Date of Patent: Aug. 2, 2011

(54) GLUCAGON RECEPTOR ANTAGONIST COMPOUNDS, COMPOSITIONS CONTAINING SUCH COMPOUNDS AND METHODS OF USE

(75) Inventors: Ronald M. Kim, Summit, NJ (US); Emma R. Parmee, Scotch Plains, NJ (US); Qiang Tan, Westfield, NJ (US); Ashley Rouse Lins, Edison, NJ (US); Jiang Chang, Westfield, NJ (US); Cangming Yang, Highland Park, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 382 days.

(21) Appl. No.: 12/225,056

(22) PCT Filed: Mar. 19, 2007

(86) PCT No.: PCT/US2007/006806
§ 371 (c)(1),
(2), (4) Date: Sep. 12, 2008

(87) PCT Pub. No.: WO2007/111864
PCT Pub. Date: Oct. 4, 2007

(65) Prior Publication Data
US 2009/0209564 A1    Aug. 20, 2009

Related U.S. Application Data

(60) Provisional application No. 60/785,011, filed on Mar. 23, 2006.

(51) Int. Cl.
*A61K 31/47* (2006.01)
*A61K 31/4184* (2006.01)
*C07D 215/00* (2006.01)
*C07D 235/04* (2006.01)

(52) U.S. Cl. ........ 514/311; 546/112; 546/152; 546/174; 546/175; 548/302.7; 548/309.7; 548/469; 548/510; 548/217; 514/299; 514/385; 514/394

(58) Field of Classification Search .................. 546/112, 546/152, 174, 175; 548/301.7, 302.7, 304.4, 548/309.7, 469, 510, 215, 217; 514/299, 514/311, 385, 394
See application file for complete search history.

(56) References Cited

U.S. PATENT DOCUMENTS

| 5,776,954 | A | 7/1998 | de Laszlo et al. | |
|---|---|---|---|---|
| 7,151,114 | B2 | 12/2006 | Streicher et al. | |
| 7,687,534 | B2 * | 3/2010 | Stelmach et al. | 514/415 |
| 7,803,951 | B2 * | 9/2010 | Liang et al. | 548/251 |
| 2008/0161347 | A1 | 7/2008 | Stelmach et al. | |

FOREIGN PATENT DOCUMENTS

| EP | 1 489 077 | 12/2004 |
|---|---|---|
| WO | WO 97/16442 | 5/1997 |
| WO | WO 98/04528 | 2/1998 |
| WO | WO 98/21957 | 5/1998 |
| WO | WO 98/22108 | 5/1998 |
| WO | WO 98/22109 | 5/1998 |
| WO | WO 99/01423 | 1/1999 |
| WO | WO 99/32448 | 7/1999 |
| WO | WO 00/39088 | 7/2000 |
| WO | WO 00/69810 | 11/2000 |
| WO | WO 02/00612 | 1/2002 |
| WO | WO 02/40444 | 5/2002 |
| WO | WO 03/048109 | 6/2003 |
| WO | WO 03/051357 | 6/2003 |
| WO | WO 03/053938 | 7/2003 |
| WO | WO 03/064404 | 8/2003 |
| WO | WO 03/097619 | 11/2003 |
| WO | WO 2004/002480 | 1/2004 |
| WO | WO 2004/050039 | 6/2004 |
| WO | WO 2004/056763 | 7/2004 |
| WO | WO 2004/062663 | 7/2004 |
| WO | WO 2004/069158 | 8/2004 |
| WO | WO 2005/058845 | 6/2005 |

OTHER PUBLICATIONS

C. A. Hunter, Chemical Comm., vol. 14, pp. 1642-1643 (2003), "New building blocks for the assembly of sequence selective molecular zippers".
Chemical Abstracts, vol. 83, Abstract No. 131960, Vinogradova, S. V. "Synthesis of new derivatives of fluorene", Isvestiya Akademii Nauk SSSR, Seriya Kimicheskaya, 1975, 1, 191-192.
Chemical Abstracts, vol. 90, Abstract No. 72485, Vinogradova, S.V., "Fluorene-containing cardopoly amides", Faserforschung and Textiltechnik, 1978, 29(10), 613-615.

* cited by examiner

*Primary Examiner* — Golam M Shameem
(74) *Attorney, Agent, or Firm* — Heidi M. Struse; Richard C. Billups

(57) ABSTRACT

Glucagon receptor antagonist compounds are disclosed. The compounds are useful for treating type 2 diabetes and related conditions. Pharmaceutical compositions and methods of treatment are also included.

18 Claims, No Drawings

GLUCAGON RECEPTOR ANTAGONIST COMPOUNDS, COMPOSITIONS CONTAINING SUCH COMPOUNDS AND METHODS OF USE

CROSS-REFERENCE TO RELATED APPLICATIONS

This application is a U.S. National Phase application under 35 U.S.C. §371 of PCT Application No. PCT/US2007/006806, filed Mar. 19, 2007, which published as WO 2007/111864 on Oct. 4, 2007, and claims priority under 35 U.S.C. §119 from U.S. Provisional Application No. 60/785,011, filed Mar. 23, 2006.

BACKGROUND OF THE INVENTION

The present invention relates to glucagon receptor antagonist compounds, compositions containing such compounds and various methods of treatment relating to type 2 diabetes mellitus and related conditions.

Diabetes refers to a disease process derived from multiple causative factors and is characterized by elevated levels of plasma glucose (hyperglycemia) in the fasting state or following glucose administration during an oral glucose tolerance test. Frank diabetes mellitus (e.g., a blood glucose level>126 mg/dL in a fasting state) is associated with increased and premature cardiovascular morbidity and mortality, and is related directly and indirectly to various metabolic conditions, including alterations of lipid, lipoprotein and apolipoprotein metabolism.

Patients with non-insulin dependent diabetes mellitus (type 2 diabetes mellitus), approximately 95% of patients with diabetes mellitus, frequently display elevated levels of serum lipids, such as cholesterol and triglycerides, and have poor blood-lipid profiles, with high levels of LDL-cholesterol and low levels of HDL-cholesterol. Those suffering from Type 2 diabetes mellitus are thus at an increased risk of developing macrovascular and microvascular complications, including coronary heart disease, stroke, peripheral vascular disease, hypertension (for example, blood pressure>130/80 mmHg in a resting state), nephropathy, neuropathy and retinopathy.

Patients having type 2 diabetes mellitus characteristically exhibit elevated plasma insulin levels compared with nondiabetic patients; these patients have developed a resistance to insulin stimulation of glucose and lipid metabolism in the main insulin-sensitive tissues (muscle, liver and adipose tissues). Thus, Type 2 diabetes, at least early in the natural progression of the disease is characterized primarily by insulin resistance rather than by a decrease in insulin production, resulting in insufficient uptake, oxidation and storage of glucose in muscle, inadequate repression of lipolysis in adipose tissue, and excess glucose production and secretion by the liver. The net effect of decreased sensitivity to insulin is high levels of insulin circulating in the blood without appropriate reduction in plasma glucose (hyperglycemia). Hyperinsulinemia is a risk factor for developing hypertension and may also contribute to vascular disease.

Glucagon serves as the major regulatory hormone attenuating the effect of insulin in its inhibition of liver gluconeogenesis and is normally secreted by alpha cells in pancreatic islets in response to falling blood glucose levels. The hormone binds to specific receptors in liver cells that triggers glycogenolysis and an increase in gluconeogenesis through cAMP-mediated events. These responses generate glucose (e.g. hepatic glucose production) to help maintain euglycemia by preventing blood glucose levels from falling significantly. In addition to elevated levels of circulating insulin, type 2 diabetics have elevated levels of plasma glucagon and increased rates of hepatic glucose production. Antagonists of the glucagon receptor are useful in improving insulin responsiveness in the liver, decreasing the rate of gluconeogenesis and glycogenolysis, and lowering the rate of hepatic glucose output resulting in a decrease in the levels of plasma glucose.

SUMMARY OF THE INVENTION

The present invention is directed to a compound represented by formula I:

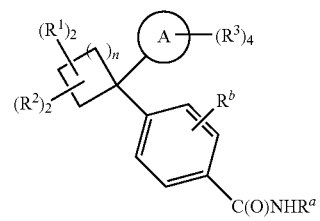

or a pharmaceutically acceptable salt or solvate thereof, wherein:

Ring A represents a 6-10 membered Aryl group or a 5-10 membered heteroaryl or partially aromatic heterocyclic group containing 1-4 heteroatoms, 0-4 of which are N atoms, and 0-1 of which are O or S atoms;

two $R^1$ and two $R^2$ groups are present and represent hydrogen, or one or two $R^1$ and $R^2$ groups are selected from (a), (b) and (c) below:

(a) halo, OH, $CO_2R^4$, $SO_pR^5$, CN, $NO_2C(O)NR^6R^7$ or $NR^6R^7$;

(b) $C_{1-10}$alkyl, $C(O)C_{1-10}$alkyl, $OC_{1-6}$alkyl, $C_{2-6}$alkenyl, the alkyl portions being optionally substituted with: (1) 1-5 halo groups, up to perhalo, and 1-2 OH groups;

(c) a 6-10 membered Aryl, O-Aryl or S-Aryl group, or a 5-10 membered HAR, O-HAR or S-HAR group containing 0-4 nitrogen and 0-1 O or S atoms, said group being optionally substituted with 1-3 groups selected from (a) and (b) above, or two $R^2$ groups can be taken together in combination and represent a methylene or ethylene bridge forming a carbocyclic ring containing 5 or 6 atoms, or a fused phenyl ring optionally substituted with 1-3 halo groups and 1-2 CN, $SO_pR^5$, $C_{1-3}$alkyl, $C_{1-3}$alkoxy, halo$C_{1-3}$ alkyl, halo$C_{1-3}$ alkoxy groups, and the $R^1$ groups represent H or are selected from (a) through (c) above;

four $R^3$ groups are present as follows:

1) 0-1 $R^3$ group is selected from the group consisting of: Aryl, HAR, —$(CH_2)_{1-4}$Aryl, —$(CH_2)_{1-4}$HAR, —X-Aryl, —X-HAR, —X—$C_{1-4}$-Aryl and —X—$C_{1-4}$Alkyl-HAR; wherein X represents O, S, S(O) or $S(O)_2$;

said Aryl and HAR groups and portions of the groups above being optionally substituted with 1-4 halo atoms, and 1-2 members selected from: OH, CN, $C_{1-6}$alkyl, $OC_{1-6}$alkyl, halo$C_{1-6}$alkyl, $OC_{1-6}$haloalkyl, $NO_2$, $SO_pR^5$, $C_{2-6}$alkenyl, $OC_{2-6}$alkenyl, $NR^6R^7$ and HAR;

2) 0-3 $R^3$ groups are selected from: OH, CN, oxo, $NO_2$, $SO_pR^5$, $NR^6R^7$, $C_{1-10}$alkyl, halo$C_{1-10}$alkyl, $OC_{1-10}$alkyl, $OC_{1-10}$haloalkyl, $C_{2-10}$alkenyl, $OC_{2-6}$alkenyl and halo$C_{2-4}$alkenyl, and 3) the remaining $R^3$ groups are H or halo atoms;

$R^4$ is H or $C_{1-6}$alkyl, and $R^5$ represents a member selected from the group consisting of: $C_{1-10}$alkyl, Aryl or Ar—$C_{1-4}$alkyl;

$R^6$ and $R^7$ each independently represent H or $C_{1-6}$alkyl;

n represents an integer of from 0-5;
p is 0, 1 or 2;
$R^a$ represents $CH_2CH_2CO_2R^4$, $CH_2CH(OH)CO_2R^4$ or 5-tetrazolyl; and
$R^b$ is H or is selected from the group consisting of: halo, CN, $NO_2$, OH, $C_{1-3}$alkyl, $OC_{1-3}$alkyl, halo$C_{1-3}$alkyl and halo$C_{1-3}$alkoxy.

DETAILED DESCRIPTION OF THE INVENTION

The invention is described herein in detail using the terms defined below unless otherwise specified.

"Alkyl", as well as other groups having the prefix "alk", such as alkoxy, alkanoyl and the like, means carbon chains which may be linear, branched, or cyclic, or combinations thereof, containing the indicated number of carbon atoms. If no number is specified, 1-10 carbon atoms are intended for linear or branched alkyl groups. Examples of alkyl groups include methyl, ethyl, propyl, isopropyl, butyl, sec- and tert-butyl, pentyl, hexyl, heptyl, octyl, nonyl and the like. Cycloalkyl is a subset of alkyl; if no number of atoms is specified, 3-10 carbon atoms are intended, forming 1-3 carbocyclic rings that are fused. Examples of cycloalkyl include cyclopropyl, cyclobutyl, cyclopentyl, cyclohexyl, cycloheptyl, decahydronaphthyl and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Aryl" (Ar) means mono- and bicyclic aromatic rings containing 6-12 carbon atoms. Examples of aryl include phenyl, naphthyl, indenyl and the like. "Aryl" also includes monocyclic rings fused to an aryl group. Examples include tetrahydronaphthyl, indanyl and the like.

"Heteroaryl" (HAR) means a mono- or bicyclic aromatic ring or ring system containing at least one heteroatom selected from O, S and N, with each ring containing 5 to 6 atoms. Examples include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl and the like. Heteroaryl also includes aromatic heterocyclic groups fused to heterocycles that are non-aromatic or partially aromatic, and aromatic heterocyclic groups fused to cycloalkyl rings. Heteroaryl also includes such groups in charged form, e.g., pyridinium.

"Heterocyclyl" (Hetcy) means mono- and bicyclic saturated rings and ring systems containing at least one heteroatom selected from N, S and O, each of said ring having from 3 to 10 atoms in which the point of attachment may be carbon or nitrogen. Examples of "heterocyclyl" include pyrrolidinyl, piperidinyl, piperazinyl, imidazolidinyl, 2,3-dihydrofuro(2, 3-b)pyridyl, benzoxazinyl, tetrahydrohydroquinolinyl, tetrahydroisoquinolinyl, dihydroindolyl, and the like The term also includes partially unsaturated monocyclic rings that are not aromatic, such as 2- or 4-pyridones attached through the nitrogen or N-substituted-(1H, 3H)-pyrimidine-2,4-diones (N-substituted uracils). Heterocyclyl moreover includes such moieties in charged form, e.g., piperidinium.

"Halogen" (Halo) includes fluorine, chlorine, bromine and iodine.

One aspect of the present invention is directed to a compound represented by formula I:

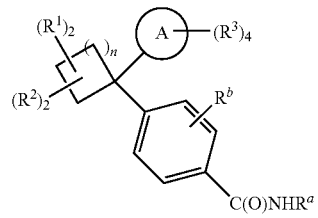

or a pharmaceutically acceptable salt or solvate thereof, wherein:

Ring A represents a 6-10 membered Aryl group or a 5-10 membered heteroaryl or partially aromatic heterocyclic group containing 1-4 heteroatoms, 0-4 of which are N atoms, and 0-1 of which are O or S atoms;

two $R^1$ and two $R^2$ groups are present and represent hydrogen, or one or two $R^1$ and $R^2$ groups are selected from (a), (b) and (c) below:

(a) halo, OH, $CO_2R^4$, $SO_pR^5$, CN, $NO_2C(O)NR^6R^7$ or $NR^6R^7$;

(b) $C_{1-10}$alkyl, $C(O)C_{1-10}$alkyl, $OC_{1-6}$alkyl, $C_{2-6}$alkenyl, the alkyl portions being optionally substituted with: (1) 1-5 halo groups, up to perhalo, and 1-2 OH groups;

(c) a 6-10 membered Aryl, O-Aryl or S-Aryl group, or a 5-10 membered HAR, O-HAR or S-HAR group containing 0-4 nitrogen and 0-1 O or S atoms, said group being optionally substituted with 1-3 groups selected from (a) and (b) above, or two $R^2$ groups can be taken together in combination and represent a methylene or ethylene bridge forming a carbocyclic ring containing 5 or 6 atoms, or a fused phenyl ring optionally substituted with 1-3 halo groups and 1-2 CN, $SO_pR^5$, $C_{1-3}$alkyl, $C_{1-3}$ alkoxy, halo$C_{1-3}$ alkyl, halo$C_{1-3}$ alkoxy groups, and the $R^1$ groups represent H or are selected from (a) through (c) above;

four $R^3$ groups are present as follows:

2) 0-1 $R^3$ group is selected from the group consisting of: Aryl, HAR, —$(CH_2)_{1-4}$Aryl, —$(CH_2)_{1-4}$HAR, —X-Aryl, —X-HAR, —X—$C_{1-4}$Alkyl-Aryl and —X—$C_{1-4}$Alkyl-HAR; wherein X represents O, S, S(O) or $S(O)_2$;

said Aryl and HAR groups and portions of the groups above being optionally substituted with 1-4 halo atoms, and 1-2 members selected from: OH, CN, $C_{1-6}$alkyl, $OC_{1-6}$alkyl, halo$C_{1-6}$alkyl, $OC_{1-6}$haloalkyl, $NO_2$, $SO_pR^5$, $C_{2-6}$alkenyl, $OC_{2-6}$alkenyl, $NR^6R^7$ and HAR;

2) 0-3 $R^3$ groups are selected from: OH, CN, oxo, $NO_2$, $SO_pR^5$, $NR^6R^7$, $C_{1-10}$alkyl, halo$C_{1-10}$alkyl, $OC_{1-10}$ alkyl, $OC_{1-10}$haloalkyl, $C_{2-10}$alkenyl, $OC_{2-6}$alkenyl and halo$C_{2-4}$alkenyl, and 3) the remaining $R^3$ groups are H or halo atoms;

$R^4$ is H or $C_{1-6}$alkyl, and $R^5$ represents a member selected from the group consisting of: $C_{1-10}$alkyl, Aryl or Ar—$C_{1-4}$alkyl;

$R^6$ and $R^7$ each independently represent H or $C_{1-6}$alkyl;

n represents an integer of from 0-5;

p is 0, 1 or 2;

$R^a$ represents $CH_2CH_2CO_2R^4$, $CH_2CH(OH)CO_2R^4$ or 5-tetrazolyl; and

R$^b$ is H or is selected from the group consisting of: halo, CN, NO$_2$, OH, C$_{1-3}$alkyl, OC$_{1-3}$alkyl, haloC$_{1-3}$alkyl and haloC$_{1-3}$alkoxy.

Another aspect of the invention that is of interest relates to a compound represented by formula I or a pharmaceutically acceptable salt or solvate thereof wherein Ring A represents an Aryl group selected from phenyl, naphthyl and tetrahydronaphthyl, a HAR group which is a 6-10 membered aromatic heteroaryl or partially aromatic heterocyclyl containing 1-2 heteroatoms, 0-1 of which is O and 0-2 of which are N atoms. Within this subset of the invention, all other variables are as originally defined with respect to formula I.

More particularly, another aspect of the invention that is of interest relates to a compound of formula I or a pharmaceutically acceptable salt or solvate thereof wherein Ring A represents a member selected from the group consisting of:

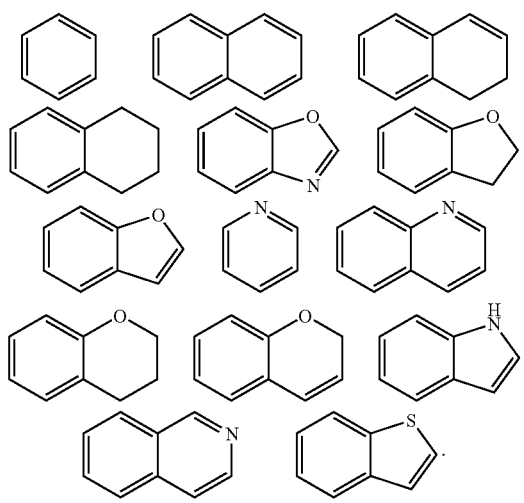

Within this subset of the invention, all other variables are as originally defined with respect to formula I.

Even more particularly, an aspect of the invention that is of interest relates to a compound of formula I or a pharmaceutically acceptable salt or solvate thereof wherein Ring A represents a member selected from the group consisting of:

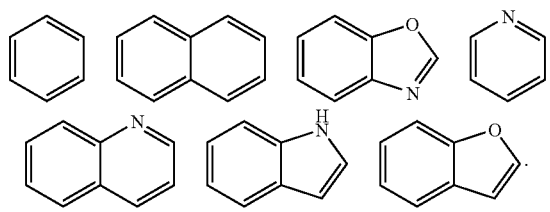

Within this subset of the invention, all other variables are as originally defined with respect to formula I.

Another aspect of the invention that is of interest relates to a compound represented by formula I or a pharmaceutically acceptable salt or solvate thereof wherein n represents an integer selected from 1, 2 and 3. Within this subset of the invention, all other variables are as originally defined with respect to formula I.

In particular, another aspect of the invention that is of interest relates to a compound represented by formula I or a pharmaceutically acceptable salt or solvate thereof wherein n represents an integer selected from 1 and 2. Within this subset of the invention, all other variables are as originally defined with respect to formula I.

More particularly, another aspect of the invention that is of interest relates to a compound represented by formula I or a pharmaceutically acceptable salt or solvate thereof wherein n represents 2. Within this subset of the invention, all other variables are as originally defined with respect to formula I.

Another aspect of the invention that is of interest relates to a compound represented by formula I or a pharmaceutically acceptable salt or solvate thereof wherein the R$^1$ and R$^2$ groups represent hydrogen or 1-2 of the R$^1$ and R$^2$ groups are independently selected from the group consisting of: halo; OH; C$_{1-6}$alkyl optionally substituted with 1-3 halo groups; CN; NR$^6$R$^7$; SO$_p$R$^5$; C$_{2-4}$alkenyl, and a 6-10 membered Aryl group, or the R$^2$ groups are taken in combination and represent a —CH$_2$— or —CH$_2$CH$_2$— group, or a fused phenyl ring, unsubstituted or substituted with 1-3 groups, up to 3 of which are halo groups, and up to 2 of which are C$_{1-3}$alkyl, haloC$_{1-3}$alkyl, C$_{1-3}$alkoxy or haloC$_{1-3}$alkoxy groups. Within this subset of the invention, all other variables are as originally defined with respect to formula I.

In particular, another aspect of the invention that is of interest relates to a compound represented by formula I or a pharmaceutically acceptable salt or solvate thereof wherein the R$^1$ groups represent hydrogen; halo; C$_{1-4}$alkyl optionally substituted with 1-3 halo groups; CN or NR$^6$R$^7$; and the R$^2$ groups represent H, or are taken in combination and represent a —CH$_2$— or a fused phenyl ring, unsubstituted or substituted with 1-3 groups, up to 3 of which are halo groups, and up to 2 of which are C$_{1-3}$alkyl, haloC$_{1-3}$alkyl, C$_{1-3}$alkoxy or haloC$_{1-3}$alkoxy groups. Within this subset of the invention, all other variables are as originally defined with respect to formula I.

Even more particularly, another aspect of the invention that is of interest relates to a compound represented by formula I or a pharmaceutically acceptable salt or solvate thereof wherein the R$^1$ groups represent hydrogen; halo; CH$_3$ or CF$_3$, and the R$^2$ groups represent H, or are taken in combination and represent a —CH$_2$— or a fused phenyl ring. Within this subset of the invention, all other variables are as originally defined with respect to formula I.

Another aspect of the invention that is of interest relates to compounds of formula I or a pharmaceutically acceptable salt or solvate thereof wherein R$^a$ is selected from

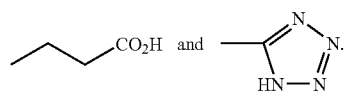

Within this subset of the invention, all other variables are as originally defined with respect to formula I More particularly, an aspect of the invention that is of interest relates to a compound of formula I or a pharmaceutically acceptable salt or solvate thereof wherein R$^a$ represents

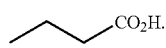

Within this subset of the invention, all other variables are as originally defined with respect to formula I Another aspect of the invention that is of interest relates to a compound of formula I or a pharmaceutically acceptable salt or solvate thereof wherein $R^b$ represents H. Within this subset of the invention, all other variables are as originally defined with respect to formula I Another aspect of the invention that is of interest relates to a compound of formula I or a pharmaceutically acceptable salt or solvate thereof wherein each $R^3$ is selected as follows:
1) 0-1 $R^3$ group is selected from the group consisting of: Aryl, HAR, —$CH_2$-Aryl, —$CH_2$-HAR, —O-Aryl, —O-HAR, —O—$CH_2$-Aryl and —O—$CH_2$-HAR;
   said Aryl and HAR groups and portions of the groups above being optionally substituted with 1-2 halo atoms, and 1-2 members selected from: CN, $C_{1-6}$alkyl, $OC_{1-6}$alkyl, halo$C_{1-3}$alkyl, $OC_{1-3}$haloalkyl, $NO_2$, $SO_pR^5$, $C_{2-6}$alkenyl, $NH_2$, $NMe_2$ and HAR;
2) 0-3 $R^3$ groups are selected from: CN, oxo, $NO_2$, $S(O)_p$$C_{1-8}$alkyl, $NH_2$, $NMe_2$, $C_{1-7}$alkyl, halo$C_{1-3}$alkyl, $OC_{1-7}$alkyl, $OC_{1-3}$haloalkyl and $C_{2-6}$alkenyl, and
3) the remaining $R^3$ groups are H or halo atoms. Within this subset of the invention, all other variables are as originally defined with respect to formula I.

More particularly, an aspect of the invention that is of interest relates to a compound of formula I or a pharmaceutically acceptable salt or solvate thereof wherein each $R^3$ is selected as follows:
1) 0-1 $R^3$ group is selected from the group consisting of: Aryl, HAR, —$CH_2$-Aryl, —$CH_2$-HAR, —O-Aryl, —O-HAR, —O—$CH_2$-Aryl and —O—$CH_2$-HAR;
   said Aryl and HAR groups and portions of the groups above being optionally substituted with 1-2 halo atoms and 1-2 members selected from: CN, $C_{1-4}$alkyl, $OC_{1-6}$alkyl, $S(O)pC_{1-6}$alkyl, halomethyl, halomethoxy, $NO_2$, $NMe_2$ and pyrazolyl;
2) 0-1 $R^3$ group is selected from: CN, oxo, $NO_2$, $SO_2CH_3$, $NMe_2$, $C_{1-7}$alkyl, halo$C_{1-3}$alkyl, $OC_{1-7}$alkyl, $OC_{1-3}$haloalkyl and $C_{2-6}$alkenyl, and
3) the remaining $R^3$ groups are H or halo atoms. Within this subset of the invention, all other variables are as originally defined with respect to formula I Even more particularly, an aspect of the invention that is of interest relates to a compound of formula I or a pharmaceutically acceptable salt or solvate thereof wherein each $R^3$ is selected as follows: each $R^3$ group is selected as follows:
1) 0-1 $R^3$ groups represents: Aryl, wherein Aryl is selected from phenyl, naphthyl and tetrahydronaphthyl; HAR selected from pyridyl, quinolinyl, pyrimidinyl, isoxazolyl, benzoxazolyl, benzopyrazolyl, benzooxadiazolyl, indazolyl, benzofuranyl, tetrahydroquinolinyl, benzothiophene, benzothiazole and benzoimidazolyl; —$CH_2$-Aryl selected from benzyl; —O-Aryl selected from phenyloxy; —O-HAR selected from pyridyloxy, benzothiazoloxy and quinolinyloxy; —O—$CH_2$-Aryl selected from benzyloxy or —O—$CH_2$-HAR selected from: pyridylmethoxy, furanylmethoxy, benzothiazolmethoxy and quinolinylmethoxy,
   said Aryl and HAR groups and portions of the groups above being optionally substituted with 1-2 halo atoms and 1 member selected from: CN, $C_{1-4}$alkyl, methoxy, trifluoromethyl, trifluoromethoxy, $NO_2$, and $NMe_2$;
2) 0-1 $R^3$ group is selected from: $C_{1-7}$alkyl, halo$C_{1-3}$alkyl, $OC_{1-7}$alkyl and $OC_{1-3}$haloalkyl, and
3) the remaining $R^3$ groups are H or halo atoms. Within this subset of the invention, all other variables are as originally defined with respect to formula I.

Another aspect of the invention that is of interest relates to a compound of formula I or a pharmaceutically acceptable salt or solvate thereof wherein:

Ring A represents an Aryl group selected from phenyl, naphthyl and tetrahydronaphthyl, a HAR group which is a 6-10 membered aromatic heteroaryl or partially aromatic heterocyclyl containing 1-2 heteroatoms, 0-1 of which is O and 0-2 of which are N atoms;

n represents an integer selected from 1, 2 and 3;

the $R^1$ and $R^2$ groups represent hydrogen or 1-2 of the $R^1$ and $R^2$ groups are independently selected from the group consisting of: halo; OH; $C_{1-6}$alkyl optionally substituted with 1-3 halo groups; CN; $NR^6R^7$; $SO_pR^5$; $C_{2-4}$alkenyl, and a 6-10 membered Aryl group, or the $R^2$ groups are taken in combination and represent a —$CH_2$— or —$CH_2CH_2$— group, or a fused phenyl ring, unsubstituted or substituted with 1-3 groups, up to 3 of which are halo groups, and up to 2 of which are $C_{1-3}$alkyl, halo$C_{1-3}$alkyl, $C_{1-3}$alkoxy or halo$C_{1-3}$alkoxy groups;

$R^a$ is selected from

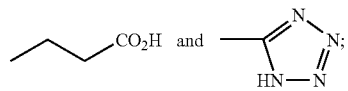

$R^b$ represents H, and each $R^3$ is selected as follows:
1) 0-1 $R^3$ group is selected from the group consisting of: Aryl, HAR, —$CH_2$-Aryl, —$CH_2$-HAR, —O-Aryl, —O-HAR, —O—$CH_2$-Aryl and —O—$CH_2$-HAR;
   said Aryl and HAR groups and portions of the groups above being optionally substituted with 1-2 halo atoms, and 1-2 members selected from: CN, $C_{1-6}$alkyl, $OC_{1-6}$alkyl, halo$C_{1-3}$alkyl, $OC_{1-3}$haloalkyl, $NO_2$, $SO_pR^5$, $C_{2-6}$alkenyl, $NH_2$, $NMe_2$ and HAR;
2) 0-3 $R^3$ groups are selected from: CN, oxo, $NO_2$, $S(O)_p$$C_{1-8}$alkyl, $NH_2$, $NMe_2$, $C_{1-7}$alkyl, halo$C_{1-3}$alkyl, $OC_{1-7}$alkyl, $OC_{1-3}$haloalkyl and $C_{2-6}$alkenyl, and
3) the remaining $R^3$ groups are H or halo atoms.

Within this subset of the invention, all other variables are as originally defined with respect to formula I.

Examples of compounds that fall within the invention described herein are in the tables described herein. Pharmaceutically acceptable salts and solvates of the compounds disclosed in the tables are included as well.

Another aspect of the invention that is of interest relates to a pharmaceutical composition comprising a compound as described above with respect to formula I in combination with a pharmaceutically acceptable carrier.

Another aspect of the invention that is of interest relates to a method of treating type 2 diabetes mellitus in a mammalian patient in need of such treatment comprising administering to said patient a compound as described above with respect to formula I in an amount that is effective to treat type 2 diabetes mellitus.

Another aspect of the invention that is of interest relates to a method of delaying the onset of type 2 diabetes mellitus in a mammalian patient in need thereof, comprising administering to the patient a compound as described above in accordance with formula I in an amount that is effective to delay the onset of type 2 diabetes mellitus.

Another aspect of the invention that is of interest relates to a method of treating hyperglycemia, diabetes or insulin resistance in a mammalian patient in need of such treatment which comprises administering to said patient a compound as described above in accordance with formula I in an amount that is effective to treat hyperglycemia, diabetes or insulin resistance.

Another aspect of the invention that is of interest relates to a method of treating non-insulin dependent diabetes mellitus in a mammalian patient in need of such treatment comprising administering to the patient an anti-diabetic effective amount of a compound in accordance with formula I as described above.

Another aspect of the invention that is of interest relates to a method of treating obesity in a mammalian patient in need of such treatment comprising administering to said patient a compound in accordance with formula I as described above in an amount that is effective to treat obesity.

Another aspect of the invention that is of interest relates to a method of treating Syndrome X in a mammalian patient in need of such treatment, comprising administering to said patient a compound in accordance with formula I as described above in an amount that is effective to treat Syndrome X.

Another aspect of the invention that is of interest relates to a method of treating a lipid disorder selected from the group consisting of dyslipidemia, hyperlipidemia, hypertriglyceridemia, hypercholesterolemia, low HDL and high LDL in a mammalian patient in need of such treatment, comprising administering to said patient a compound as described above with respect to formula I in an amount that is effective to treat said lipid disorder.

Another aspect of the invention that is of interest relates to a method of treating atherosclerosis in a mammalian patient in need of such treatment, comprising administering to said patient a compound in accordance with formula I as described above in an amount effective to treat atherosclerosis.

Another aspect of the invention that is of interest relates to a method of treating a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment, comprising administering to the patient a compound in accordance with formula I as described above in an amount that is effective to treat said condition.

Another aspect of the invention that is of interest relates to a method of delaying the onset of a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound in accordance with formula I as described above in an amount that is effective to delay the onset of said condition.

Another aspect of the invention that is of interest relates to a method of reducing the risk of developing a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound of formula I as described above in an amount that is effective to reduce the risk of developing said condition.

Another aspect of the invention that is of interest relates to a method of treating a condition selected from the group consisting of:
(1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment,
comprising administering to the patient effective amounts of a compound of formula I as described above, and a compound selected from the group consisting of:
(a) DPP-IV inhibitors, such as the compounds disclosed in U.S. Pat. No. 6,699,871B1 granted on Mar. 2, 2004, incorporated herein by reference; (b) insulin sensitizers selected from the group consisting of (i) PPAR agonists and (ii) biguanides; (c) insulin and insulin mimetics; (d) sulfonylureas and other insulin secretagogues; (e) alpha glucosidase inhibitors; (f) other glucagon receptor antagonists; (g) GLP-1, GLP-1 mimetics, and GLP-1 receptor agonists; (h) GIP, GIP mimetics, and GIP receptor agonists; (i) PACAP, PACAP mimetics, and PACAP receptor 3 agonists; (j) cholesterol lowering agents selected from the group consisting of (i) HMG-CoA reductase inhibitors, (ii) sequestrants, (iii) nicotinyl alcohol, nicotinic acid and salts thereof, (iv) PPAR alpha agonists, (v) PPAR alpha/gamma dual agonists, (vi) inhibitors of cholesterol absorption, (vii) acyl CoA:holesterol acyltransferase inhibitors, (viii) anti-oxidants and (ix) LXR modulators; (k) PPAR delta agonists; (l) antiobesity compounds; (m) an ileal bile acid transporter inhibitor, (n) anti-inflammatory agents excluding glucocorticoids; (o) protein tyrosine phosphatase-1B (PTP-1B) inhibitors, and (p) CB1 antagonists/inverse agonists, such as rimonabant and those disclosed in WO03/077847A2, published on Sep. 25, 2003, and WO05/000809 published on Jan. 6, 2005, incorporated herein by reference,
said compounds being administered to the patient in amounts that are effective to treat said condition.

Another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor.

More particularly, another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor wherein the HMG-CoA reductase inhibitor is a statin.

Even more particularly, another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor, wherein the HMG CoA reductase inhibitor is a statin selected from the group consisting of lovastatin, simvastatin, pravastatin, fluvastatin, atorvastatin, itavastatin, ZD-4522 and rivastatin.

Another aspect of the invention that is of interest relates to a method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions comprising administering to a mammalian patient in need of such treatment therapeutically effective amounts of a compound of formula I as described above and an HMG-CoA reductase inhibitor.

Another aspect of the invention that is of interest relates to a method for delaying the onset or reducing the risk of developing atherosclerosis in a human patient in need of such treatment comprising administering to said patient effective amounts of a compound of formula I as described above and an HMG-CoA reductase inhibitor.

More particularly, another aspect of the invention that is of interest relates to a method for delaying the onset of, or reducing the risk of developing atherosclerosis in a human patient in need of such treatment comprising administering to said patient effective amounts of a compound of formula I as described above and an HMG-CoA reductase inhibitor wherein the HMG-CoA reductase inhibitor is a statin.

Even more particularly, another aspect of the invention that is of interest relates to a method for delaying the onset or reducing the risk of developing atherosclerosis in a human patient in need of such treatment comprising administering to said patient effective amounts of a compound of formula I as described above and an HMG-CoA reductase inhibitor wherein the HMG-CoA reductase inhibitor is a statin selected from the group consisting of: lovastatin, simvastatin, pravastatin, fluvastatin, atorvastatin, itavastatin, ZD-4522 and rivastatin.

Yet even more particularly, another aspect of the invention that is of interest relates to a method for delaying the onset or reducing the risk of developing atherosclerosis in a human patient in need of such treatment comprising administering to said patient effective amounts of a compound of formula I as described above and an HMG-CoA reductase inhibitor wherein the HMG-CoA reductase inhibitor is simvastatin.

Another aspect of the invention that is of interest relates to a method for delaying the onset or reducing the risk of developing atherosclerosis in a human patient in need of such treatment comprising administering to said patient effective amounts of a compound of formula I as described above and a cholesterol absorption inhibitor. More particularly, another aspect of the invention that is of interest relates to a method for delaying the onset or reducing the risk of developing atherosclerosis in a human patient in need of such treatment comprising administering to said patient effective amounts of a compound of formula I as described above and a cholesterol absorption inhibitor wherein the cholesterol absorption inhibitor is ezetimibe.

Another aspect of the invention that is of interest relates to a method for delaying the onset or reducing the risk of developing the other diseases and conditions mentioned above, in a mammalian patient in need of such treatment comprising administering to said patient effective amounts of a compound of formula I as described above, and a cholesterol absorption inhibitor.

More particularly, another aspect of the invention that is of interest relates to a method for delaying the onset or reducing the risk of developing the other diseases and conditions mentioned above, in a human patient in need of such treatment comprising administering to said patient effective amounts of a compound of formula I as described above, and a cholesterol absorption inhibitor, wherein the cholesterol absorption inhibitor is ezetimibe.

Another aspect of the invention that is of interest relates to a pharmaceutical composition comprising (1) a compound of formula I as described above; (2) a compound selected from the group consisting of: (a) DPP-IV inhibitors, such as those disclosed in U.S. Pat. No. 6,699,871B1 granted on Mar. 2, 2004; (b) insulin sensitizers selected from the group consisting of (i) PPAR agonists and (ii) biguanides; (c) insulin and insulin mimetics; (d) sulfonylureas and other insulin secretagogues; (e) alpha glucosidase inhibitors; (f) other glucagon receptor antagonists; (g) GLP-1, GLP-1 mimetics and GLP-1 receptor agonists; (h) GIP, GIP mimetics and GIP receptor agonists; (i) PACAP, PACAP mimetics, and PACAP receptor 3 agonists; (j) cholesterol lowering agents selected from the group consisting of (i) HMG-CoA reductase inhibitors, (ii) sequestrants, (iii) nicotinyl alcohol, nicotinic acid or a salt thereof, (iv) PPAR alpha agonists, (v) PPAR alpha/gamma dual agonists, (vi) inhibitors of cholesterol absorption, (vii) acyl CoA:cholesterol acyltransferase inhibitors, (viii) antioxidants and (ix) LXR modulators; (k) PPAR delta agonists; (l) antiobesity compounds; (m) an ileal bile acid transporter inhibitor; (n) anti-inflammatory agents other than glucocorticoids; (o) protein tyrosine phosphatase-1B (PTP-1B) inhibitors; and (p) CB1 antagonist/inverse agonists, such as rimonabant, and those disclosed in WO03/077847A2 published on Sep. 25, 2003 and WO05/000809 published on Jan. 6, 2005, and (3) a pharmaceutically acceptable carrier.

One pharmaceutical composition that is of interest is comprised of a compound of formula I as described herein, or a pharmaceutically acceptable salt or solvate thereof, in combination with a DPP-IV inhibitor selected from the group consisting of:

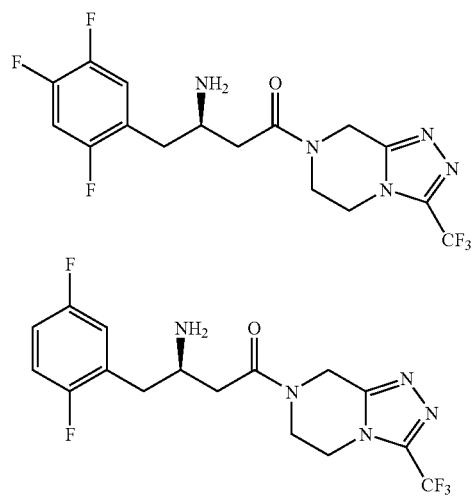

-continued

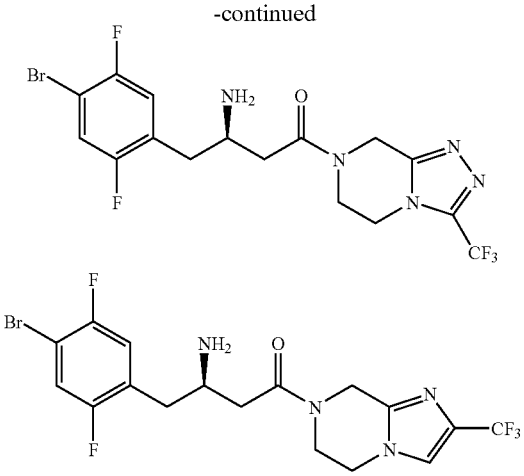

or a pharmaceutically acceptable salt or solvate thereof in combination with a pharmaceutically acceptable carrier.

Another pharmaceutical composition that is of particular interest is comprised of a compound of formula I as described herein, or a pharmaceutically acceptable salt, or solvate thereof, in combination with a CB1 receptor antagonist/inverse agonist, in combination with a pharmaceutically acceptable carrier. Examples of CB1 antagonist/inverse agonists that are of particular interest in the invention described herein include rimonabant, the following which are disclosed in WO03/077847A2 published on Sep. 25, 2003:

(1) N-[3-(4-chlorophenyl)-1-methyl-2-phenylpropyl]-2-(4-chlorophenyloxy)-2-methylpropanamide;
(2) N-[3-(4-chlorophenyl)-1-methyl-2-phenylpropyl]-2-(2-pyridyloxy)-2-methylpropanamide;
(3) N-[3-(4-chlorophenyl)-1-methyl-2-(3-pyridyl)propyl]-2-(4-chlorophenyloxy)-2-methylpropanamide;
(4) N-[3-(4-chlorophenyl)-1-methyl-2-phenylpropyl]-2-(3,5-difluorophenyloxy)-2-methylpropanamide;
(5) N-[3-(4-chlorophenyl)-2-phenyl-1-methylpropyl]-2-(3,5-dichlorophenyloxy)-2-methylpropanamide;
(6) N-[3-(4-chlorophenyl)-1-methyl-2-phenylpropyl]-2-(3-chlorophenyloxy)-2-methylpropanamide;
(7) N-[3-(4-chlorophenyl)-2-(3,5-difluorophenyl)-1-methylpropyl]-2-(2-pyridyloxy)-2-methylpropanamide;
(8) N-[3-(4-chlorophenyl)-1-methyl-2-phenyl-propyl]-2-(5-chloro-2-pyridyloxy)-2-methylpropanamide;
(9) N-[3-(4-chlorophenyl)-1-methyl-2-phenylpropyl]-2-(6-methyl-pyridyloxy)-2-methylpropanamide;
(10) N-[3-(4-chlorophenyl)-1-methyl-2-phenylpropyl]-2-(phenyloxy)-2-methylpropanamide;
(11) N-[(3-(4-chlorophenyl)-1-methyl-2-phenylpropyl]-2-(5-trifluoromethylpyridyloxy)-2-methylpropanamide;
(12) N-[3-(4-chlorophenyl)-2-(3-pyridyl)-1-methylpropyl]-2-(5-trifluoromethyl-2-pyridyloxy)methylpropanamide;
(13) N-[3-(4-chlorophenyl)-2-(3-cyanophenyl)-1-methylpropyl]-2-(5-trifluoromethyl-2-pyridyloxy)-2-methylpropanamide;
(14) N-[3-(4-chlorophenyl)-2-(5-chloro-3-pyridyl)-1-methylpropyl]-2-(5-trifluoromethyl-2-pyridyloxy)-2-methylpropanamide;
(15) N-[3-(4-chlorophenyl)-2-(5-methyl-3-pyridyl)-1-methylpropyl]-2-(5-trifluoromethyl-2-pyridyloxy)-2-methylpropanamide;
(16) N-[3-(4-chlorophenyl)-2-(5-cyano-3-pyridyl)-1-methylpropyl]-2-(5-trifluoromethyl-2-pyridyloxy)-2-methylpropanamide;
(17) N-[3-(4-chlorophenyl)-2-(3-methylphenyl)-1-methylpropyl]-2-(5-trifluoromethyl-2-pyridyloxy)-2-methylpropanamide;
(18) N-[3-(4-chlorophenyl)-2-phenyl-1-methylpropyl]-2-(4-trifluoromethyl-2-pyridyloxy)-2-methylpropanamide;
(19) N-[3-(4-chlorophenyl)-2-phenyl-1-methylpropyl]-2-(4-trifluoromethyl-2-pyrimidyloxy)-2-methylpropanamide;
(20) N-[3-(4-chlorophenyl)-1-methyl-2-(thiophen-3-yl)propyl]-2-(5-chloro-2-pyridyloxy)-2-methylpropanamide;
(21) N-[3-(5-chloro-2-pyridyl)-2-phenyl-1-methylpropyl]-2-(5-trifluoromethyl-2-pyridyloxy)-2-methylpropanamide;
(22) N-[3-(4-methyl-phenyl)-1-methyl-2-phenylpropyl]-2-(4-trifluoromethyl-phenyloxy)-2-methylpropanamide;
(23) N-[3-(4-fluoro-phenyl)-2-(3-cyano-phenyl)-1-methylpropyl]-2-(5-trifluoromethyl-2-pyridyloxy)-2-methylpropanamide;
(24) N-[3-(4-chlorophenyl)-2-(1-indoyl)-1-methyl)propyl]-2-(5-trifluoromethyl-2-oxypryridine-2-yl)-2-methylpropanamide;
(25) N-[3-(4-chlorophenyl)-2-(7-azaindol-N-yl)-1-methyl)propyl]-2-(5-trifluoromethyl-2-pyridyloxy)-2-methylpropanamide;
(26) N-[3-(4-chloro-phenyl)-2-(1-indolinyl)-1-methylpropyl]-2-(5-trifluoromethyl-2-pyridyloxy)-2-methylpropanamide;
(27) N-[3-(4-chloro-phenyl)-2-(N-methyl-anilino)-1-methylpropyl]-2-(5-trifluoromethyl-2-pyridyloxy)-2-methylpropanamide;
(28) N-[3-(4-methoxy-phenyl)-2-(3-cyano-phenyl)-1-methylpropyl]-2-(5-trifluoromethyl-2-pyridyloxy)-2-methylpropanamide;
(29) N-[3-(4-chlorophenyl)-2-(3-cyanophenyl)-1-methylpropyl]-2-(6-trifluoromethyl-4-pyrimidyloxy)-2-methylpropanamide;
(30) N-[2-(3-cyanophenyl)-1,4-dimethylpentyl]-2-(5-trifluoromethyl-2-pyridyloxy)-2-methylpropanamide;
(31) N-[3-(4-chlorophenyl)-2-(1-oxido-5-cyano-3-pyridyl)-1-methylpropyl]-2-(5-trifluoromethyl-2-pyridyloxy)-2-methylpropanamide;
(32) N-[2-(3-cyanophenyl)-3-cyclobutyl-1-methylpropyl]-2-(5-trifluoromethyl-2-pyridyloxy)-2-methylpropanamide;
(33) N-[2-(3-cyanophenyl)-1-methyl-heptyl]-2-(5-trifluoromethyl-2-pyridyloxy)-2-methylpropanamide;
(34) N-[2-(3-cyanophenyl)-3-cyclopentyl-1-methylpropyl]-2-(5-trifluoromethyl-2-pyridyloxy)-2-methylpropanamide;
(35) N-[2-(3-cyanophenyl)-3-cyclohexyl-1-methylpropyl]-2-(5-trifluoromethyl-2-pyridyloxy)-2-methylpropanamide;

and in WO05/000809 published on Jan. 6, 2005, which includes the following:

3-{1-[Bis(4-chlorophenyl)methyl]azetidin-3-ylidene}-3-(3,5-difluorophenyl)-2,2-dimethylpropanenitrile
1-{1-[1-(4-chlorophenyl)pentyl]azetidin-3-yl}-1-(3,5-difluorophenyl)-2-methylpropan-2-ol
3-((S)-(4-chlorophenyl){3-[(1S)-1-(3,5-difluorophenyl)-2-hydroxy-2-methylpropyl]azetidin-1-yl}methyl)benzonitrile
3-((S)-(4-chlorophenyl){3-[(1S)-1-(3,5-difluorophenyl)-2-fluoro-2-methylpropyl]azetidin-1-yl}methyl)benzonitrile
3-((4-chlorophenyl){3-[1-(3,5-difluorophenyl)-2,2-dimethylpropyl]azetidin-1-yl}methyl)benzonitrile
3-((1S)-1-{1-[(S)-(3-cyanophenyl)(4-cyanophenyl)methyl]azetidin-3-yl}-2-fluoro-2-methylpropyl)-5-fluorobenzonitrile 3-[(S)-(4-chlorophenyl)(3-{(1S)-2-fluoro-1-[3-fluoro-5-(4H-1,2,4-triazol-4-yl)phenyl]-2-methylpropyl}azetidin-1-yl)methyl]benzonitrile and
5-((4-chlorophenyl){3-[(1S)-1-(3,5-difluorophenyl)-2-fluoro-2-methylpropyl]azetidin-1-yl}methyl)thiophene-3-carbonitrile,
as well as the pharmaceutically acceptable salts and solvates thereof, in combination with a pharmaceutically acceptable carrier.

Optical Isomers—Diastereomers—Geometric Isomers—Tautomers

Many of the compounds of formula I contain one or more asymmetric centers and thus occur as racemates and racemic mixtures, single enantiomers, diastereomeric mixtures and individual diastereomers. The present invention includes all such isomeric forms of the compounds, in pure form as well as in mixtures.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as ketoenol tautomers. The individual tautomers as well as mixtures thereof are encompassed with the compounds of Formula I.

Salts and Solvates

Salts and solvates of compounds of formula I are included in the present invention. The term "pharmaceutically acceptable salts" refers to salts prepared from pharmaceutically acceptable substantially non-toxic bases or acids including inorganic or organic bases and inorganic or organic acids, as well as salts that can be converted into pharmaceutically acceptable salts. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like.

Particularly preferred are citric, hydrobromic, hydrochloric, maleic, phosphoric, sulfuric, and tartaric acids.

Solvates as used herein refers to the compound of formula I or a salt thereof, in association with a solvent, such as water. Representative examples include hydrates, hemihydrates, trihydrates and the like.

References to the compounds of Formula I are intended to include the pharmaceutically acceptable salts and solvates.

This invention relates to a method of inhibiting the activity of glucagon by antagonizing the glucagon receptor, thereby reducing the rate of gluconeogenesis and glycogenolysis, and the concentration of glucose in plasma.

The compounds of formula I can be used in the manufacture of a medicament for the prophylactic or therapeutic treatment of disease states in mammals associated with elevated levels of glucose, comprised of combining the compound of formula I with the carrier materials to provide the medicament.

Dose Ranges

The prophylactic or therapeutic dose of a compound of formula I will, of course, vary with the nature or severity of the condition to be treated, the particular compound selected and its route of administration. It will also vary according to the age, weight and response of the individual patient. In general, the daily dose range lies within the range of from about 0.001 mg to about 100 mg per kg body weight, preferably about 0.01 mg to about 50 mg per kg, and more preferably 0.1 to 10 mg per kg, in single or divided doses. It may be necessary to use dosages outside of these limits in some cases. The terms "effective amount", "anti-diabetic effective amount" and the other terms appearing throughout the application addressing the amount of the compound to be used refer to the dosage ranges provided, taking into account any necessary variation outside of these ranges, as determined by the skilled physician.

Representative dosages of compounds of formula I, as well as the pharmaceutically acceptable salts and solvates thereof, for adults range from about 0.1 mg to about 1.0 g per day, preferably about 1 mg to about 500 mg, in single or divided doses. Representative dosages of compounds used in combination with the compounds of formula I are known, or the determination thereof is within the level of skill in the art, taking into account the description provided herein.

When intravenous or oral administration is employed, a representative dosage range is from about 0.001 mg to about 100 mg (preferably from 0.01 mg to about 10 mg) of a compound of Formula I per kg of body weight per day, and more preferably, about 0.1 mg to about 10 mg of a compound of formula I per kg of body weight per day.

When used in combination with other agents, the dosages noted above for the glucagon antagonist are provided along with the usual dose for the other medication. For example, when a DPP-IV inhibitor such as those disclosed in U.S. Pat. No. 6,699,871B1, is included, the DPP-IV inhibitor can be used in an amount ranging from about 1.0 mg to as high as about 1000 mg, preferably about 2.5 mg to about 250 mg, and in particular, about 50 mg or about 100 mg administered in single daily doses or in divided doses as appropriate. Similarly, when the glucagon receptor antagonist is used in combination with a CB1 antagonist/inverse agonist, the CB1 antagonist/inverse agonist can be used in an amount ranging from as low as about 0.1 mg to as high as about 1000 mg, more particularly, in an amount ranging from about 1.0 mg to about 100 mg, and even more particularly, in an amount from about 1.0 mg to about 10 mg, administered in single daily doses or in divided doses as appropriate. Examples of doses of CB1 antagonist/inverse agonist include 1 mg, 2 mg, 3 mg, 4 mg, 5 mg, 6 mg, 7 mg, 8 mg, 9 mg and 10 mg.

Pharmaceutical Compositions

As mentioned above, the pharmaceutical composition comprises a compound of Formula I or a pharmaceutically acceptable salt or solvate thereof and a pharmaceutically acceptable carrier. The term "composition" encompasses a product comprising the active and inert ingredient(s), (pharmaceutically acceptable excipients) that make up the carrier, as well as any product which results, directly or indirectly, from the combination, complexation or aggregation of any two or more of the ingredients, or from dissociation of one or more of the ingredients, or from other types of reactions or interactions between ingredients. Preferably the composition is comprised of a compound of formula I in an amount that is effective to treat, prevent or delay the onset of type 2 diabetes mellitus, in combination with the pharmaceutically acceptable carrier.

Any suitable route of administration may be employed for providing a mammal, especially a human with an effective dosage of a compound of the present invention. For example, oral, rectal, topical, parenteral, ocular, pulmonary, nasal, and the like may be employed. Examples of dosage forms include tablets, troches, dispersions, suspensions, solutions, capsules, creams, ointments, aerosols and the like, with oral tablets being preferred.

In preparing oral compositions, any of the usual pharmaceutical media may be employed, such as, for example, water, glycols, oils, alcohols, flavoring agents, preservatives, coloring agents and the like, in the case of oral liquids, e.g., suspensions, elixirs and solutions; or carriers such as starches, sugars, microcrystalline cellulose, diluents, granulating agents, lubricants, binders, disintegrating agents and the like in the case of oral solids, e.g., powders, capsules and tablets. Solid oral preparations are preferred. Because of their ease of administration, tablets and capsules represent the most advantageous oral dosage unit forms. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any acceptable pharmaceutical process. All such methods include the step of combining the active ingredient(s) with the carrier components. In general, the compositions are prepared by uniformly and intimately admixing the active ingredient(s) with a liquid or finely divided solid carrier component, and then, if necessary, manipulating the blend into the desired product form. For example, a tablet may be prepared by compression or molding. Compressed tablets may be prepared by compressing free-flowing powder or granules, containing the active(s) optionally mixed with one or more excipients, e.g., binders, lubricants, diluents, surfactants and dispersants. Molded tablets may be made by molding a mixture of the powdered compound moistened with an inert liquid. Desirably, each tablet may contain, for example, from about 0.1 mg to about 1.0 g of the active ingredient and each cachet or capsule contains from about 0.1 mg to about 500 mg of the active ingredient.

The following are examples of pharmaceutical dosage forms containing a compound of Formula I:

| Injectable Suspension (im.) | mg/mL |
|---|---|
| Compound of Formula 1 | 10.0 |
| Methylcellulose | 5.0 |
| Tween 80 | 0.5 |
| Benzyl alcohol | 9.0 |
| Benzalkonium chloride | 1.0 |
| Water for injection | t.d. 1.0 mL |

| Capsule | mg/capsule |
|---|---|
| Compound of Formula 1 | 25.0 |
| Lactose | 735 |
| Mg Stearate | 1.5 |
| Total | 600 mg |

| Tablet | Mg/tablet |
|---|---|
| Compound of Formula 1 | 25.0 |
| Microcrystalline Cellulose | 415 |
| Povidone | 14.0 |
| Pregelatinized Starch | 4.35 |
| Magnesium Stearate | 2.5 |
| Total | 500 mg |

| Aerosol | Per Canister |
|---|---|
| Compound of Formula 1 | 250 mg |
| Lecithin, NF Liq. Conc. | 1.2 mg |
| Trichloromethane, NF | 4.025 g |
| Dichlorodifluoromethane, NF | 12.15 g |

Combination Therapy

As previously described, the compounds of Formula I may be used in combination with other drugs that are used in the treatment/prevention/delaying the onset of type 2 diabetes mellitus, as well as other diseases and conditions described herein, for which compounds of Formula I are useful. Other drugs may be administered, by a route and in an amount commonly used, contemporaneously or sequentially with a compound of Formula I. When a compound of Formula I is used contemporaneously with one or more other drugs, a combination pharmaceutical composition containing such other drugs in addition to the compound of Formula I is preferred. Accordingly, the pharmaceutical compositions of the present invention include those that alternatively contain one or more other active ingredients, in addition to a compound of Formula I. Examples of other active ingredients that may be combined with a compound of Formula I, either administered separately or in the same pharmaceutical compositions, include, but are not limited to: (a) biguanides (e.g., buformin, metformin, phenformin), (b) PPAR agonists (e.g., troglitazone, pioglitazone, rosiglitazone), (c) insulin, (d) somatostatin, (e) alpha-glucosidase inhibitors (e.g., voglibose, miglitol, acarbose), (f) DPP-IV inhibitors, such as those disclosed in U.S. Pat. No. 6,699,871B1 granted on Mar. 2, 2004 (g) LXR modulators and (h) insulin secretagogues (e.g., acetohexamide, carbutamide, chlorpropamide, glibornuride, gliclazide, glimerpiride, glipizide, gliquidine, glisoxepid, glyburide, glyhexamide, glypinamide, phenbutamide, tolazamide, tolbutamide, tolcyclamide, nateglinide and repaglinide), and CB1 inhibitors, such as rimonabant and those compounds disclosed in WO03/077847A2 published on Sep. 25, 2003 and in WOOS/000809 A1 published on Jan. 6, 2005.

The weight ratio of the compound of the Formula I to the second active ingredient may be varied within wide limits and depends upon the effective dose of each active ingredient. Generally, an effective dose of each will be used. Thus, for example, when a compound of the Formula I is combined with a PPAR agonist the weight ratio of the compound of the Formula I to the PPAR agonist will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

For combination products, the compound of formula I may be combined with any other active ingredients and then added to the carrier ingredients; alternatively the order of mixing may be varied.

Examples of pharmaceutical combination compositions include: (1) a compound according to formula I, (2) a compound selected from the group consisting of: (a) DPP-IV inhibitors; (b) insulin sensitizers selected from the group consisting of (i) PPAR agonists and (ii) biguanides; (c) insulin and insulin mimetics; (d) sulfonylureas and other insulin secretagogues; (e) a-glucosidase inhibitors; (f) CB1 receptor antagonists/inverse agonists; (g) GLP-1, GLP-1 mimetics, and GLP-1 receptor agonists; (h) GIP, GIP mimetics, and GIP receptor agonists; (i) PACAP, PACAP mimetics, and PACAP receptor 3 agonists; (j) cholesterol lowering agents selected from the group consisting of (i) HMG-CoA reductase inhibitors, (ii) sequestrants, (iii) nicotinyl alcohol, nicotinic acid or a salt thereof, (iv) PPAR alpha agonists, (v) PPAR alpha/gamma dual agonists, (vi) inhibitors of cholesterol absorption, (vii) acyl CoA:cholesterol acyl transferase inhibitors, (viii) anti-oxidants and (ix) LXR modulators; (k) PPAR delta agonists; (l) antiobesity compounds; (m) an ileal bile acid transporter inhibitor; (n) anti-inflammatory agents other than glucocorticoids; and (o) protein tyrosine phosphatase-1B (PTP-1B) inhibitors; (p) CB1 antagonist/inverse agonists and (3) a pharmaceutically acceptable carrier.

The compounds of formula I can be synthesized in accordance with the general schemes provided below, where $R^1$-$R^3$, $R^a$, $R^b$, $R^4$ and A are defined as above. Throughout the synthesis schemes, abbreviations are used with the following meanings unless otherwise indicated:

One such procedure when $AR^3$ is a 4-hydroxyphenyl group is shown in Scheme 1. Reaction of a cyclic ketone 1 with phenol in presence of an acid such as concentrated HCl (aq) or p-toluenesulfonic acid provides the diphenol 2 (J. March, *Advanced Organic Chemistry*, $4^{th}$ ed.; Wiley: New York, 1992; p. 548). Monoprotection of one of the phenolic groups, for example as a benzyl ether as shown in Scheme 1, may be achieved by reaction of the diphenol with an equivalent of benzyl bromide in a solvent such as DMF and a base such as $K_2CO_3$ or $CsCO_3$ for 1 to 16 h at ambient or elevated temperatures. The monoprotected product 3a may be separated as necessary from unreacted starting material 2 and the bis-benzylated product. The remaining phenolic group may then be converted to the trifluoromethanesulfonate 4a by reaction with trifluoromethanesulfonic anhydride in an aprotic solvent such as DCM in presence of a base such as pyridine at reduced temperatures for 0.5 to 16 h. Reaction of the trifluoromethanesulfonate under a CO atmosphere in presence of a metal catalyst such as $Pd(OAc)_2$, a ligand such as 1,1'-bis

| | |
|---|---|
| aq = aqueous | BuLi, n-BuLi = n-butyllithium |
| Bu = butyl, t-Bu = t-butyl | Bn and Bnzl = benzyl |
| BOC, Boc = t-butyloxycarbonyl | CBZ, Cbz = Benzyloxycarbonyl |
| DABCO = 1,4-diazabicyclo[2.2.2]octane | iPrOH = isopropanol |
| DCC = Dicyclohexylcarbodiimide | DCM = dichloromethane |
| DIEA = diisopropylethylamine | DMF = N,N-dimethylformamide |
| dppf = 1,1'-bis(diphenylphosphino)ferrocene | Triflate = trifluoromethanesulfonate |
| | EDC = 1-ethyl-3-(3-dimethylaminopropyl)-carbodiimide |
| DMSO = dimethylsulfoxide | Et = ethyl |
| DIAD = diisopropylazodicarboxylate | EtOH = ethanol |
| DMAP = 4-Dimethylaminopyridine | NMR = nuclear magnetic resonance |
| ESI = electrospray ionization | FAB-mass spectrum = Fast atom bombardment-mass spectroscopy |
| EtOAc = ethyl acetate | |
| eq. = equivalent(s) | HPLC = High pressure liquid chromatography |
| HOAc = acetic acid | LAH = Lithium aluminum hydride |
| LCMS, LC-MS = high pressure liquid chromatography mass spectrometry | Pt/C = platinum on activated carbon |
| | PBS = phosphate buffered saline |
| HOBT, HOBt = Hydroxybenztriazole | KHMDS = potassium bis(trimethylsilyl)amide |
| LHMDS = lithium bis(trimethylsilyl)amide | TFA = Trifluoroacetic acid |
| | TMS = Trimethylsilane |
| Me = methyl | NMe2 = dimethylamino |
| Ph = phenyl | 2ClPh = 2-chlorophenyl |
| THF = Tetrahydrofuran | Py, Pyr = pyridyl |
| C6H11 = cyclohexyl | PyBOP = Benzotrazol-1-yloxytripyrrolidinophosphonium hexafluorophosphate |
| iPr, iPr = isopropyl | |
| 2,4-diClPh = 2,4-dichlorophenyl | Pd/C = palladium on activated carbon |
| TLC = thin layer chromatography | |

In one embodiment of the present invention, the compounds I may be prepared from alkyl 4-[(aryl)cycloalkyl]benzoate and alkyl 4-[(heteroaryl)cycloalkyl]benzoate intermediates 5, where $R^i$ represents a $C_{1-4}$ alkyl group. Such compounds 5 may be prepared by a variety of procedures by those (diphenylphosphino)ferrocene and a base such as DIEA in an alcohol solvent such as MeOH or BuOH at elevated temperatures for 1 to 24 h provides the corresponding alcohol ester 5a. If so desired, the benzyl group may be removed, for example by hydrogenation using catalytic palladium on carbon under a hydrogen atmosphere for 1 to 24 h, to provide the phenol ester 5b.

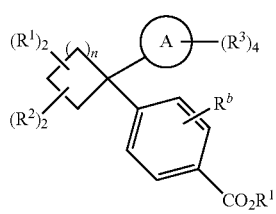

5

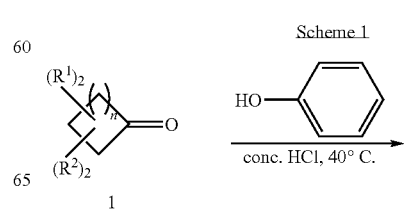

Scheme 1

1

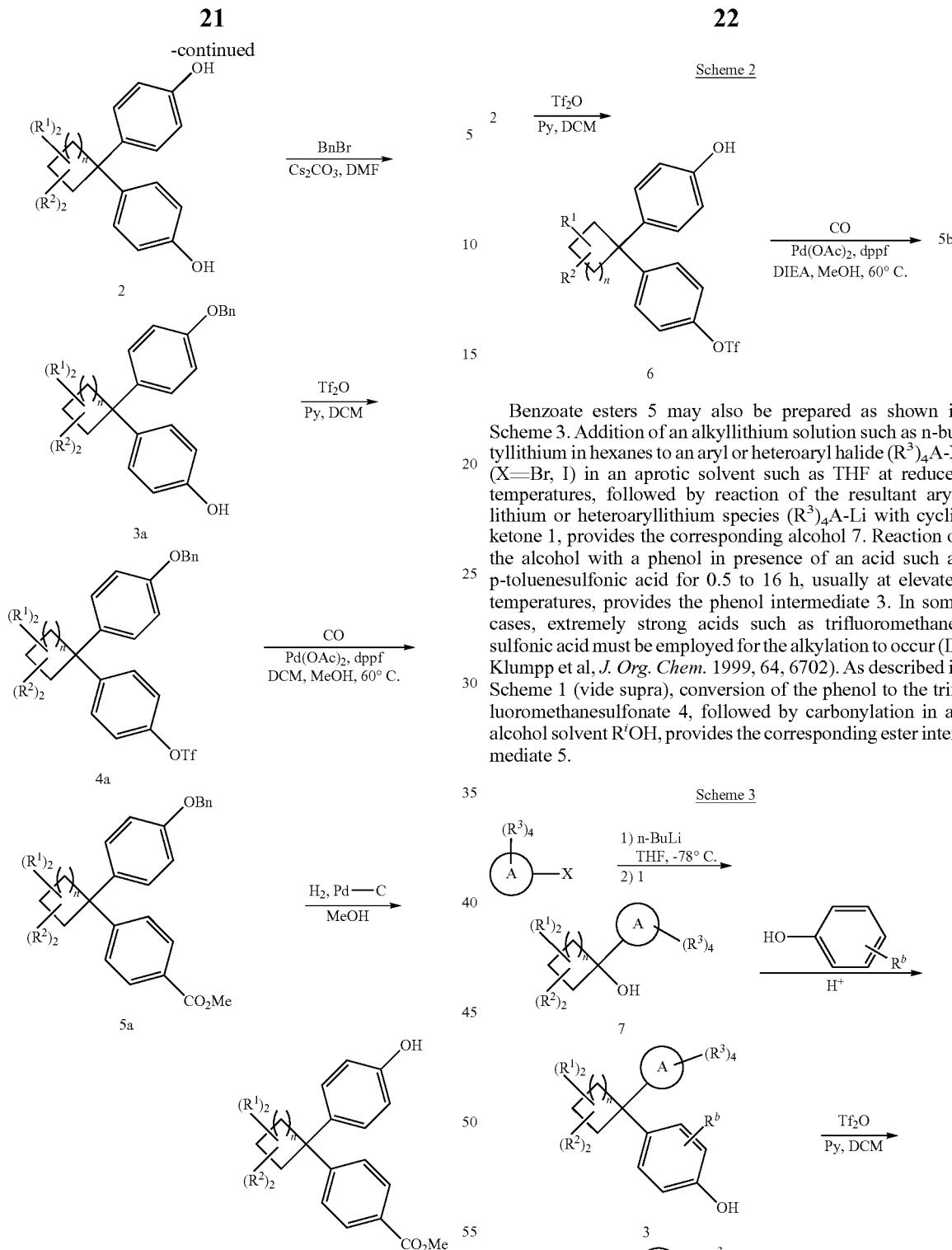

In an alternative approach, the phenol ester 5b may be obtained from the bis-phenol 2 as depicted in Scheme 2. Thus, conversion of 2 to the monotrifluoromethanesulfonate 6 by reaction with an equivalent of trifluoromethanesulfonic anhydride in an aprotic solvent such as DCM in presence of a base such as pyridine at reduced temperatures for 0.5 to 16 h, followed by carbonylation of the trifluoromethanesulfonate as described in Scheme 1, provides the phenolic ester 5b.

Benzoate esters 5 may also be prepared as shown in Scheme 3. Addition of an alkyllithium solution such as n-butyllithium in hexanes to an aryl or heteroaryl halide $(R^3)_4$A-X (X=Br, I) in an aprotic solvent such as THF at reduced temperatures, followed by reaction of the resultant aryllithium or heteroaryllithium species $(R^3)_4$A-Li with cyclic ketone 1, provides the corresponding alcohol 7. Reaction of the alcohol with a phenol in presence of an acid such as p-toluenesulfonic acid for 0.5 to 16 h, usually at elevated temperatures, provides the phenol intermediate 3. In some cases, extremely strong acids such as trifluoromethanesulfonic acid must be employed for the alkylation to occur (D. Klumpp et al, *J. Org. Chem.* 1999, 64, 6702). As described in Scheme 1 (vide supra), conversion of the phenol to the trifluoromethanesulfonate 4, followed by carbonylation in an alcohol solvent R'OH, provides the corresponding ester intermediate 5.

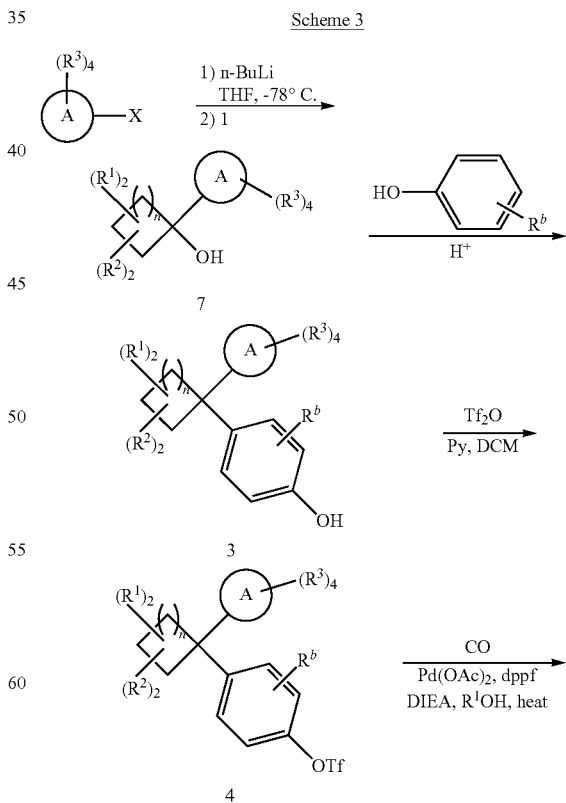

Ester intermediates 5 may readily be converted to final products I using methods known to those skilled in the art.

Shown in Scheme 4, saponification of the ester 5 may be achieved using a base such as aqueous lithium- or sodium hydroxide in a polar solvent such as tetrahydrofuran, dioxane, methanol, ethanol or a mixture of similar solvents to provide carboxylic acid 8. The acid may then be elaborated with the appropriate amine $H_2NR^a$ using a coupling reagent such as 1-ethyl-3-(3-dimethylaminopropyl)-carbodiimide (EDC) and 1-hydroxybenzotriazole (HOBt), or benzotriazole-1-yloxytrispyrrolidino-phosphonium hexafluorophosphate (PyBOP) and a base, generally diisopropylethylamine, in a solvent such as N,N-dimethylformamide (DMF) or methylene chloride for 0.5 to 48 h at ambient or slightly elevated temperatures. For compounds I where $Ra=-CH_2CH_2CO_2R^4$ or $-CH_2CH(OH)CO_2R^4$ and $R^4=C_{1-6}$alkyl, the ester may be readily cleaved to provide the carboxylic acid ($R^4=H$) by treatment with a base such as aqueous lithium or sodium hydroxide in a polar solvent such as tetrahydrofuran, dioxane, methanol, ethanol or a mixture of similar solvents at ambient or elevated temperatures. Additionally, when $R^4$ is a tert-butyl group it is conveniently removed by treatment with an acid such as trifluoroacetic acid, commonly as a 1:1 mixture with methylene chloride, for 0.5 to 8 h at ambient temperature.

Scheme 4

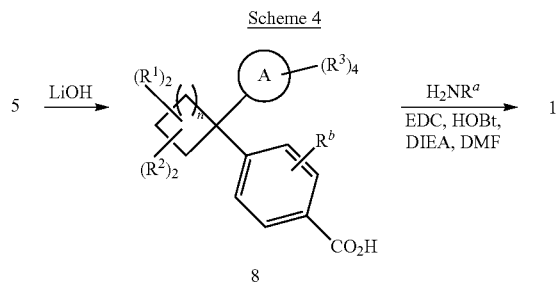

As will be known to those skilled in the art, in all schemes, the product I and all synthetic intermediates may be purified from unwanted side products, reagents and solvents by recrystallization, trituration, preparative thin layer chromatography, flash chromatography on silica gel as described by W. C. Still et al, *J. Org. Chem.*, 1978, 43, 2923, or reverse-phase HPLC. Compounds purified by HPLC may be isolated as the corresponding salt.

Additionally, in some instances compound 5, previous or subsequent intermediates, or final compound I may be comprised of a mixture of enantiomers or diastereomers, including cis/trans diastereomers. As will be known to those skilled in the art, such enantiomers and diastereomers may be separated by various methods including crystallization, chromatography using a homochiral stationary phase and, in the case of diastereomers, normal-phase and reverse-phase chromatography.

In some cases, the product I, the penultimate ester 9, the benzoate ester 5 and other intermediates from the reactions described in the schemes will be further modified. These manipulations may include, but are not limited to, substitution, reduction, oxidation, alkylation, acylation, and hydrolysis reactions, which are commonly known to those skilled in the art. For illustrative purposes, transformations depicted in the following schemes are shown for $AR^3$=4-hydroxyphenyl; this is in no way intended to limit the invention, however, as other hydroxylated aromatic and heteroaromatic groups, as well as other $AR^3$ groups such as aryl- and heteroaryl halides, may undergo transformations analogous to those described below.

As shown in Scheme 5, an aromatic or heteroaromatic hydroxyl group A-OH of intermediates such as 5b may be readily alkylated with an alkyl- or benzyl halides $R^{ii}X$ (X=Cl, Br or I) in a solvent such as DMF and a base such as $K_2CO_3$ or $CsCO_3$ at ambient or elevated temperatures to provide the corresponding ether 5c. Such ethers may also be readily prepared under Mitsunobu conditions, involving reaction of the aromatic hydroxyl group A-OH with the corresponding alkyl or benzyl alcohol $R^{ii}OH$ in an aprotic solvent such as DCM or THF in presence of a phosphine such as triphenylphosphine and an azodicarbonyl compound such as DIAD (O. Mitsunobu, *Synthesis* 1981, p. 1). The ether 5c may then be carried on to final products I as described in Scheme 4 (vide supra) by saponification of the ester to give acid 8a, then coupling of the acid to the desired amine such as, for example, β-alanine tert-butyl ester as shown in Scheme 5 to provide compound Ib. If so desired, the ester may be removed as described above (vide supra) to provide the carboxylic acid Ic. Also depicted in Scheme 5, the order of reactions may be reversed, with ester 5b first being converted to amide Ia using the procedures outlined in Scheme 4 (vide supra), followed by alkylation of the phenolic group to give ether intermediate Ib. Again, removal of the tert-butyl group if so desired provides carboxylic acid Ic.

Scheme 5

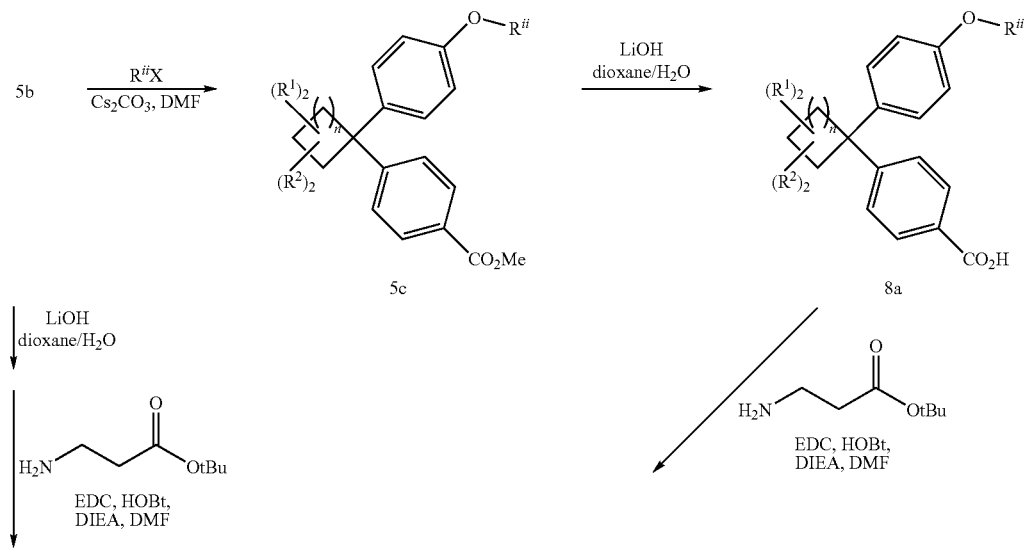

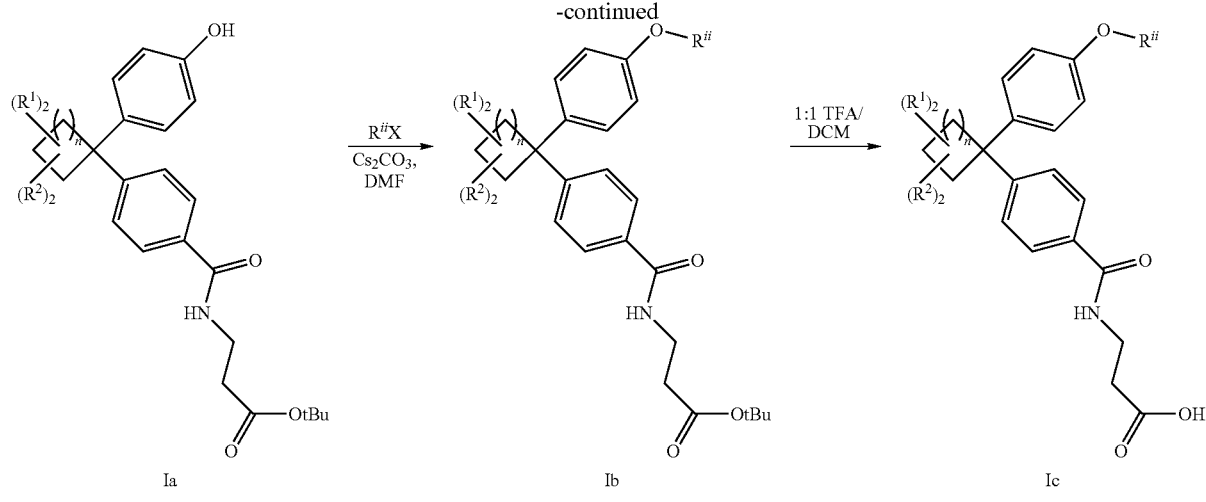

Shown in Scheme 6, the phenol ester 5b may be converted to the aryl trifluoromethanesulfonate 5d by reaction with trifluoromethanesulfonic anhydride in the presence of a base such as pyridine in an aprotic solvent such as DCM. The aryl trifluoromethanesulfonate may be further elaborated using procedures known to those skilled in the art. For example, reaction of 5d with aryl-, heteroaryl-, alkyl- or alkenylboronic acids $R^{iii}$—B(OH)$_2$ in the presence of a catalyst such as palladium acetate and ligand such as tri-o-tolylphosphine and a base such as cesium carbonate in a solvent such as toluene at elevated temperatures for 0.5 to 16 h provides the corresponding carbon-linked compounds 5e (A. Suzuki, *J. Organomet. Chem.* 1999, 576, 147). Aryl trifluoromethanesulfonates such as 5d may also be coupled to various heteroatomic compounds including amines, amides, alcohols, phenols, thiols and nitrogenous heterocycles to provide the corresponding heteroatom-linked species (S. Ley and A. Thomas, *Angew. Chem. Int. Ed.* 2003, 42, 5400). For example, also shown in Scheme 6, reaction of aryl triflate 5d with an alkyl or aryl amine HNR$^{iv}$R$^v$ in presence of a catalyst such as Pd(OAc)$_2$, a ligand such as 2-(di-tert-butylphosphino)biphenyl and a base such as sodium tert-butoxide in an aprotic solvent such as toluene at elevated temperatures provides the aniline compound 5f (*J. Org. Chem.* 2000, 65, 1158). All intermediates 5e, 5f, 9d and 9e may be converted to final products T as described in Scheme 4 (vide supra). Amide compound Ia may also be converted to trifluoromethanesulfonate intermediate 9 by reaction with trifluoromethanesulfonic anhydride in the presence of a base such as pyridine in an aprotic solvent such as DCM at reduced temperatures. The trifluoromethanesulfonate may then be analogously modified to provide the corresponding products Id and Ie.

Scheme 6

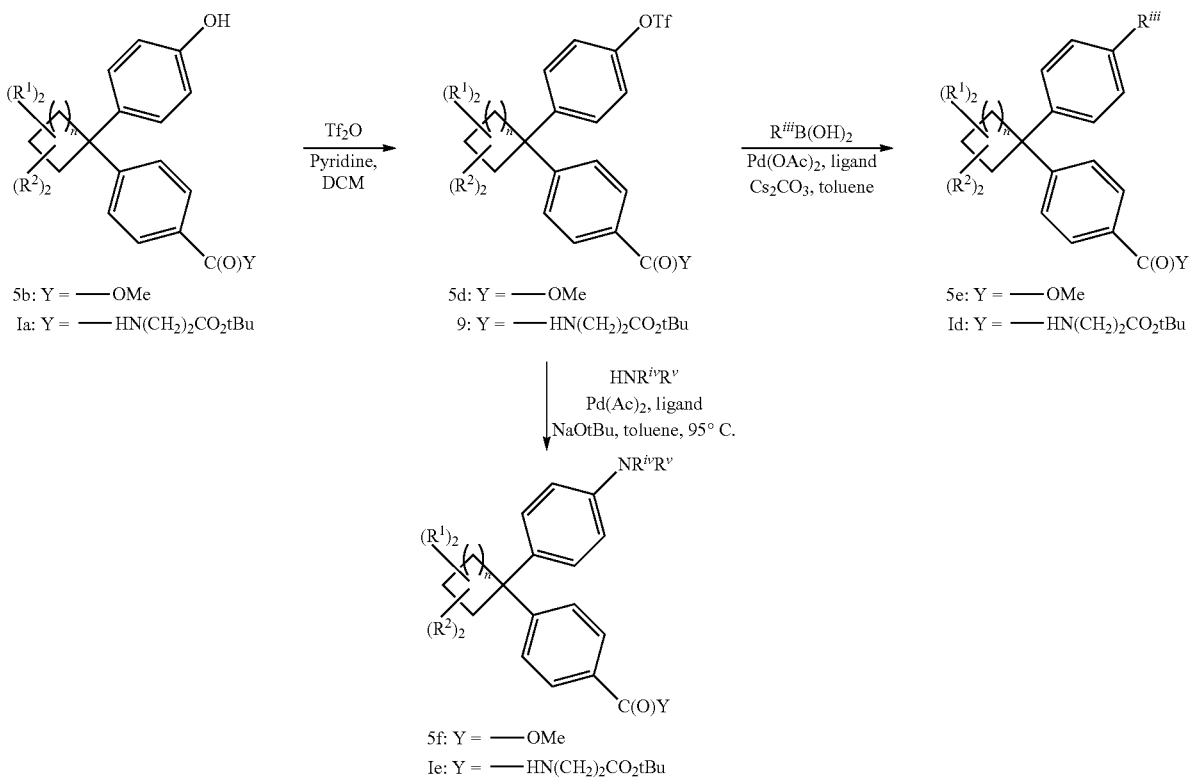

Hydroxyaromatic groups A-OH may also be readily halogenated. For example, as depicted in Scheme 7, reaction of phenol 5b with halogenating agents such as N-halosuccinimides (halo=Cl, Br, I) can provide the mono-halogenated intermediates 5g-i and bis-halogenated compounds 5j-l. In addition, treatment of 5b in neat $SO_2Cl_2$ at 50° C. for 16 h cleanly provides the bis-chloride 5j (*Org. Synth.* 1955, p. 267), while reaction of 5b with one equivalent benzyltrimethylammonium dichloroiodate in a mixed solvent of MeOH/DCM in presence of a base such as $CaCO_3$ at ambient temperature for 1 to 16 h provides mainly the monoiodide 5i (*Heterocycles,* 2002, 56, 465). The phenolic group may then be alkylated as described in Scheme 5 (vide supra), or when X=Cl, the phenol may be converted to the trifluoromethanesulfonate and further modified as outlined in Scheme 6 (vide supra).

Also depicted in Scheme 7, the bromophenol 5h and iodophenol 5i may be further elaborated to provide fused heterocycles by those skilled in the art. For example, reaction of iodophenol 5j with a terminal alkyl or aryl alkyne $HCCR^{vi}$ in a solvent such as DMF containing a catalysts such as CuI and $PdCl_2(Ph_3P)_2$, a base such as DIEA provides the 2-substituted benzofuran 5m (*Synthesis,* 1986, p. 749). Reaction of 5i with an alkyne $R^{vii}CCR^{viii}$ under a CO atmosphere in presence of $Zn(CN)_2$ and $Pd_2dba_3$, and a ligand such as 1,1'-bis(diphenylphosphino)ferrocene in DMF at elevated temperatures provides the coumarin 5n (*J. Organomet. Chem.* 2003, p. 687). The intermediates thus derived from 5b may then be carried on to final products I as described in Scheme 4 (vide supra).

General Experimental: Chemical reactions were monitored by LC-MS, and the purity and identity of the reaction products were assayed by LC-MS using one of the following conditions:

Method A: Column: Waters Xterra C18 (3.0×50 mm). Gradient: 10-100% $CH_3CN$ (containing 0.05% TFA)/$H_2O$ (containing 0.06% TFA) over 3.75 min @ 1 mL/min Method B: Column: MetaChem Polaris (4.6×50 mm). Gradient: 5-95% $CH_3CN/H_2O$, (both with 0.05% TFA) over 2.5 min @ 2.5 mL/min Method C: Column: Waters Xterra C18 (3.0×50 mm), Gradient: 10-98% $CH_3CN$ (containing 0.05% TFA)/$H_2O$ (containing 0.06% TFA) over 3.25 min @ 1.5 mL/min Method D: Column: Waters Xterra C18 (3.0×50 mm). Gradient: 10-98% $CH_3CN$ (containing 0.05% TFA)/$H_2O$ (containing 0.06% TFA) over 1.25 min @ 1.5 mL/min Method E: Column: Waters Xterra C18 (3.0×50 mm). Gradient 10-100% MeCN (containing 0.05% formic acid)/$H_2O$ (containing 0.06% formic acid) over 3.75 min @ 1 mL/min Preparative HPLC was performed on either a YMC-Pack Pro C18 column (150×20 mm i.d.) or a Kromasil 100-10 C8 column (100×30 mm i.d.) at an initial flow rate of 4 mL/min for 1.35 min, followed by 20 mL/min for 10.6 min. The gradients employed during the faster part of the run are described, and all runs were followed with 100% organic at 20 mL/min for 0.5 min.

Flash chromatography on silica gel was performed using pre-packed silica gel columns on a Biotage Horizon or

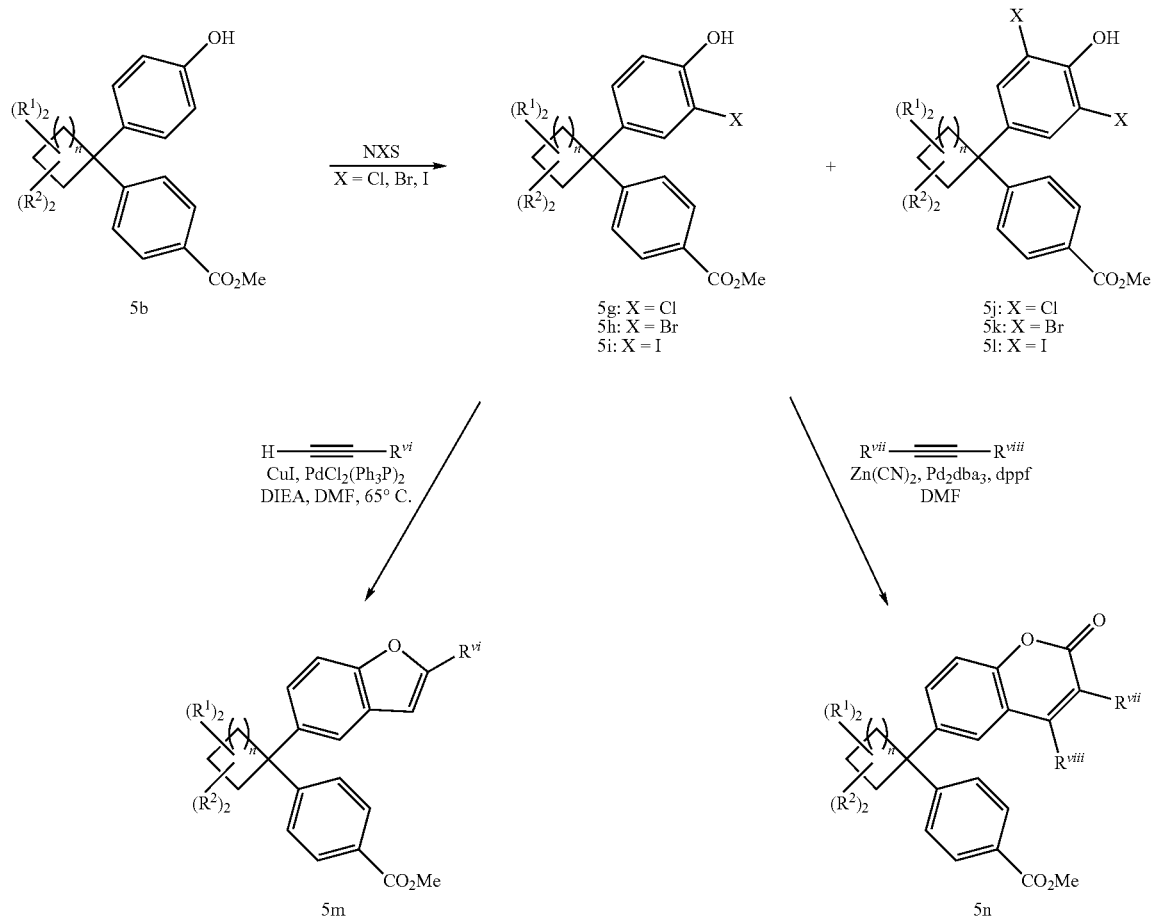

Scheme 7

Biotage SP-1 instrument equipped with a UV detector using the gradients described in the experimental section.

The following examples are provided so that the invention might be more fully understood. They should not be construed as limiting the invention in any way.

INTERMEDIATE 1

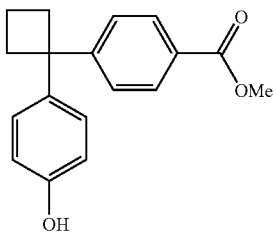

Step A: 4,4'-Cyclobutane-1,1-diyldiphenol

Cyclobutanone (1.2 g, 17 mmol) and phenol (4.8 g, 51 mmol) were stirred in concentrated HCl (7 mL) at 40° C. for 72 h. The resulting slurry was filtered and the filter cake was dissolved in EtOAc and washed with saturated $NaHCO_3$ (aq) and brine. The organic layer was concentrated to give a solid which was recrystallized from $EtOAc/CH_2Cl_2$ to provide the title compound. LCMS (ESI, neg. ion): m/z=239 [M−H]$^-$; 479 [2M−H]$^-$. $^1$H NMR (500 MHz, $CD_3OD$): δ 7.10 (d, J=8.6 Hz, 4H), 6.70 (d, J=8.6 Hz, 4H), 2.65 (t, J=7.5 Hz, 4H), 1.93 (quint, J=7.5 Hz, 2H).

Step B: 4-[1-(4-Hydroxyphenyl)cyclobutyl]phenyl trifluoromethanesulfonate

To title compound from the previous step (3.88 g, 16.2 mmol) suspended in DCM was added pyridine (3.9 mL, 49 mmol). The mixture was cooled in an ice-water bath and trifluoromethanesulfonic anhydride (2.7 mL, 16 mmol) was added slowly via syringe. The resulting mixture was stirred at room temperature overnight. The reaction mixture was quenched by the addition of 2 N HCl, extracted with EtOAc, and the organic phase was concentrated in vacuo. The crude residue was purified by silica gel chromatography eluting with a gradient of 25% to 66% EtOAc/hexanes to provide the title compound as colorless oil. LCMS (ESI, neg. ion): m/z=371 [M−H]$^-$. $^1$H NMR (500 MHz, $CD_3OD$): δ 7.45 (d, J=8.9 Hz, 2H), 7.25 (d, J=8.7 Hz, 2H), 7.16 (d, J=8.7 Hz, 2H), 2.65 (t, J=7.5 Hz, 4H), 1.93 (quint, J=7.5 Hz, 2H).

Step C: Methyl 4-[1-(4-hydroxyphenyl)cyclobutyl]benzoate

To a solution of the title compound from the previous step (4.5 g, 12 mmol) in MeOH (8 mL) were added dichloro[1,1'-bis(diphenylphosphino)ferrocene]palladium(II), dichloromethane adduct (1.5 g, 1.8 mmol) and DIEA (8.3 mL, 48 mmol). The mixture was stirred under a CO atmosphere (balloon) at 50° C. for 16 h. The resulting mixture was passed through a fritted funnel and the filtrate was concentrated and purified by flash chromatography on silica gel eluting with a gradient of 12% to 80% EtOAc/hexanes to provide the title compound as a solid. LCMS (ESI, neg. ion): m/z=281.0 [M−H]$^-$. $^1$H NMR (500 MHz, $CD_3OD$): δ 7.91 (d, J=8.5 Hz, 2H), 7.39 (d, J=8.5 Hz, 2H), 7.15 (d, J=8.5 Hz, 2H), 3.86 (s, 3H), 2.77-2.66 (m, 4H), 2.00-1.87 (m, 2H).

INTERMEDIATE 2

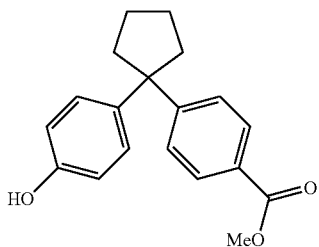

Methyl 4-[1-(4-hydroxyphenyl)cyclopentyl]benzoate

The title intermediate was prepared using procedures similar to those used for the synthesis of Intermediate 1. LCMS (ESI, neg. ion): m/z=295.2 [M−H]$^-$.

INTERMEDIATE 3

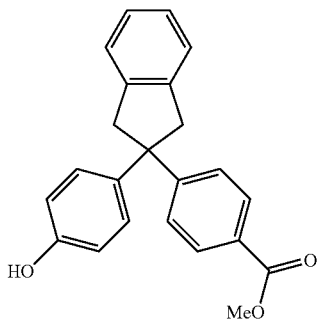

Methyl 4-[2-(4-hydroxyphenyl)-2,3-dihydro-1H-inden-2-yl]-benzoate

The title intermediate was prepared using procedures similar to those used for the synthesis of Intermediate 1. LCMS (ESI, neg. ion): m/z=343.1 [M−H]$^-$.

INTERMEDIATE 4

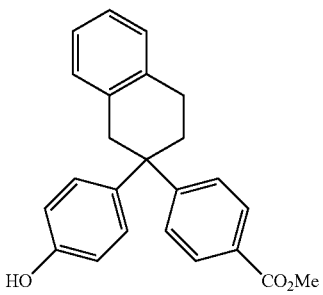

Methyl 4-[2-(4-hydroxyphenyl)-1,2,3,4-tetrahydronaphthalen-2-yl]benzoate The title intermediate was prepared using procedures similar to those used for the synthesis of Intermediate 1. LCMS (ESI, neg. ion): m/z=357.2 [M−H]$^-$.

INTERMEDIATE 5

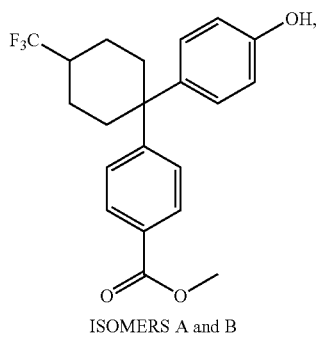

ISOMERS A and B

Method 1

Step A: 4,4'-[4-(Trifluoromethyl)cyclohexane-1,1-diyl]diphenol

A solution of 4-(trifluoromethyl)cyclohexanone (1.13 g, 6.8 mmol) and phenol (2.01 g, 21.4 mmol) in 3 mL of concentrated HCl (aq) was stirred at 40° C. for 18 h. The reaction mixture was diluted with EtOAc and saturated aqueous NaHCO$_3$ was slowly added. The organic layer was collected and the aqueous layer was extracted twice with EtOAc. The combined organic layers were concentrated under reduced pressure. The residue was purified by flash chromatography on silica gel eluting with a gradient of 0% to 40% EtOAc/hexanes over 10 column volumes, then 40% to 100% EtOAc/hexanes over 5 column volumes, affording the title compound as a white solid.

LCMS (ESI, neg. ion): m/z=335.1 [M−1]$^−$. $^1$H NMR (500 MHz, CD$_3$OD) δ 7.17 (d, J=8.7 Hz, 2H), 6.96 (d, J=8.7 Hz, 2H), 6.76 (d, J=8.7 Hz, 2H), 6.60 (d, J=9 Hz, 2H), 2.69 (d, J=13 Hz, 2H), 2.24 (m, 1H), 1.91 (t, 2H), 1.84 (br d, 2H), 1.49 (q, 2H).

Step B: 4-[1-[4-(Benzyloxy)phenyl]-4-(trifluoromethyl)cyclohexyl]phenol

To a solution of the title compound from the previous step (988 mg, 2.9 mmol) in 6 mL of DMF was added Cs$_2$CO$_3$ (945 mg, 2.9 mmol), then benzyl bromide (0.35 mL, 2.9 mmol). The reaction was allowed to stir at ambient temperature overnight, then partitioned between EtOAc and saturated aqueous NaHCO$_3$. The organic layer was collected and the aqueous layer was extracted twice with EtOAc. The combined organic layers were concentrated under reduced pressure. The residue was purified by flash chromatography on silica gel eluting with a gradient of 0%-35% EtOAc/hexanes over 10 column volumes, then 35%-100% EtOAc/hexanes over 5 column volumes to afford the title compound as a foamy white solid. LC-MS (ESI): m/z=449.18 [M+23]$^+$.

Step C: 4-[1-[4-(Benzyloxy)phenyl]-4-(trifluoromethyl)cyclohexyl]phenyl trifluoromethanesulfonate To a solution of the title compound from the previous step (432 mg, 1 mmol) and pyridine (0.40 mL, 5 mmol) in 5 mL of DCM was added dropwise trifluoromethanesulfonic anhydride (0.34 mL, 2 mmol). The reaction was allowed to stand at ambient temperature for 16 h, then diluted with DCM and poured into 2 N HCl. The organic layer was collected and the aqueous layer was washed twice with DCM. The combined organic layers were concentrated under reduced pressure. The residue was purified by flash chromatography on silica gel, eluting with a gradient of 0%-30% EtOAc/hexanes over 10 column volumes, then 30%-100% EtOAc/hexanes over 5 column volumes, affording the title compound as a yellow oil. LC-MS (ESI): 559.09 [M+1]$^+$.

Step D: Methyl 4-[1-[4-(benzyloxy)phenyl]-4-(trifluoromethyl)cyclohexyl]benzoate To a solution of the title compound from the previous reaction (194 mg, 0.35 mmol), palladium(II) acetate (11 mg, 0.05 mmol), and 1,1'-bis(diphenylphosphino)ferrocene (58 mg, 0.1 mmol) in 2.5 mL MeOH was added DIEA (0.24 mL, 1.4 mmol). The flask was heated under a CO atmosphere (balloon) at 50° C. for 16 h. The solvent was removed under reduced pressure and the resulting residue was purified by flash chromatography on silica gel eluting with a gradient of 0%-15% EtOAc/hexanes over 10 column volumes, affording the title compound as a foamy white solid. LC-MS (ESI): m/z=469.19 [M+1]$^+$.

Step E: Methyl 4-[1-(4-hydroxyphenyl)-4-(trifluoromethyl)cyclohexyl]benzoate, Isomers A and B To a solution of the title compound from the previous reaction (50 mg, 0.1 mmol) in 2.5 mL of MeOH and 2 mL of EtOAc was added a catalytic amount of 20% palladium hydroxide on carbon. The reaction was stirred under H$_2$ (balloon) for 5.5 h. The reaction was filtered through celite and the filter cake was washed with EtOAc and MeOH. The combined filtrate and washings were concentrated under reduced pressure to afford the product as a white solid.

The cis and trans isomers were separated by HPLC on a ChiralCel OJ column eluting with 10% EtOH/heptane, with Isomer A eluting as the faster moving compound and isomer B as the slower moving compound. Based on $^1$H NMR 2D NOE analysis, Isomer A is assigned with the trifluoromethyl and 4-hydroxyphenyl groups in a cis configuration and Isomer B is assigned with the trifluoromethyl and 4-hydroxyphenyl groups in a trans configuration.

Isomer A: LC-MS (ESI): m/z=379.26 [M+1]$^+$. $^1$H NMR (500 MHz, CD$_3$OD) δ 7.84 (d, J=8.5 Hz, 2H), 7.31 (d, J=8.5 Hz, 2H), 7.21 (d, J=8.9 Hz, 2H), 6.79 (d, J=8.7 Hz, 2H), 3.85 (s, 3H), 2.79 (d, J=12.8 Hz, 2H), 2.28 (m, 1H), 1.96 (t, 2H), 1.88 (d, 2H), 1.52 (q, 2H).

Isomer B: LC-MS (ESI): m/z=379.27 [M+1]$^+$. $^1$H NMR (500 MHz, CD$_3$OD) δ 7.98 (d, J=8.4 Hz, 2H), 7.52 (d, J=8.5 Hz, 2H), 7.01 (d, J=8.7 Hz, 2H), 6.63 (d, J=8.7 Hz, 2H), 3.89 (s, 3H), 2.86 (d, J=13.5H, 2H), 2.29 (m, 1H), 2.00-1.89 (overlapping t, d, 4H), 1.42 (q, 2H).

Method 2

Step A: 4-[1-(4-Hydroxyphenyl)-4-(trifluoromethyl)cyclohexyl]phenyl trifluoromethanesulfonate To a solution of the title compound of Intermediate 5, Method 1, Step A (1.1 g, 3.2 mmol) in 5 mL of DCM was added pyridine (0.39 mL, 4.8 mmol). After cooling to 0° C., trifluoromethanesulfonic anhydride (0.55 mL, 3.2 mmol) was added dropwise. After addition the reaction mixture was allowed to stir at ambient temperature for 2 h, then diluted with DCM and poured into 2 N HCl. The organic layer was collected and the aqueous layer was washed twice with DCM. The combined organic layers were dried over $Na_2SO_4$ and concentrated under reduced pressure. The resulting residue was purified by flash chromatography on silica gel eluting with a gradient of 0%-40% EtOAc/hexanes over 10 column volumes and 40%-100% EtOAc/hexanes over 5 column volumes to provide isomer A as the faster moving product and isomer B as the slower eluting product. The bis-triflate product was also isolated.

Isomer A: LC-MS (ESI): m/z=468.06 [M+1]$^+$. $^1$H NMR (500 MHz, $CD_3OD$): δ 7.33 (d, J=8.9 Hz, 2H), 7.21 (d, J=8.7 Hz, 2H), 7.17 (d, J=9 Hz, 2H), 6.80 (d, J=8.7 Hz, 2H), 2.77 (d, J=12.8 Hz, 2H), 2.28 (m, 1H), 1.96 (t, 2H), 1.89 (br d, 2H), 1.52 (q, 2H).

Isomer B: $^1$H NMR (500 MHz, $CD_3OD$): δ 7.53 (d, J=8.9 Hz, 2H), 7.31 (d, J=8.9 Hz, 2H), 7.00 (d, J=8.7 Hz, 2H), 6.65 (d, J=8.7 Hz, 2H), 2.80 (d, J=13.3 Hz, 2H), 2.28 (m, 1H), 1.97 (t, 2H), 1.90 (br d, 2H), 1.41 (q, 2H).

bis-triflate: LC-MS (ESI): m/z=617.23. [M+1]$^+$. $^1$H NMR (500 MHz, $CD_3OD$): δ 7.63 (d, J=8.9 Hz, 2H), 7.40 (overlapping d, d, 4H), 7.26 (d, J=9.0 Hz, 2H), 2.91 (br d, J=13 Hz, 2H), 2.36 (m, 1H), 2.06 (t, 2H), 1.97 (br d, 2H), 1.46 (q, 2H).

Step B: Methyl 4-[1-(4-hydroxyphenyl)-4-(trifluoromethyl)cyclohexyl]benzoate, Isomer B To isomer B from the previous reaction (1.1 g, 2.4 mmol) in 7 mL of MeOH was added dichloro[1,1'-bis(diphenylphosphino)ferrocene]palladium(II), dichloromethane adduct (259 mg, 0.35 mmol) and DIEA (1.7 mL, 9.6 mmol). The reaction was stirred under a CO atmosphere (balloon) at 60° C. overnight. The reaction mixture was filtered over celite and the filter cake was washed with MeOH. The combined filtrate and washings were concentrated under reduced pressure. The resulting residue was purified on silica, eluting with a gradient of 0%-40% EtOAc/hexanes over 10 column volumes and 40%-100% EtOAc/hexanes over 5 column volumes, affording the title compound as a white solid. LCMS and NMR data for the title compound are consistent with Intermediate 5 Isomer B prepared using Method 1.

INTERMEDIATE 6

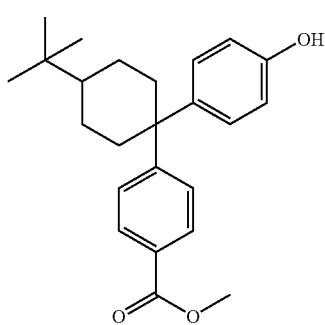

Methyl 4-[4-tert-butyl-1-(4-hydroxyphenyl)cyclohexyl]benzoate

The title intermediate was prepared from 4-tert-butylcyclohexanone using procedures similar to those described for Intermediate 5, Method 1. LC-MS (ESI): m/z=367.3 [M+1]$^+$.

INTERMEDIATE 7

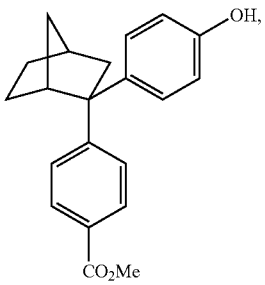

ENANTIOMERS A and B

Step A: Methyl 4-(2-hydroxybicyclo[2.2.1]hept-2-yl)benzoate

A solution of methyl 4-iodobenzoate (23.1 g, 0.0882 mol) dissolved in anhydrous THF (200 mL) was cooled to −47° C. Isopropyl magnesium chloride (48 mL of a 2.0 M solution in THF, 0.097 mol) was slowly added to the solution. The reaction mixture was stirred at −47° C. for 1 h, then cannulated into a pre-cooled solution of norcamphor (11.6 g, 0.105 mol) in THF (100 mL) at −47° C. The reaction mixture was subsequently stirred at −40° C. overnight, and was then allowed to warm to −20° C. Saturated aqueous ammonium chloride was added. EtOAc was used to extract three times. The combined organic portion was washed with water and brine, dried ($MgSO_4$), filtered, concentrated, and purified by flash chromatography on silica gel (gradient elution; 0%-30% EtOAc/hexanes as eluent) to afford the title compound.

Step B: Methyl 4[2-(4-hydroxyphenyl)bicyclo[2.2.1]hept-2-yl]benzoate

A mixture of phenol (7.80 g, 82.8 mmol) and p-toluenesulfonic acid (2.48 g, 13.0 mmol) in anhydrous toluene (160 mL) was refluxed for 10 min in a 2-neck round bottom flask equipped with a Dean-Stark apparatus. A solution of the title compound from the previous reaction (10.2 g, 41.4 mmol) in toluene (40 mL) was added into the system through an addition funnel over 10 min. The resultant mixture was stirred at reflux for 14 h, then cooled to ambient temperature. The reaction was diluted with EtOAc, washed successively with aqueous sodium hydroxide (1N), water, and brine, dried ($MgSO_4$), filtered, concentrated, and purified by flash chromatography on silica gel (gradient elution; 0%-20% EtOAc/hexanes) to afford the title compound.

Step C: Chiral resolution of methyl 4[2-(4-hydroxyphenyl)bicyclo[2.2.1]hept-2-yl]benzoate The title compound of the previous reaction was resolved into its enantiomeric components by preparative chiral HPLC (Chiralpak AD column, 15% EtOH/heptane as eluent) to provide in order of elution:

Enantiomer A, (+) CD deflection, retention time=9.18 min on analytical Chiralpak AD column (4.6×250 mm; 10 micron, flow rate=1 mL/min, λ=220 ran UV detection);

Enantiomer B, (−) CD deflection, retention time=14.95 min on analytical Chiralpak AD column (4.6×250 mm; 10 micron, flow rate=1 mL/min, λ=220 nm UV detection).

Enantiomer B: $^1$H NMR (500 MHz, $CDCl_3$): δ 9.15 (s, 1H); 7.80 (d, J=8.5 Hz, 2H); 7.43 (d, J=8.5 Hz, 2H); 7.14 (d, J=8.7 Hz, 2H); 6.61 (d, J=8.7 Hz, 2H); 3.79 (s, 3H); 3.29 (s, 1H); 2.18-2.34 (overlapping m, 3H); 1.51 (d, J=9.4 Hz, 1H); 1.44 (m, 2H); 1.29 (d, J=9.1 Hz, 1H); 1.05 (m, 2H).

Absolute stereochemical assignments of Enantiomers A and B were established by x-ray crystallography, with Enantiomer A assigned as 1S, 2S, 4R and Enantiomer B as 1R, 2R, 4S.

INTERMEDIATE 8

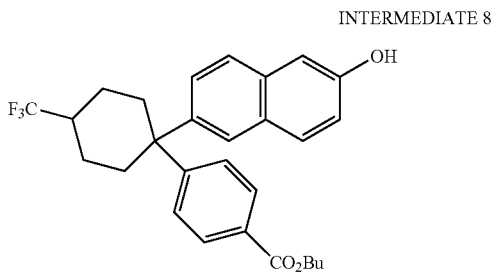

Step A: 1-(6-Methoxy-2-naphthyl)-4-(trifluoromethyl)cyclohexanol, Isomers A and B To a cold (−78° C.) anhydrous solution of 2-methoxy-6-bromonaphthalene (1.52 g, 6.40 mmol) in THF (40 mL) was added n-BuLi (6.9 mL of a 2.5 M solution in hexanes, 6.9 mmol). The mixture was stirred at −78° C. under a nitrogen atmosphere for 15 min, then 4-(trifluoromethyl)cyclohexanone (0.88 g, 5.3 mmol) was added slowly to the reaction mixture. The bath was allowed to warm to room temperature and the reaction mixture was quenched with saturated NH$_4$Cl (aq). The resultant mixture was extracted with EtOAc/hexanes. The organic layer was evaporated in vacuo and the crude residue was purified by flash chromatography on silica gel using gradient elution (0% to 20% EtOAc/hexanes, 150 mL; 20% to 35% EtOAc/hexanes, 204 mL; 35% to 75% EtOAc/hexanes, 381 mL) to provide Isomer A as the faster-eluting product and Isomer B as the slower-eluting product.

Isomer A: $^1$H NMR (500 MHz, CDCl$_3$): δ 7.89 (s, 1H), 7.80 (t, J=9.4 Hz, 2H), 7.64 (d, J=8.7 Hz, 1H), 7.21 (d, J=8.9 Hz, 1H), 7.17 (s, 1H), 3.96 (s, 3H), 2.64-2.52 (m, 2H), 2.37-2.24 (m, 1H), 2.15-2.02 (m, 2H), 1.91-1.80 (m, 2H), 1.69-1.51 (m, 2H).

Isomer B: $^1$H NMR (500 MHz, CDCl$_3$): δ 7.89 (s, 1H), 7.80 (t, J=9.4 Hz, 2H), 7.64 (d, J=8.7 Hz, 1H), 7.21 (d, J=8.9 Hz, 1H), 7.17 (s, 1H), 3.96 (s, 3H), 2.64-2.52 (m, 2H), 2.37-2.24 (m, 1H), 2.15-2.02 (m, 2H), 1.91-1.80 (m, 2H), 1.69-1.51 (m, 2H).

Step B: 4-[1-(6-Methoxy-2-naphthyl)-4-(trifluoromethyl)cyclohexyl]phenol, Isomers A and B Isomer A from the previous step (200 mg, 0.61 mmol) and phenol (200 mg, 2.12 mmol) were combined in a 4 mL vial and heated until molten. para-Toluenesulfonic anhydride (80 mg, 0.42 mmol) was then added and the mixture was stirred at 105° C. for 30 min. The reaction mixture was allowed to cool to room temperature and diluted with saturated NaHCO$_3$ (aq). The resultant slurry containing a ca. 1:1 mixture of cis and trans product isomers was extracted with EtOAc. The organic layer was concentrated in vacuo and the residue was purified by flash chromatography on silica gel eluting with a gradient of 20% to 25% EtOAc/hexanes to provide Isomer A as the faster eluting isomer and Isomer B as the slower eluting isomer.

Isomer A: LCMS (ESI): m/z=401.3 [M+H]$^+$. $^1$H NMR (500 MHz, CDCl$_3$): δ 7.69 (d, J=8.92, 1 H), 7.60 (d, J=8.7 Hz, 2H), 7.30-7.23 (m, 3H), 7.13-7.07 (m, 2H), 6.84 (d, J=8.7, 1H), 3.90 (s, 3H), 2.87 (d, J=13.2, 2H), 2.30-2.18 (m, 1H), 2.08-1.92 (m, 4H), 1.64-1.52 (m, 2H).

Isomer B: LCMS (ESI): m/z=401.3 [M+H]$^+$. $^1$H NMR (500 MHz, CDCl$_3$): δ 7.81 (d, J=1.6 Hz, 1H), 7.78 (d, J=8.9 Hz, 1H), 7.72 (d, J=8.7 Hz, 1H), 7.35 (d, J=8.7 Hz, 1H), 7.20 (d, J=8.9 Hz, 1H), 7.15 (d, J=2.3 Hz, 1H), 7.09 (d, J=8.9, 2H), 6.72 (d, J=8.9 Hz, 2H), 3.97 (s, 3H), 2.89 (d, J=13.3, 2H), 2.27-2.16 (m, 1H), 2.07-1.93 (m, 4H), 1.74-1.54 (m, 2H).

Step C: Butyl 4-[1-(6-methoxy-2-naphthyl)-4-(trifluoromethyl)cyclohexyl]benzoate To a solution of Isomer A from the previous reaction (498 mg, 1.24 mmol) in anhydrous CH$_2$Cl$_2$ (14 mL) were added pyridine (0.15 mL, 1.86 mmol) followed by trifluoromethanesulfonic anhydride (1.38 g, 4.89 mmol). The mixture was stirred at room temperature for 20 min, quenched with water, and the resultant mixture was extracted with EtOAc/hexanes. The organic phase was washed with 1N HCl, then passed through a short silica plug. The filtrate was concentrated to dryness to give the crude triflate as a solid. The triflate was taken up in H-butanol (8 mL) and dichloro[1,1'-bis(diphenylphosphino)ferrocene]palladium(II), dichloromethane adduct (86 mg, 0.12 mmol) and DIEA (0.61 mL, 3.5 mmol) were added. The reaction mixture was stirred at 90° C. under an atmosphere of CO (balloon) for 1 hour. The resulting mixture was concentrated and purified by flash chromatography on silica gel eluting with a gradient of 25% to 65% EtOAc/hexanes to provide the title compound as solid.

LCMS (ESI): m/z=485.4 [M+H]$^+$. $^1$H NMR (500 MHz, CDCl$_3$): δ 7.90 (d, J=8.7 Hz, 2H), 7.80 (d, J=1.6 Hz, 1H), 7.76 (d, J=8.9 Hz, 1H), 7.70 (d, J=8.7 Hz, 1H), 7.33-7.27 (m, 3H), 7.19 (dd, J=8.9, 2.5 Hz, 1H), 7.13 (d, J=2.3 Hz, 1H), 4.29 (t, J=6.5 Hz, 2H), 3.94 (s, 3H), 2.93 (d, J=13.0 Hz, 2H), 2.28-2.15 (m, 1H), 2.10-1.94 (m, 4H), 1.78-1.57 (m, 4H), 1.52-1.41 (m, 2H), 0.96 (t, J=7.60 Hz, 3H).

Step D: Butyl 4-[1-(6-hydroxy-2-naphthyl-4-(trifluoromethyl)cyclohexyl]benzoate To a cold (0° C.) solution of the title compound from the previous step (460 mg, 0.95 mmol) in anhydrous CH$_2$Cl$_2$ (10 mL) was slowly added BBr$_3$ (3 mL of a 1.0 M solution in CH$_2$Cl$_2$, 3.0 mmol) via syringe under nitrogen. The mixture was stirred at 0° C. for 2 h. The reaction was quenched with water and the resultant mixture was extracted with EtOAc/hexanes. The organic layer was concentrated in vacuo to give the title compound as solid. LC-MS (ESI): m/z=471.3 [M+H]$^+$. $^1$H NMR (500 MHz, CDCl$_3$): δ 8.05 (d, J=8.5 Hz, 2H), 7.73-7.53 (m, 3H), 7.51 (d, J=8.5 Hz, 2H), 7.23-7.06 (m, 3H), 4.35 (t, J=6.6 Hz, 2H), 2.95 (d, J=12.4 Hz, 2H), 2.30-2.16 (m, 1H), 2.15-1.88 (m, 4H), 1.84-1.69 (m, 2H), 1.68-1.42 (m, 4H), 1.01 (t, J=7.32 Hz, 3H).

INTERMEDIATE 9

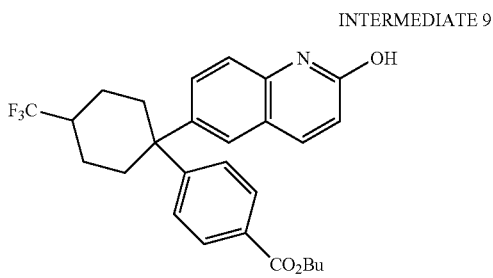

Step A: 1-(2-Methoxyquinolin-6-yl-4-(trifluoromethyl)cyclohexanol

To a cold (−78° C.) anhydrous THF solution of 2-methoxy-6-bromoquinoline (1.16 g, 4.89 mmol) was added w-BuLi (2.05 mL of a 2.5 M solution in hexane, 5.13 mmol). The mixture was stirred at −78° C. under a nitrogen atmosphere for 15 min and 4-(trifluoromethyl)cyclohexanone (0.81 g, 4.89 mmol) was added slowly to the reaction. After addition was complete, the bath was allowed to warm to room temperature. The reaction mixture was quenched with saturated NH$_4$Cl (aq) and extracted with EtOAc/hexanes. The organic layer was dried over Na$_2$SO$_4$ and evaporated in vacuo and the resultant residue was purified by flash chromatography on silica gel using gradient elution (0% to 20% EtOAc/hexanes, 150 mL; 20% to 35% EtOAc/hexanes, 204 mL; 35% to 75% EtOAc/hexanes, 381 mL) to provide Isomer A as the faster-moving isomer and Isomer B as the slower-moving isomer.

Isomer A: LCMS (ESI): m/z=326.1 [M+H]$^+$. $^1$H NMR (500 MHz, CDCl$_3$): δ 7.99 (d, J=8.9 Hz, 1H), 7.87 (d, J=8.7 Hz, 1H), 7.83 (d, J=2.1 Hz, 1H), 7.75 (dd, J=8.7, 2.1 Hz, 1H), 6.93 (d, J=8.7 Hz, 1H), 4.10 (s, 3H), 2.21-2.12 (m, 1H), 2.05-1.91 (m, 8H).

Isomer B: LCMS (ESI): m/z=326.2 [M+H]$^+$. $^1$H NMR (500 MHz, CDCl$_3$): δ 7.99 (d, J=8.7 Hz, 1H), 7.89 (d, J=8.7 Hz, 1H), 7.82-7.76 (m, 2H), 6.94 (d, J=8.7 Hz, 1H), 4.10 (s, 3H), 2.58-2.49 (m, 2H), 2.36-2.24 (m, 1H), 2.13-2.03 (m, 2H), 1.89-1.78 (m, 2H), 1.67-1.57 (m, 2H).

Step B: 4-[1-(2-Methoxyquinolin-6-yl)-4-(trifluoromethyl)cyclohexyl]phenol, Isomer A To phenol (0.46 g, 4.9 mmol) dissolved in trifluoromethanesulfonic acid (3 mL) was added Isomer A from the previous step (1.06 g, 3.26 mmol). The mixture was stirred at room temperature for 16 h, then transferred to an ice/water bath and quenched by slow addition of saturated aqueous NaHCO$_3$. The resulting mixture containing two product isomers was extracted with EtOAc. The organic phase was evaporated in vacuo to provide a solid residue which was triturated with toluene/DCM (1:3 v/v). The slurry was filtered through a fritted funnel and the filter cake was washed with DCM (2×) and toluene (2×). Isomer A, which provided the more potent glucagon receptor antagonists I, remained in the filter cake while Isomer B passed into the filtrate. Isomer A was dissolved in EtOAc and washed with 1 N HCl (aq) and brine. The organic phase was concentrated to provide title Isomer A as a white solid. LCMS (ESI): m/z 402.2 [M+H]$^+$.

Step C: Butyl 4-[1-(2-methoxyquinolin-6-yl)-4-(trifluoromethyl)cyclohexyl]benzoate To a solution of Isomer A from the previous step (800 mg, 1.99 mmol) in anhydrous CH$_2$Cl$_2$ (10 mL) were added pyridine (0.24 mL, 3.0 mmol) and trifluoromethanesulfonic anhydride (0.40 mL, 2.4 mmol). The mixture was stirred at room temperature for 20 min, then quenched with water and extracted with EtOAc/hexanes. The combined organic phase was washed with H$_2$O (2×), then brine. The organic phase was dried over Na$_2$SO$_4$ and passed through a short silica plug. The eluent was concentrated to dryness to give the crude triflate. A portion of the triflate (875 mg, 1.64 mmol) was taken up in n-butanol (12 mL) and PdCl$_2$(dppf), dichloromethane adduct (120 mg, 0.1 mmol) and DIEA (0.86 mL, 3 mmol) were added. The resulting slurry was stirred at 90° C. under a CO atmosphere (balloon) for 1 h. The reaction mixture was concentrated and purified by flash chromatography on silica gel eluting with a gradient of 16% to 50% EtOAc/hexanes to provide the title compound. LCMS (ESI): m/z=486.2 [M+H]$^+$. $^1$H NMR (500 MHz, CDCl$_3$): δ 8.07 (d, J=8.5 Hz, 2H), 7.92 (d, J=8.9 Hz, 1H), 7.74 (d, J=8.9 Hz, 1H), 7.54-7.49 (m, 3H), 7.44 (dd, J=8.9, 2.3 Hz, 1H), 6.91 (d, J=8.9 Hz, 1H), 4.36 (t, J=6.6 Hz, 2H), 4.07 (s, 3H), 2.95 (d, J=13.4 Hz, 2H), 2.3-2.19 (m, 1H), 2.15-1.97 (m, 4H), 1.79 (quint, J=6.6 Hz, 2H), 1.66-1.47 (m, 4H), 1.02 (t, J=7.3 Hz, 3H).

Step D: Butyl 4-[1-(2-hydroxyoxyquinolin-6-yl)-4-(trifluoromethyl)cyclohexyl]benzoate To a stirring solution of the title compound from the previous step (490 mg, 1.0 mmol) in anhydrous dichloroethane (5 mL) was slowly added trimethylsilyl iodide (0.82 mL, 5.7 mmol). The mixture was stirred at 65° C. for 3.5 h, then the reaction mixture was concentrated in vacuo. The residue was reconcentrated in vacuo first from toluene (20 mL), then from a mixture of 2-propanol (6 mL) and toluene (10 mL) to provide the title compound. LC-MS (ESI): m/z=472.2 [M+1]$^+$. $^1$H NMR (500 MHz, CDCl$_3$): δ 8.08 (d, J=8.2 Hz, 3H), 7.63-7.50 (m, 3H), 7.49 (d, J=8.2 Hz, 2H), 6.94 (d, J=9.4 Hz, 1H), 4.36 (t, J=6.6 Hz, 2H), 2.92 (d, J=13.0 Hz, 2H), 2.31-2.18 (m, 1H), 2.15-1.97 (m, 4H), 1.83-1.71 (m, 2H), 1.65-1.46 (m, 4H), 1.01 (t, J=7.3 Hz, 3H).

INTERMEDIATE 10

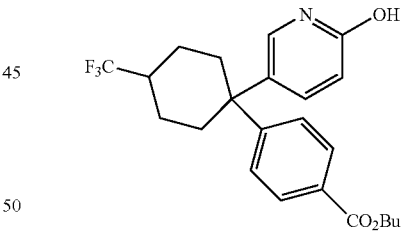

Step A: 1-(6-Methoxypyridin-3-yl)-4-(trifluoromethyl)cyclohexanol n-Butyllithium (3 mL of a 2.5 M solution in hexanes, 7.5 mmol) was added dropwise to 5-bromo-2-methoxy pyridine (6.0 mmol, 0.78 mL) in 40 mL of THF cooled in a dry ice/acetone bath. After aging for 15 min, 4-trifluoromethyl-cyclohexanone (6.0 mmol, 1 g) was added and the reaction mixture was allowed to slowly warm to 0° C. over 2 h. The reaction was cooled in a dry ice/acetone bath and the reaction was quenched by addition of sat. ammonium chloride (aq), then saturated sodium bicarbonate (aq). The reaction mixture was extracted with hexanes/EtOAc. The organic phase was concentrated and the resultant residue was purified by flash chromatography on silica gel using a step gradient of 4:1, 2:1 and 1:1 (v/v) EtOAc/hexanes to give the title compound as a mixture of isomers. LC-MS (ESI): m/z=276.2 [M+1]$^+$.

Step B: 4-[1-(6-Methoxypyridin-3-yl)-4-(trifluoromethyl)cyclohexyl]phenol

To solution of phenol (680 mg, 7.2 mmol) in 3 mL of trifluoromethanesulfonic acid was added the title compound of the previous step (1.15 g, 4.2 mmol). The reaction was slightly exothermic and the mixture was cooled in an acetone bath. After 1.5 h, the reaction mixture was poured into saturated sodium bicarbonate (aq) and extracted with twice with EtOAc. The organic phase was concentrated and the resultant residue was purified by flash chromatography on silica gel eluting with a gradient of 10% to 20% EtOAc/hexanes to give the title compound as a mixture of two isomers. LC-MS (ESI): m/z=352.3 [M+1]$^+$.

Step C: Butyl 4-[1-(6-methoxypyridin-3-yl)-4-(trifluoromethyl)cyclohexyl]benzoate To the title compound of the previous reaction (1.3 g, 3.6 mmol) and pyridine (0.42 mL, 5.2 mmol) in 30 mL of dichloromethane was added dropwise trifluoromethanesulfonic anhydride (0.65 mL, 3.9 mmol). The reaction mixture was partitioned between aqueous sodium bicarbonate/hexanes-EtOAc. The organic phase was separated, washed with water, dried over sodium sulfate, then passed through a plug of silica gel and concentrated. The crude triflate was taken up in 20 mL of n-butanol, and PdCl$_2$(dppf), dichloromethane adduct (250 mg, 0.3 mmol) and DIEA (0.9 mL, 5.2 mmol) were added. The reaction was stirred at 90° C. under CO (balloon) for 2 h and the reaction was concentrated in vacuo. Flash chromatography on silica gel eluting with 15% EtOAc/hexanes provided the title compound as a mixture of two isomers. LC-MS (ESI): m/z=436.4 [M+1]$^+$.

Step D: Butyl 4-[1-(6-hydroxypyridin-3-yl)-4-(trifluoromethyl)cyclohexyl]benzoate To a solution of the title compound from the previous step (1.4 g, 3.3 mmol) in dichloroethane (12 mL) was added 2 mL of trimethylsilyl iodide. The reaction mixture was heated at 55° C. for 6 h. The solvent was removed in vacuo. The residue was concentrated first from toluene, then from a mixture of toluene/isopropyl alcohol. Flash chromatography on silica gel eluting with a gradient of 33% to 50% EtOAc/hexanes provided Isomer A as the faster-eluting compound and Isomer B as the slower-eluting compound.

Isomer A: $^1$H NMR (500 MHz, CD$_2$Cl$_2$): δ (ppm) 7.95 (d, J=8.5 Hz, 2H), 7.81 (s, 1H), 7.33 (d, J=8.5 Hz, 2H), 6.73 (d, J=9.2 Hz, 1H), 4.29 (t, J=6.5 Hz, 2H), 2.65 (d, J=13.0 Hz, 2H), 2.25 (m, 1H), 1.74 (m, 2H), 0.98 (t, J=7.4 Hz, 3H).

Isomer B: $^1$H NMR (500 MHz, CD$_2$Cl$_2$): δ (ppm) 8.06 (d, J=8.2 Hz, 2H), 7.64 (d, J=2.3 Hz, 1H), 7.48 (m, 3H), 6.67 (d, J=9.4 Hz, 1H), 4.33 (t, J=6.6 Hz, 2H), 2.79 (d, J=13.0 Hz, 2H), 2.25 (m, 1H), 1.77 (m, 2H), 1.00 (t, J=7.4 Hz, 3H).

EXAMPLE 1

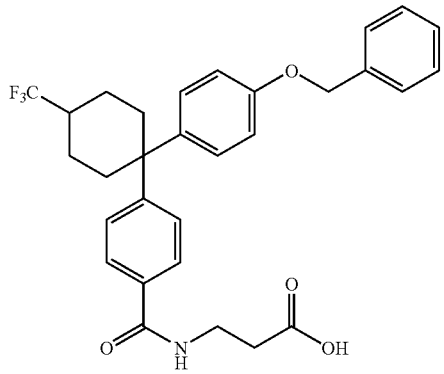

Step A: 4-[1-[4-(Benzyloxy)phenyl]-4-(trifluoromethyl)cyclohexyl]benzoic acid

To the title compound of Intermediate 5, Method 1, Step D (11.5 mg, 0.02 mmol) in 1 mL of dioxane was added a solution of LiOH (7 mg, 0.3 mmol) in 0.5 mL of water. The reaction was stirred at room temperature for 16 h. The reaction mixture was taken up in aqueous pH 7 buffer and extracted with EtOAc. The organic layer was collected and the aqueous layer was washed twice with EtOAc. The combined organic phase was concentrated under reduced pressure. LC-MS (ESI): m/z=455.2 [M+1]$^+$.

Step B: 3-({4-[1-[4-(Benzyloxy)phenyl]-4-(trifluoromethyl)cyclohexyl]benzoyl}amino)propanoic acid To a solution of the title compound of the previous step (5.9 mg, 0.012 mmol), β-alanine tert-butyl ester hydrochloride (5 mg, 0.03 mmol), HOBt (5 mg, 0.03 mmol) and EDC (6 mg, 0.03 mmol) in 0.5 mL of DMF was added DIEA (0.007 mL, 0.04 mmol). The reaction was heated to 45° C. for 1 h, then partitioned between EtOAc/water. The organic layer was collected and the aqueous layer was washed twice with EtOAc. The combined organic phase was concentrated under reduced pressure. LC-MS (ESI): m/z=582.3 [M+1]$^+$.

The resultant residue was dissolved in 1 mL of DCM containing 0.015 mL of water and 0.60 mL of trifluoroacetic acid was added. The reaction was stirred at room temperature for 50 min. The solvent was removed and the residue was purified by reverse-phase chromatography (35%-100% MeCN/H$_2$O, both containing 0.1% TFA) to provide the title compound as a 1.6:1 mixture of stereoisomers. LC-MS (ESI): m/z=526.1 [M+1]$^+$.

Major isomer: $^1$H NMR (500 MHz, CD$_3$OD): δ 7.65 (d, J=8.4 Hz, 2H), 7.48 (d, J=7.6 Hz, 2H), 7.39-7.29 (overlapping m, 3H), 7.33 (d, J=8.9 Hz, 2H), 7.30 (d, J=8.5 Hz, 2H), 7.01 (d, J=8.9 Hz, 2H), 5.08 (s, 2H), 3.59 (t, 2H), 2.83 (br d, J=13 Hz, 2H), 2.61 (t, 2H), 2.30 (m, 1H), 1.99 (t, 2H), 1.91 (br d, 2H), 1.53 (q, 2H). Minor isomer: δ 7.78 (d, J=8.5 Hz, 2H), 7.51 (d, J=8.7 Hz, 2H), 7.39-7.29 (overlapping m, 5H), 7.12 (d, J=8.9 Hz, 2H), 6.84 (d, J=9 Hz, 2H), 5.01 (s, 2H), 3.63 (t, 2H), 2.87 (br d, J=14 Hz, 2H), 2.64 (t, 2H), 2.30 (m, 1H), 1.99 (t, 2H), 1.91 (br d, 2H), 1.48 (q, 2H).

EXAMPLE 2

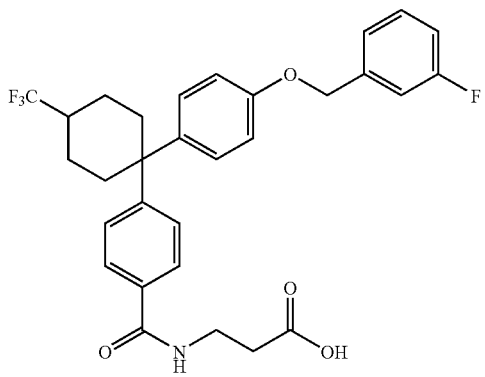

Step A: Methyl 4-[1-{4-[(3-fluorobenzyl)oxy]phenyl}-4-(trifluoromethyl)cyclohexyl]-benzoate To a solution of Intermediate 5, Isomer B (20 mg, 0.05 mmol) in 1 mL of DMF was added $Cs_2CO_3$ (58 mg, 0.15 mmol) and 3-fluorobenzyl bromide (0.019 mL, 0.15 mmol). The reaction mixture was stirred at 40° C. for 2 h, then at ambient temperature for 16 h. The reaction was partitioned between EtOAc and saturated aqueous $NaHCO_3$. The organic layer was collected and the aqueous layer was washed twice with EtOAc. The combined organic layers were concentrated under reduced pressure. LC-MS (ESI): m/z=487.3 $[M+1]^+$.

Step B: 4-[1-{4-[(3-Fluorobenzyl)oxy]phenyl}-4-(trifluoromethyl)cyclohexyl]benzoic acid To the title compound from the previous step (0.05 mmol) in 1 mL of dioxane was added a solution of LiOH (10 mg, 0.41 mmol) in 0.5 mL of water. The reaction was stirred at 40° C. for 2 h and at room temperature for 16 h. The reaction mixture was partitioned between aqueous pH 7 buffer and EtOAc. The organic layer was collected and the aqueous layer was washed twice with EtOAc. The combined organic layers were dried over $Na_2SO_4$ and concentrated under reduced pressure to provide the title compound as a white solid. LC-MS (ESI): m/z=473.3 $[M+1]^+$.

Step C: 3-({4-[1-{4-[(3-Fluorobenzyl)oxy]phenyl}-4-(trifluoromethyl)cyclohexyl]benzoyl}amino)propanoic acid To a solution of the title compound from the previous step (35 mg, 0.05 mmol), β-alanine ethyl ester hydrochloride (18 mg, 0.1 mmol), HOBt (15 mg, 0.1 mmol) and EDC (19 mg, 0.1 mmol) in 1 mL of DMF was added DIEA (0.026 mL, 0.15 mmol). The reaction mixture was heated to 40° C. for 2 h, then partitioned between EtOAc/brine. The organic layer was collected and the aqueous layer was washed twice with EtOAc. The combined organic layers were concentrated under reduced pressure to provide the crude ester. LC-MS (ESI): m/z=600.4 $[M+1]^+$.

The resultant residue was dissolved in 0.70 mL of DCM with 0.015 mL of water and 0.50 mL of trifluoroacetic acid. The reaction mixture was stirred at room temperature for 1 h. The solvent was removed under reduced pressure and the product was purified by reverse-phase chromatography (50-100% MeCN/$H_2O$, both containing 0.1% TFA). Lyophilization provided the title compound as a white solid.

LC-MS (ESI): m/z=544.3 $[M+1]^+$. $^1$H NMR (500 MHz, $CD_3OD$): δ 7.77 (d, J=8.5 Hz, 2H), 7.50 (d, J=8.5 Hz, 2H), 7.35 (m, 1H), 7.19 (d, J=7.8 Hz, 1H), 7.12 (overlapping d, m, 3H), 7.00 (t, 1H), 6.83 (d, J=8.9 Hz, 2H), 5.02 (s, 2H), 3.62 (t, 2H), 2.86 (d, J=13.3 Hz, 2H), 2.63 (t, 2H), 2.29 (m, 1H), 1.98 (t, 2H), 1.91 (br d, 2H), 1.44 (q, 2H).

EXAMPLE 3

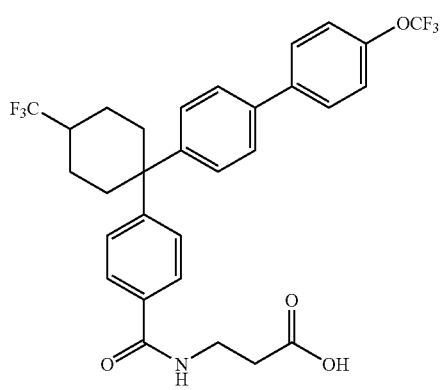

Step A: Methyl 4-[4-(trifluoromethyl)-1-(4-{[(trifluoromethyl)sulfonyl]oxy}phenyl)cyclohexyl]benzoate To a solution of Intermediate 5, Isomer B (120 mg, 0.32 mmol) and pyridine (0.13 mL, 1.6 mmol) in 2 mL of DCM was added trifluoromethanesulfonic anhydride (0.11 mL, 0.63 mmol). The reaction mixture was allowed to stand at ambient temperature for 1 h, then diluted with DCM and poured into 2 N HCl. The organic layer was collected and the aqueous layer was washed twice with DCM. The combined organic layers were dried over $Na_2SO_4$ and concentrated under reduced pressure to provide the title compound as a yellow solid. LC-MS (ESI): m/z=511.2 $[M+1]^+$. $^1$H NMR (500 MHz, $CD_3OD$): δ 8.02 (d, J=8.5 Hz, 2H), 7.57 (d, J=8.7 Hz, 2H), 7.39 (d, J=9.1 Hz, 2H), 7.22 (d, J=9 Hz, 2H), 3.89 (s, 3H), 2.93 (d, J=13.1 Hz, 2H), 2.33 (m, 1H), 2.03 (t, 2H), 1.94 (br d, 2H), 1.45 (q, 2H).

Step B: 4-[1-[4'-(Trifluoromethoxy)biphenyl-4-yl]-4-(trifluoromethyl)cyclohexyl]benzoic acid To a mixture of the title compound from the previous step (8 mg, 0.016 mmol), 4-(trifluoromethoxy)benzeneboronic acid (4.8 mg, 0.024 mmol) and tetrakis(triphenyl-phosphine)palladium(0) (1.8 mg, 0.0016 mmol) was added 0.40 mL of ethylene glycol dimethyl ether, 0.20 mL of ethanol and 0.20 mL of 2M sodium carbonate (aq). The reaction mixture was heated in a CEM Discover microwave reactor at 150° C. for 10 min. The reaction mixture was partitioned between DCM and saturated aqueous $NaHCO_3$. The organic layer was collected and the aqueous layer was washed twice with DCM. The combined organic phase was concentrated under reduced pressure then purified by reverse phase chromatography (65%-100% MeCN/water, both containing 0.1% TFA) to provide the title compound. LC-MS (ESI): m/z=509.3 $[M+1]^+$.

Step C: tert-Butyl 3-({4-[1-[4'-trifluoromethoxy) biphenyl-4-yl]-4-(trifluoromethyl)cyclohexyl] benzoyl}amino)propanoate To a solution of the title compound from the previous step (25 mg, 0.05 mmol), β-alanine tert-butyl ester hydrochloride (24 mg, 0.13 mmol), HOBt (20 mg, 0.13 mmol) and EDC (25 mg, 0.13 mmol) in 1 mL of DMF was added DIEA (0.035 mL, 0.2 mmol). The reaction mixture was heated at 40° C. for 1.5 h, then partitioned between EtOAc/brine. The organic layer was collected and the aqueous layer was washed twice with EtOAc. The combined organic layers were dried over $Na_2SO_4$ and concentrated under reduced pressure to afford the title compound as an amber oil. LC-MS (ESI): m/z=636.4 $[M+1]^+$.

Step D: 3-({-4-[1-[4'-(trifluoromethoxy)biphenyl-4-yl]-4-(trifluoromethyl)cyclohexyl]benzoyl}amino) propanoic acid The title compound from the previous step (0.05 mmol) was taken up in 0.70 mL of DCM and 0.015 mL of water with 0.50 mL of trifluoroacetic acid. The reaction was stirred at room temperature for 1 h. The reaction was concentrated in vacuo and the residue was purified by reverse phase chromatography (60%-100% MeCN/$H_2O$, both containing 0.1% TFA). Lyophilization afforded the title compound as a white solid. LC-MS (ESI): m/z=580.3 $[M+1]^+$. $^1$H NMR (500 MHz, $CD_3OD$): δ 7.80 (d, J=8.5 Hz, 2H), 7.63 (d, J=8.7 Hz, 2H), 7.56 (d, J=8.5 Hz, 2H), 7.49 (d, J=8.4 Hz, 2H), 7.32-7.29 (overlapping d, d, 4H), 3.62 (t, 2H), 2.95 (d, J=14 Hz, 2H), 2.63 (t, 2H), 2.34 (m, 2H), 2.06 (t, 2H), 1.95 (d, 2H), 1.49 (q, 2H).)

EXAMPLE 4

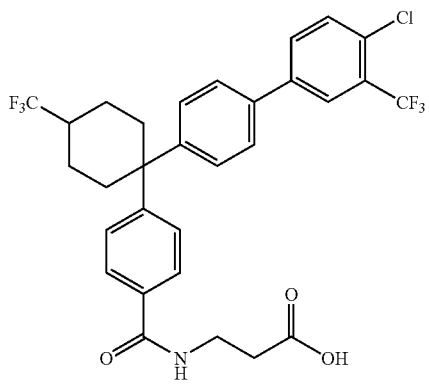

Step A: 4-[1-(4-Hydroxyphenyl)-4-(trifluoromethyl) cyclohexyl]benzoic acid

To Intermediate 5, Isomer B (172 mg, 0.45 mmol) in 1 mL of dioxane was added a solution of LiOH (44 mg, 1.8 mmol) in 0.5 mL of water. The reaction was stirred at 45° C. for 2 h. The 5 reaction mixture was taken up in aqueous pH 7 buffer and extracted with EtOAc. The aqueous layer was washed twice with EtOAc and the combined organic layers were concentrated under reduced pressure to provide the title compound as an off-white solid. LC-MS (ESI, neg. ion): m/z=363.2 $[M-1]^-$. $^1$H NMR (500 MHz, $CD_3OD$): δ 7.99 (d, J=8.5 Hz, 2H), 7.51 (d, J=8.5 Hz, 2H), 7.02 (d, J=8.7 Hz, 2H), 6.64 (d, J=8.7 Hz, 2H), 2.86 (d, J=13.5 Hz, 2H), 2.29 (m, 1H), 2.00-1.90 (overlapping t, d, 4H), 1.44 (q, 2H).

Step B: tert-Butyl 3-({4-[1-(4-hydroxyphenyl)-4-(trifluoromethyl)cyclohexyl]benzoyl}amino)propanoate To a solution of the title compound from the previous step (0.6 mmol), β-alanine tert-butyl ester hydrochloride (221 mg, 1.2 mmol), HOBt (184 mg, 1.2 mmol) and EDC (230 mg, 1.2 mmol) in 3 mL of DMF was added DIEA (0.32 mL, 1.8 mmol). The reaction was heated at 40° C. for 2 h, then partitioned between EtOAc/brine. The organic layer was collected and the aqueous layer was washed 2 times with EtOAc. The combined organic layers were concentrated under reduced pressure. Flash chromatography on silica gel eluting with a gradient of 0%-40% EtOAc/hexanes over 10 column volumes, then 40-100% EtOAc/hexanes over 5 column volumes provided the title compound. LC-MS (ESI): m/z=436.4 $[M+1]^+$. $^1$H NMR (500 MHz, $CD_3OD$): δ 7.76 (d, J=8.5 Hz, 2H), 7.49 (d, J=8.5 Hz, 2H), 7.01 (d, J=8.9 Hz, 2H), 6.62 (d, J=8.6 Hz, 2H), 3.59 (t, 2H), 2.84 (d, J=13.5 Hz, 2H), 2.56 (t, 2H), 2.29 (m, 1H), 1.96-1.87 (overlapping t, d, 4H), 1.44 (s, 9H).

Step C: tert-Butyl 3-({4-[4-(trifluoromethyl)-1-(4-{[(trifluoromethyl)sulfonyl]oxy}phenyl)cyclohexyl] benzoyl}amino)propanoate A solution of the title compound from the previous step (263 mg, 0.54 mmol) and pyridine (0.13 mL, 1.6 mmol) in 5 mL of DCM was cooled to −78° C. Trifluoromethanesulfonic anhydride (0.14 mL, 0.8 mmol) was slowly added to the reaction mixture. The reaction mixture was allowed to warm to ambient temperature and stirred for 0.5 h, then diluted with DCM and poured into 2 N HCl (aq). The organic layer was collected and the aqueous layer was washed twice with DCM. The combined organic layers were dried over $Na_2SO_4$ and concentrated under reduced pressure. Lyophilization from benzene provided the title compound as an off-white solid. LC-MS (ESI): m/z=568.3 $[M+1]^+$. $^1$H NMR (500 MHz, $CD_3OD$): δ 7.80 (d, J=8.5 Hz, 2H), 7.55 (d, J=8.5 Hz, 2H), 7.39 (d, J=9 Hz, 2H), 7.21 (d, J=8.9 Hz, 2H), 3.59 (t, 2H), 2.92 (d, J=13.5 Hz, 2H), 2.56 (t, 2H), 2.33 (m, 1H), 2.02 (t, 2H), 1.94 (br d, 2H), 1.43 (s, 9H).

Step D: 3-({4-[1-[4'-Chloro-3'-(trifluoromethyl)biphenyl-4-yl]-4-trifluoromethyl)cyclohexyl] benzoyl}amino)propanoic acid To a mixture of the title compound from the previous step (15 mg, 0.03 mmol), 4-chloro-3-(trifluoromethyl)phenylboronic acid (10 mg, 0.045 mmol) and tetrakis(triphenylphosphine)palladium(0) (3.5 mg, 0.003 mmol) was added 0.50 mL of ethylene glycol dimethyl ether and 0.010 mL of triethylamine. The reaction mixture was heated in a CEM Discover microwave reactor at 150° C. for 20 minutes. After cooling to ambient temperature, the reaction mixture was partitioned between EtOAc and saturated aqueous $NaHCO_3$ and the aqueous layer was washed twice with EtOAc. The combined organic phase was concentrated under reduced pressure. LC-MS (ESI): m/z=654.2 (M+1). The residue was dissolved in 0.70 mL of DCM with 0.015 mL of water and 0.50 mL of trifluoroacetic acid. The reaction was stirred at room temperature for 1 h. The solvent was removed and the product was purified by reverse phase chromatography (50-

100% MeCN/H$_2$O, both containing 0.1% TFA). Lyophilization afforded the title compound as a white solid. LC-MS (ESI): m/z=598.4 [M+1]$^+$. $^1$H NMR (500 MHz, CD$_3$OD): δ 7.91 (s, 1H), 7.82-7.78 (overlapping d, d, 3H), 7.64 (d, J=8.2 Hz, 1H), 7.57 (d, J=8.4 Hz, 2H), 7.53 (d, J=8.7 Hz, 2H), 7.37 (d, J=8.6 Hz, 2H), 3.63 (t, 2H), 2.96 (d, J=13.3 Hz, 2H), 2.64 (t, 2H), 2.34 (m, 1H), 2.06 (t, 2H), 1.96 (br d, 2H), 1.49 (q, 2H).

EXAMPLE 5

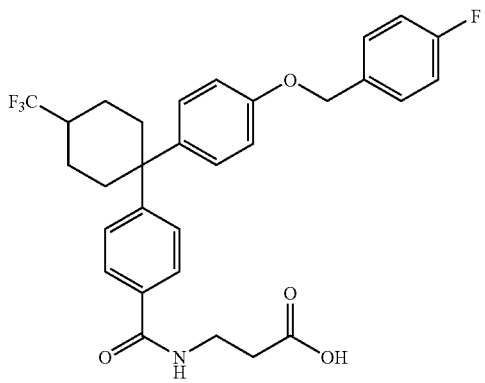

Step A: Ethyl 3-({4-[1-(4-hydroxyphenyl)-4-(trifluoromethyl)cyclohexyl]benzoyl}amino)propanoate To a solution of the title compound of Example 4, Step A (43 mg, 0.09 mmol), β-alanine ethyl ester hydrochloride (28 mg, 0.18 mmol), HOBt (28 mg, 0.18 mmol) and EDC (35 mg, 0.18 mmol) in 1 mL of DMF was added DIEA (0.047 mL, 0.27 mmol). The reaction was heated at 50° C. for 1.5 h, then partitioned between EtOAc/brine. The organic layer was collected and the aqueous layer was washed twice with EtOAc. The combined organic phase was concentrated under reduced pressure to provide the title compound. LC-MS (ESI): m/z=464.3 [M+1]$^+$.

Step B: Ethyl 3-({4-[1-{4-[4-fluorobenzyl)oxy]phenyl}-4-(trifluoromethyl)cyclohexyl]benzoyl}amino) propanoate To a solution of the title compound from the previous step (8.7 mg, 0.02 mmol) in 0.5 mL of DMF was added Cs$_2$CO$_3$ (17 mg, 0.045 mmol) then 4-fluorobenzyl bromide (0.0056 mL, 0.045 mmol). The reaction was stirred at 40° C. for 1 h, then allowed to stir at ambient temperature. The reaction was partitioned between EtOAc and saturated aqueous NaHCO$_3$. The organic layer was collected and the aqueous layer was washed 2 times with EtOAc. The combined organic layers were concentrated under reduced pressure to provide the title compound. LC-MS (ESI): m/z=572.3 [M+1]$^+$.

Step C: 3-({4-[1-(4-[(4-Fluorobenzyl)oxy]phenyl)-4-(trifluoromethyl)cyclohexyl]benzoyl}amino)propanoic acid To a solution the title compound from the previous step (11 mg, 0.02 mmol) in 0.80 mL of dioxane was added a solution of LiOH (5 mg, 0.2 mmol) in 0.40 mL of water. The reaction was stirred at 40° C. for 1 h, then left stirring at room temperature overnight. The reaction mixture was acidified with 0.050 mL of trifluoroacetic acid and purified by reverse phase chromatography (50%-100% MeCN/H$_2$O, both containing 0.1% TFA). Lyophilization afforded the title compound as a white solid. LC-MS (ESI): m/z=544.3 [M+1]$^+$. $^1$H NMR (500 MHz, CD$_3$OD): δ 7.77 (d, J=8.4 Hz, 2H), 7.50 (d, J=8.5 Hz, 2H), 7.40 (m, 2H), 7.11 (d, J=8.9 Hz, 2H), 7.06 (dd, J=8.8 Hz, 8.8 Hz, 2H), 6.83 (d, J=8.7 Hz, 2H), 4.98 (s, 2H), 3.62 (t, 2H), 2.86 (d, J=13.7 Hz, 2H), 2.61 (t, 2H), 2.29 (m, 1H), 1.98 (t, 2H), 1.90 (br d, 2H), 1.44 (q, 2H).

EXAMPLE 6

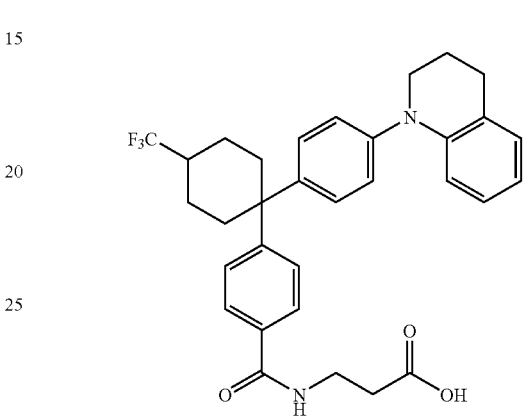

Step A: Methyl 4-[1-[4-(3,4-dihydroquinolin-1(2H)-yl)phenyl]-4-(trifluoromethyl)cyclohexyl]benzoate To a mixture of the title compound of Example 3, Step A (50 mg, 0.1 mmol), 1,2,3,4-tetrahydroquinoline (0.019 mL, 0.15 mmol), 2-(di-tert-butylphosphino)biphenyl (1 mg, 0.003 mmol), palladium (II) acetate (0.5 mg, 0.002 mmol) and sodium tert-butoxide (13 mg, 0.14 mmol) was added 0.30 mL of toluene. The reaction was stirred at 90° C. for 16 h, then partitioned between EtOAc/brine acidified with a few drops of 2 N HCl. The aqueous layer was washed with EtOAc then DCM. The combined organic layers were concentrated under reduced pressure to provide the product as a mixture of the title methyl ester and the hydrolyzed carboxylic acid. LC-MS (ESI): m/z=494.3 [M+1]$^+$.

Step B: 4-[1-[4-(3,4-Dihydroquinolin-1(2H)-phenyl]-4-(trifluoromethyl)cyclohexyl]benzoic acid To the title compound from the previous step (49 mg, 0.1 mmol) in 1 mL of dioxane was added a solution of LiOH (10 mg, 0.41 mmol) in 0.5 mL of water. The reaction was stirred at 40° C. The reaction mixture was acidified with a few drops trifluoroacetic acid, then partitioned between aqueous pH 7 buffer and EtOAc. The aqueous layer was washed twice with EtOAc and the combined organic phase was concentrated under reduced pressure. Reverse phase chromatography (55%-100% MeCN/H$_2$O, both containing 0.1% TFA) provided the title compound. LC-MS (ESI): m/z=480.3[M+1]$^+$.

Step C: 3-({4-[1-[4-(3,4-Dihydroquinolin-1 (2H)-yl) phenyl]-4-trifluoromethyl)cyclohexyl] benzoyl}amino)propanoic acid To a solution of the title compound from the previous step (0.1 mmol), β-alanine tert-butyl ester hydrochloride (36 mg, 0.2 mmol), HOBt (31 mg, 0.2 mmol) and EDC (38 mg, 0.2 mmol) in 1 mL of DMF was added DIEA (0.052 mL, 0.3 mmol). The reaction was allowed to stand at room temperature for 16 h, then partitioned between EtOAc/brine. The organic layer was collected and the aqueous layer was washed twice with EtOAc. The combined organic phase was concentrated under reduced pressure. LC-MS (ESI): m/z=607.3 [M+1]$^+$. The resultant residue was dissolved in 0.70 mL of DCM with 0.015 mL of water and 0.50 mL of trifluoroacetic acid. The reaction was stirred at room temperature for 1 h. The solvent was removed and the product was purified by reverse phase chromatography (10%-100% MeCN/H$_2$O, both containing 0.1% TFA). Lyophilization afforded the title compound as a beige solid. LC-MS (ESI): m/z=551.5 [M+1]$^+$. $^1$H NMR (500 MHz, CD$_3$OD) δ 7.79 (d, J=8.4 Hz, 2H), 7.54 (d, J=8.7 Hz, 2H), 7.18 (d, J=8.7 Hz, 2H), 7.05 (d, J=8.7 Hz, 2H), 6.96 (d, J=7.8 Hz, 1H), 6.80 (t, 1H), 6.60 (t, 1H), 6.54 (d, J=8.5 Hz, 1H), 3.62 (t, 2H), 3.52 (t, 2H), 2.91 (d, J=13.7 Hz, 2H), 2.77 (t, 2H), 2.63 (t, 2H), 2.32 (m, 1H), 2.05-1.91 (overlapping, t, d, m, 6H), 1.48 (q, 2H).

EXAMPLE 7

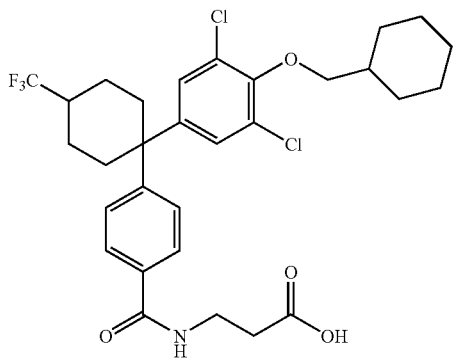

Step A: Methyl 4-[1-(3,5-dichloro-4-hydroxyphenyl-4-(trifluoromethyl)cyclohexyl]benzoate Intermediate 5, Isomer B (0.26 mmol, 100 mg) was taken up in SO$_2$Cl$_2$ (1 mL) in a 10 mL roundbottom flask fitted with a rubber septum and syringe needle (gas evolution). The resultant solution was heated at 50° C. for 16 h. The reaction was concentrated in vacuo and the residue was purified by preparative TLC on silica eluting with 15% EtOAc/hexanes to provide the title compound as an amber solid. LC-MS (ESI): m/z=447.0 [M+1]$^+$, 449.0 [M+3]$^+$.

Step B: Methyl 4-[1-{3,5-dichloro-4-[(cyclohexylmethyl)oxy]phenyl}-(trifluoromethyl)cyclohexyl]benzoate A slurry of the title compound from the previous step (0.08 mmol, 37 mg), bromomethylcyclohexane (0.25 mmol, 0.035 mL) and Cs$_2$CO$_3$ (0.25 mmol, 81 mg) in DMF (1 mL) was stirred at 60° C. for 4 h. The reaction mixture was partitioned between DCM/brine. The organic phase was dried over Na$_2$SO$_4$ and concentrated, then taken directly to the next step.

Step C: N-({4-[1-{3,5-Dichloro-4-[(cyclohexylmethyl)oxy]phenyl}-4-(trifluoromethyl)cyclohexyl]phenyl}carbonyl)-β-alanine To the title compound from the previous step in 2 mL of dioxane was added a solution of LiOH (1 mmol, 24 mg) in 1 mL of H$_2$O. The resulting solution was stirred at 40° C. for 1 h, then partitioned between DCM/1N HCl (aq). The organic phase was dried over Na$_2$SO$_4$ and concentrated in vacuo. The residue was taken up in DMF (1 mL) and β-alanine ethyl ester hydrochloride (0.2 mmol, 31 mg), EDC (0.2 mmol, 38 mg) and HOBt (0.2 mmol, 31 mg) were added, followed by DIEA (0.3 mmol, 0.052 mL). The reaction mixture was heated at 40° C. for 2 h, then partitioned between DCM/brine. The organic phase was concentrated in vacuo and the resulting residue was taken up in 2 mL of dioxane. A solution of LiOH (1 mmol, 24 mg) in 1 mL of H$_2$O was added and the resulting solution was stirred at 40° C. for 2 h. The reaction was acidified by addition of TFA (0.10 mL), then purified by reverse phase HPLC (60%-100% MeCN/H$_2$O, both containing 0.1% TFA). Lyophilization provided the title compound as a white solid. $^1$H NMR (500 MHz, d$_6$-DMSO) δ 12.18 (br s, 1H); 8.50 (t, J=5.5 Hz, 1H); 7.78 (d, J=8.4 Hz, 2H); 7.54 (d, J=8.4 Hz, 2H); 7.25 (s, 2H); 3.68 (d, J=6.2 Hz, 2H); 3.36-3.50 Hz (overlapping m, 4H); 2.90 (d, J=13.1 Hz, 2H); 2.43 (m, 1H); 1.89 (m, 2H); 1.57-1.85 (overlapping m, 8H); 1.00-1.28 (overlapping m, 7H).

EXAMPLE 8

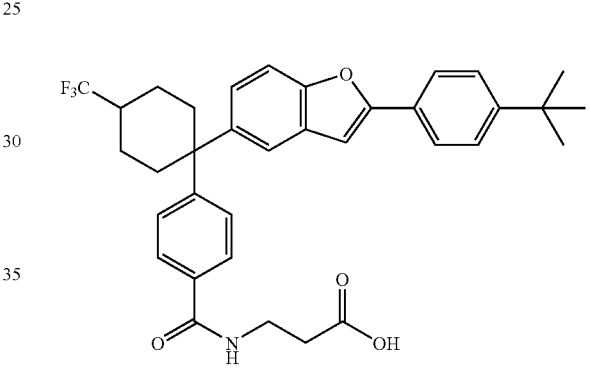

Step A: Methyl 4-[1-(4-hydroxy-3-iodophenyl)-4-trifluoromethyl)cyclohexyl]benzoate To a solution of Intermediate 5, Isomer B (220 mg, 0.58 mmol) and calcium carbonate (58 mg, 0.58 mmol) in 1.5 mL of MeOH and 0.5 mL of DCM was added benzyltrimethylammonium dichloroiodate (202 mg, 0.58 mmol). The reaction was stirred at room temperature, then partitioned between DCM/brine. The organic layer was concentrated under reduced pressure. Flash chromatography on silica gel (0%-30% EtOAc/hexanes over 10 column volumes then 30%-100% EtOAc/hexanes over 5 column volumes) gave incomplete separation of starting material and product. Repurification by reverse phase chromatography (0%-60% MeCN/H$_2$O, both containing 0.1% TFA) provided the title compound as a white solid. LC-MS (ESI): m/z=505.3 [M+1]$^+$. $^1$H NMR (500 MHz, CD$_3$OD): δ 8.00 (d, J=8.4 Hz, 2H), 7.52 (d, J=8.5 Hz, 2H), 7.47 (d, J=2.3, 1H), 7.01 (dd, J=8.6, 2.4 Hz, 1H), 6.67 (d, J=8.4 Hz, 1H), 3.89 (s, 3H), 2.83 (d, J=13.3 Hz, 2H), 2.30 (m, 1H), 1.98-1.89 (overlapping t, d, 4H), 1.41 (q, 2H).

Step B: Methyl 4-[1-[2-(4-tert-butylphenyl)-1-benzofuran-5-yl]-4-(trifluoromethyl)cyclohexyl]benzoate To a solution of the title compound from the previous step (36 mg, 0.07 mmol), copper iodide (1 mg, 0.005 mmol) and bis(triphenylphosphine)palladium(II) acetate (1 mg, 0.001 mmol) in 0.50 mL of DMF were added 4-tert-butylphenylacetylene (0.013 mL, 0.07 mmol), and piperidine (0.007 mL, 0.07 mmol). The reaction mixture was heated at 85° C. overnight, then partitioned into EtOAc/brine. The aqueous layer was washed twice with EtOAc. The combined organic phase was concentrated under reduced pressure to provide the crude product which was used without further purification.
LC-MS (ESI): m/z=535.4 [M+1]+.

Step C: 4-[1-[2-(4-tert-Butylphenyl)-1-benzofuran-5-yl]-4-(trifluoromethyl)cyclohexyl]benzoic acid To the title compound from the previous step (0.07 mmol) in 1 mL of dioxane was added a solution of LiOH (8 mg, 0.33 mmol) in 0.5 mL of water. The reaction was stirred at 45° C. for 2 h. The reaction mixture was partitioned between aqueous pH 7 buffer and EtOAc. The organic phase was collected and the aqueous layer was washed 2 times with EtOAc. The combined organic phase was concentrated under reduced pressure to provide the title compound which was used without further purification. LC-MS (ESI): m/z=521.4 [M+1]+.

Step D: 3-({4-[1-[2-(4-tert-Butylphenyl)-1-benzofuran-5-yl]-4-(trifluoromethyl)cyclohexyl]benzoyl}amino)propanoic acid To a solution of the title compound from the previous step, β-alanine tert-butyl ester hydrochloride (25 mg, 0.14 mmol), HOBt (21 mg, 0.14 mmol) and EDC (27 mg, 0.14 mmol) in 1 mL of DMF was added DIEA (0.037 mL; 0.21 mmol). The reaction mixture was heated to 45° C. for 1 h, allowed to stand at room temperature for 16 h, then partitioned between EtOAc/water. The organic layer was collected and the aqueous layer was washed twice with EtOAc. The combined organic phase was concentrated under reduced pressure. LC-MS (ESI): m/z=648.4 [M+1]+. The residue was dissolved in 0.70 mL of DCM with 0.015 mL of water and 0.30 mL of trifluoroacetic acid. The reaction was stirred at room temperature for 1 h. The solvent was removed and the product was purified by reverse phase chromatography (70%-100% MeCN/H$_2$O, both containing 0.1% TFA). Lyophilization afforded the title compound as a white solid. LC-MS (ESI): m/z=592.3 [M+1]+. $^1$H NMR (500 MHz, CD$_3$OD): δ 7.80 (d, J=8.4 Hz, 2H), 7.77 (d, J=8.5 Hz, 2H), 7.56 (d, J=8.5 Hz, 2H), 7.48 (overlapping d, d, 3H), 7.33 (d, J=8.7 Hz, 1H), 7.14 (dd, J=8.7 Hz, 2.1 Hz, 1H), 7.03 (s, 1H), 3.62 (t, 2H), 2.97 (d, J=13.9 Hz, 2H), 2.62 (t, 2H), 2.33 (m, 1H), 2.09 (t, 2H), 1.95 (br d, 2H), 1.50 (q, 2H), 1.34 (s, 9H).

EXAMPLE 9

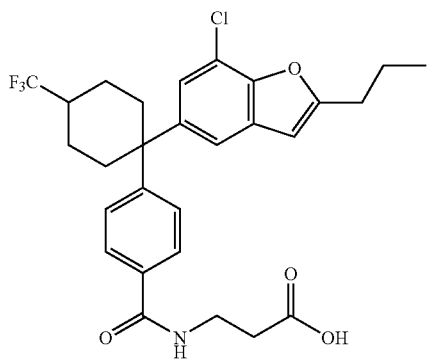

Step A: Methyl 4-[1-(3-chloro-4-hydroxy-5-iodophenyl)-4-(trifluoromethyl)cyclohexyl]benzoate The title compound of Example 8, Step A (0.08 mmol, 40 mg) was taken up in SO$_2$Cl$_2$ (0.5 mL) and the resulting solution was heated at 50° C. for 45 min. The reaction mixture was concentrated under reduced pressure and the residue was taken up in DCM and washed with brine. The organic phase was dried with Na$_2$SO$_4$ and concentrated in vacuo to provide the title compound as a foam which was used without further purification.

Step B: Methyl 4-[1-(7-chloro-2-propyl-1-benzofuran-5-yl)-4-(trifluoromethyl)cyclo-hexyl]benzoate To the title compound of the previous step (0.08 mmol) in DMF (0.2 mL) was added 1-penyne (0.1 mmol, 0.010 mL), CuI (0.02 mmol, 4 mg), PdCl$_2$(Ph$_3$P)$_2$ (0.01 mmol, 7 mg) and DIEA (0.2 mmol, 0.034 mL). The reaction mixture was heated with stirring at 75° C. for 2 h, then at 60° C. for 16 h. The reaction mixture was partitioned between DCM/brine. The organic layer was concentrated in vacuo and the product was isolated by preparative TLC on silica eluting with 15% EtOAc/hexanes to provide the title compound as a yellow solid.

Step C: N-{4-[1-(7-Chloro-2-propyl-1-benzofuran-5-yl)-4-(trifluoromethyl)cyclohexyl]benzoyl}-β-alanine To the title compound from the previous step in 2 mL of dioxane was added a solution of LiOH (1 mmol, 24 mg) in 1 mL of H$_2$O. The resulting solution was stirred at 40° C. for 1.5 h, then partitioned between DCM/1N HCl (aq). The organic phase was dried over Na$_2$SO$_4$ and concentrated in vacuo. The residue was taken up in DMF (1 mL) and β-alanine ethyl ester hydrochloride (0.1 mmol, 16 mg), EDC (0.1 mmol, 19 mg) and HOBt (0.1 mmol, 16 mg) were added, followed by DIEA (0.15 mmol, 0.026 mL). The reaction mixture was heated at 40° C. for 2 h, then partitioned between DCM/brine. The organic phase was concentrated in vacuo and the resulting residue was taken up in 4 mL of dioxane. A solution of LiOH (1 mmol, 24 mg) in 1 mL of H$_2$O was added and the resulting solution was stirred at 40° C. for 1.5 h. The reaction was acidified by addition of TFA (0.10 mL), then purified by reverse phase HPLC (60%-100% MeCN/H$_2$O, both containing 0.1% TFA). Lyophilization provided the title compound as a white solid. LC-MS (ESI): m/z=536. [M+1]+. $^1$H NMR (500 MHz, d$_5$-DMSO): δ 7.79 (d, J=8.7 Hz, 2H); 7.53 (d, J=8.7 Hz, 2H); 7.30 (d, J=1.6 Hz, 1H); 7.04 (d, J=1.6 Hz, 1H); 6.43 (s, 1H); 3.62 (t, J=7.0 Hz, 2H); 2.92 (d, J=13.3 Hz, 2H); 2.73 t, J=7.3 Hz, 2H); 2.63 (t, J=7.0 Hz, 2H); 2.31 (m, 1H); 2.03 (td, J=13.6 Hz, 3 Hz, 2H); 1.93 (m, 2H); 1.75 (m, 2H); 1.46 (m, 2H); 0.98 (t, J=14.5 Hz, 3H).

EXAMPLES 10 AND 11

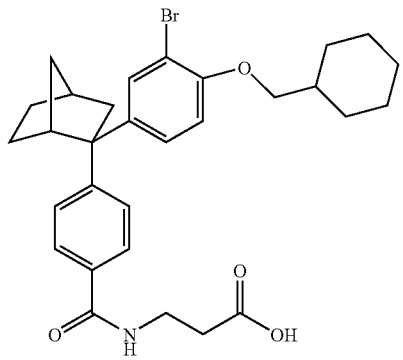

-continued

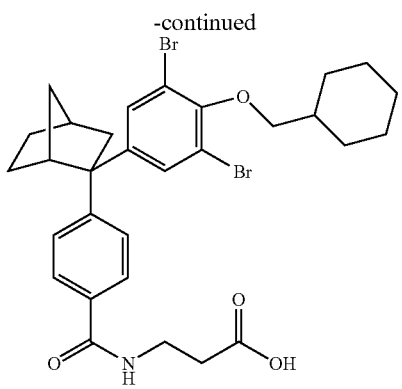

Step A: Methyl 4-[2-(3-bromo-4-hydroxyphenyl)bicyclo[2.2.1]hept-2-yl]-benzoate and Methyl 4-[2-(3,5-dibromo-4-hydroxyphenyl)bicyclo[2.2.1]hept-2-yl]benzoate Intermediate 7, Isomer B (1 mmol, 322 mg) and N-bromosuccinimide (1.3 mmol, 231 mg) were combined in DCM (5 mL) and the reaction mixture was allowed to stand at room temperature for 16 h. The reaction mixture was taken up in DCM and washed with saturated $NaHCO_3$ (aq), then brine. The resultant mixture of starting material, monobromo- and bisbromo products were concentrated in vacuo and taken directly to the next step. Monobromide LC-MS (ESI): m/z=403.0 [M+3]+, 401.0 [M+1]+; Bisbromide LC-MS (EST): m/z=481.0 [M+3]+, 482.9 [M+5]+, 479.0 [M+1]+.

Step B: Methyl 4-{2-[3-bromo-4-(cyclohexylmethoxy)phenyl]bicyclo[2.2.1]hept-2-yl}benzoate and Methyl 4-{2-[3,5-dibromo-4-cyclohexylmethoxy)phenyl]bicyclo[2.2.1]hept-2-yl}benzoate To the product from the previous step in DMF (5 mL) was added bromomethylcyclohexane (2 mmol, 0.28 mL) and $Cs_2CO_3$ (2 mmol, 650 mg). The reaction mixture was heated with stirring at 50° C. for 16 h, then partitioned between DCM/brine. The organic phase was dried over $Na_2SO_4$ and concentrated. The residue was taken up in minimum DCM and passed through a silica plug eluting with 15% EtOAc/hexanes. The filtrate containing the des-bromo, mono-bromo and bis-bromo ethers was concentrated to a beige solid and used without further purification.

Step C: N-(4-{2-[3-bromo-4-(cyclohexylmethoxy)phenyl]bicyclo[2.2.1]hept-2-yl}benzoyl)-β-alanine and N-(4-{2-[3,5-dibromo-4-(cyclohexylmethoxy)phenyl]bicyclo[2.2.1]hept-2-yl}benzoyl)-β-alanine To the mixture from the previous step in 2 mL of dioxane was added a solution of LiOH (1 mmol, 24 mg) in 0.5 mL of $H_2O$. The resulting solution was stirred at 40° C. for 3 h, then partitioned between DCM/1N HCl (aq). The organic phase was dried over $Na_2SO_4$ and concentrated in vacuo. The residue was taken up in DMF (1 mL) and β-alanine ethyl ester hydrochloride (0.2 mmol, 31 mg), EDC (0.2 mmol, 38 mg) and HOBt (0.2 mmol, 31 mg) were added, followed by DEA (0.3 mmol, 0.052 mL). The reaction mixture was allowed to stand at room temperature for 16 h, then partitioned between DCM/brine. The organic phase was concentrated in vacuo and the resulting residue was taken up in 2 mL of dioxane. A solution of LiOH (1 mmol, 24 mg) in 1 mL of $H_2O$ was added and the resulting solution was stirred at 40° C. for 2 h. The reaction was acidified by addition of TFA (0.10 mL), and purified by reverse phase HPLC (60% to 100% $MeCN/H_2O$, both containing 0.1% TFA) to provide monobromide title compound Example 10 and bisbromide title compound Example 11.

Example 10: LCMS (ESI): m/z=556.2 [M+3]+; 554.2 [M+1]+. $^1$H NMR (500 MHz, d6-DMSO): δ 12.18 (br s, 1H); 8.39 (t, J=5.6 Hz, 1H); 7.66 (d, J=8.5 Hz, 2H); 7.46 (d, J=2.5 Hz); 7.38 (d, J=8.2 Hz); 7.30 (dd, J=8.7 Hz, J=2.3 Hz, 1H); 6.90 (d, J=8.7 Hz, 1H); 3.74 (d, J=6.4 Hz, 2H); 2.46 (t, J=7.0 Hz, 2H); 2.34 (m, 1H); 2.25 (m, 2H); 1.77 (m, 2H); 1.57-1.73 (overlapping m, 4H); 1.36-1.51 (overlapping m, 3H); 1.32 (d, J=9.2 Hz, 1H); 0.06-1.28 (overlapping m, 7H); 3H obscured by solvent from 3.3-3.6 ppm.

Example 11: LCMS (ESI): m/z=634.0 [M+3]+; 636.1 [M+5]+; 632.1 [M+1]+. $^1$H NMR (500 MHz, $d_6$-DMSO): δ 12.20 (br s, 1H); 8.43 (t, J=5.4 Hz, 1H); 7.69 (d, J=8.2 Hz, 2H); 7.60 (s, 2H); 7.45 (d, J=8.2 Hz, 2H); 3.66 (d, J=5.9 Hz, 2H); 2.47 (t, J=7.1 Hz, 2H); 2.35 (m, 1H); 2.27 (m, 2H) 1.58-1.86 (overlapping m, 6H); 1.37-1.52 (overlapping m, 3H); 1.33 (d, J=9.4 Hz, 1H); 1.00-1.29 (overlapping m, 7H); 3H obscured by solvent from 3.24-3.50 ppm.

EXAMPLE 12

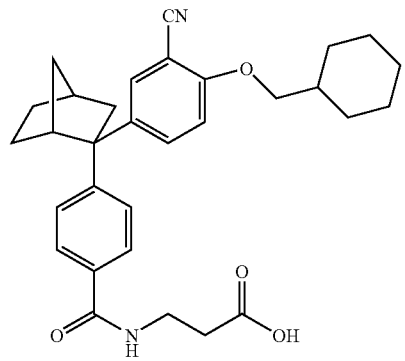

Step A: Methyl 4-{2-[3-cyano-4-(cyclohexylmethoxy)phenyl]bicyclo[2.2.1]hept-2-yl}benzoate The product mixture from Example 10, Step B (0.1 mmol, 53 mg), Zn (CN)$_2$ (0.15 mmol, 18 mg), Pd$_2$dba$_3$ (0.01 mmol, 9 mg) and bis(diphenylphosphino)ferrocene (0.024 mmol, 13 mg) were heated in DMF (0.4 mL) containing $H_2O$ (0.008 mL) at 110° C. for 14 h. The reaction mixture was partitioned between DCM/brine and the organic phase was passed through a 0.45 micron filter and concentrated in vacuo. The crude reaction mixture was taken directly to the next step.

Step B: N-(4-{2-[3-cyano-4-(cyclohexylmethoxy)phenyl]bicyclo[2.2.1]hept-2-yl}benzoyl)-β-alanine To the product from the previous step in 1 mL of dioxane was added a solution of LiOH (1 mmol, 24 mg) in 0.5 mL of $H_2O$. The resulting solution was stirred at 40° C. for 3 h, then partitioned between DCM/1N HCl (aq). The organic phase was dried over $Na_2SO_4$ and concentrated in vacuo. The residue was taken up in DMF (1 mL) and β-alanine ethyl ester hydrochloride (0.2 mmol, 31 mg), EDC (0.2 mmol, 38 mg) and HOBt (0.2 mmol, 31 mg) were added, followed by DIEA (0.3 mmol, 0.05 mL). The reaction mixture was allowed to stand at ambient temperature for 16 h, then partitioned between DCM/brine. The organic phase was concentrated in vacuo and the resulting residue was taken up in 2 mL of dioxane. A solution of LiOH (1 mmol, 24 mg) in 1 mL of H$_2$O was added and the resulting solution was stirred at 40° C. for 2 h. The reaction was acidified by addition of TFA (0.10 mL), and the mononitrile product was isolated by reverse phase HPLC (40-100% MeCN/H$_2$O, both containing 0.1% TFA). Lyophilization provided the title compound as a white solid. LCMS (ESI): m/z=501.3 [M+1]$^+$. $^1$H NMR (500 MHz, d$_6$-DMSO): δ 12.18 (br s, 1H); 8.39 (t, J=5.5 Hz, 1H); 7.70 (d, J=2.5 Hz, 1H); 7.66 (d, J=8.5 Hz, 2H); 7.56 (dd, J=8.9 Hz, J=2.5 Hz, 1H); 7.40 (d, J=8.4 Hz, 2H); 7.03 (d, J=9 Hz, 1H); 3.83 (d, J=6.2 Hz, 2H); 2.45 (t, J=7.1 Hz, 2H); 2.34 (s, 1H); 2.26 (s, 2H); 1.57-1.78 (overlapping m, 5H); 1.46-1.55 (overlapping m, 4H); 1.31 (m, 1H); 0.95-1.28 (overlapping m, 7H); 3.2-3.53 3H obscured by solvent.

EXAMPLE 13

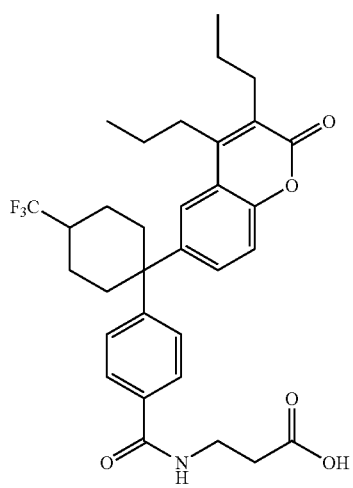

Step A: Methyl 4-[1-(2-oxo-3,4-dipropyl-2H-chromen-7-yl)-4-(trifluoromethyl)cyclohexyl]benzoate To a solution of the title compound of Example 8, Step A (16 mg, 0.03 mmol), tetrabutylammonium chloride (8.3 mg, 0.03 mmol) and palladium acetate (1 mg, 0.004 mmol) in 0.5 mL of DMF was added pyridine (0.005 mL, 0.06 mmol) and 4-octyne (0.022 mL, 0.15 mmol). The reaction was flushed with CO, then heated under an atmosphere of CO (balloon) overnight at 115° C. The reaction was partitioned between EtOAc/water and the aqueous layer was washed twice with EtOAc. The combined organic phase was concentrated under reduced pressure. The product was purified by flash chromatography on silica gel eluting with a gradient of 0%-20% EtOAc/hexanes over 10 column volumes, then 20%-100% EtOAc/hexanes over 10 column volumes, to afford the title compound as a white solid. LC-MS (ESI): m/z=515.5 [M+1]$^+$.

Step B: 4-[1-(2-Oxo-3,4-dipropyl-2H-chromen-7-yl)-4-trifluoromethyl)cyclohexyl]benzoic acid To the title compound from the previous step (6 mg, 0.01 mmol) in 1 mL of dioxane was added a solution of LiOH (5 mg, 0.21 mmol) in 0.5 mL of water. The reaction mixture was stirred at room temperature overnight and taken up in aqueous pH 7 buffer and EtOAc. The organic layer was collected and the aqueous layer was washed twice with EtOAc. The combined organic phase was concentrated under reduced pressure to provide the title compound. LC-MS (ESI): m/z=501.4 [M+1]$^+$.

Step C: 3-({4-[1-(2-Oxo-3,4-dipropyl-2H-chromen-7-yl)-4-(trifluoromethyl)cyclohexyl]benzoyl}amino) propanoic acid To a solution of the title compound from the previous step (0.01 mmol), β-alanine tert-butyl ester hydrochloride (4 mg, 0.02 mmol), HOBt (3 mg, 0.02 mmol) and EDC (4 mg, 0.02 mmol) in 0.8 mL DMF was added DIEA (0.005 mL, 0.03 mmol). The reaction was heated at 45° C. for 1 h, then partitioned between EtOAc/water. The organic layer was collected and the aqueous layer was washed 2 times with EtOAc. The combined organic phase was concentrated under reduced pressure. LC-MS (ESI): m/z=628.6 [M+1]$^+$.

The residue was dissolved in 0.70 mL DCM with 0.015 mL of water and 0.30 mL trifluoroacetic acid. The reaction was stirred at room temperature for 45 min. The solvent was removed and the product was purified by reverse phase chromatography (30%-100% MeCN/H$_2$O, both containing 0.1% TFA). Lyophilization afforded the title compound as a white solid. LC-MS (ESI): m/z=572.5[M+1]$^+$. $^1$H NMR (500 MHz, CD$_3$OD): δ 7.86 (d, J=8.5 Hz, 2H), 7.56 (overlapping d, m, 3H), 7.22 (m, 2H), 3.63 (t, 2H), 2.89 (d, J=13 Hz, 2H), 2.68-2.62 (overlapping m, 4H), 2.55 (m, 2H), 2.38 (m, 1H), 2.11 (t, 2H), 1.96 (br d, 2H), 1.55-1.46 (overlapping m, 4H), 1.40 (m, 2H), 1.00-0.94 (overlapping m, 6H).

EXAMPLE 14

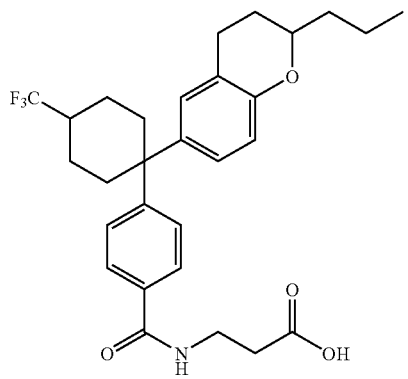

Step A: Methyl 4-[1-{2-[(1E)-prop-1-en-1-yl]-3,4-dihydro-2H-chromen-6-yl}-4-(trifluoromethyl)cyclohexyl]benzoate To the title compound of Example 8, Step A (27 mg, 0.05 mmol) in 0.5 mL of DMF was added palladium acetate (1.2 mg, 0.005 mmol), lithium chloride (4.2 mg, 0.1 mmol), DIEA (0.070 mL, 0.4 mmol), and 1,4-hexadiene (0.046 mL, 0.4 mmol). The reaction was stirred at 95° C. for 16 h, then partitioned between EtOAc/water. The organic layer was collected and the aqueous layer was washed twice with EtOAc. The combined organic layers were concentrated under reduced pressure. The product was purified by flash chromatography on silica gel eluting with a gradient of 0%-30% EtOAc/hexanes over 10 column volumes, then 30%-100% EtOAc/hexanes over 5 column volumes, to afford the title compound as a yellow oil. LC-MS (ESI): m/z=459.2 [M+1]$^+$.

Step B: Methyl 4-[1-(2-propyl-3,4-dihydro-2H-chromen-6-yl)-4-(trifluoromethyl)cyclohexyl]benzoate To the title compound from the previous step (7.5 mg, 0.016 mmol) in 1 mL EtOAc was added catalytic 20% palladium hydroxide on carbon. The reaction was stirred for 5.5 h at room temperature under $H_2$ (balloon). The solution was filtered through celite and the filtrate was concentrated under reduced pressure to provide the title compound which was used without further purification. LC-MS (ESI): m/z=461.2 [M+1]$^+$.

Step C: 4-[1-(2-Propyl-3,4-dihydro-2-chromen-6-yl)-4-(trifluoromethyl)cyclohexyl]benzoic acid To the title compound from the previous step (0.016 mmol) in 1 mL of dioxane was added a solution of LiOH (10 mg, 0.4 mmol) in 0.5 mL of water. The reaction was stirred at room temperature overnight. The reaction mixture was partitioned between aqueous pH 7 buffer and EtOAc. The organic layer was collected and the aqueous layer was washed 2 times with EtOAc. The combined organic layers were concentrated under reduced pressure. LC-MS (ESI, neg. ion): m/z=445.3 [M−1]$^−$.

Step D: 3-({4-[1-(2-Propyl-3,4-dihydro-2H-chromen-6-yl)-4-(trifluoromethyl)cyclohexyl]benzoyl}amino)propanoic acid To a solution of the compound from the previous step (0.016 mmol), β-alanine tert-butyl ester hydrochloride (6 mg, 0.03 mmol), HOBt (5 mg, 0.03 mmol) and EDC (6 mg, 0.03 mmol) in 0.5 mL DMF was added DIEA (0.008 mL, 0.05 mmol). The reaction was heated at 40° C. for 1 h, then partitioned between EtOAc/water. The organic layer was collected and the aqueous layer was washed 2 times with EtOAc. The combined organic layers were concentrated under reduced pressure. LC-MS (ESI): m/z=574.4 [M+1]$^+$. The residue was dissolved in 0.70 mL of DCM containing 0.015 mL of water and 0.30 mL of trifluoroacetic acid. The reaction was stirred at room temperature for 1 h. The solvent was removed and the product was purified by reverse phase chromatography (30%-100% MeCN/$H_2O$, both containing 0.1% TFA). Lyophilization afforded the title compound as a white solid. LC-MS (ESI): m/z=518.3 [M+1]$^+$. $^1$H NMR (500 MHz, CD$_3$OD): δ 7.77 (d. J=8.4 Hz, 2H), 7.49 (d, J=8.5 Hz, 2H), 6.87 (overlapping d, d, 2H), 6.55 (d, J=8.7 Hz, 1H), 3.89 (m, 1H), 3.62 (t, 2H), 2.84 (br d, 2H), 2.73-2.62 (overlapping m, d), 2.27 (m, 1H), 1.98-1.88 (overlapping m), 1.67-1.39 (overlapping m), 0.95 (t, 2H).

EXAMPLE 15

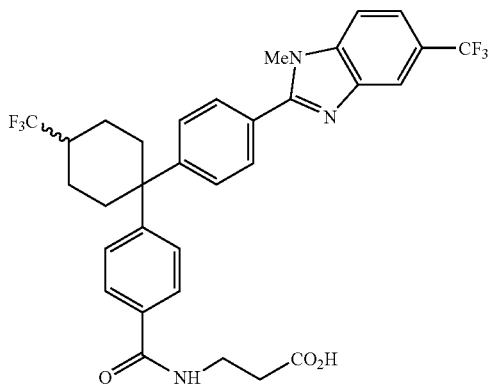

Step A: Dimethyl 4,4'-[4-(trifluoromethyl)cyclohexane-1,1-diyl]dibenzoate

The title compound was prepared from the bis-triflate product from Intermediate 5, Method 2, Step A using conditions analogous to those described in Intermediate 5, Method 2, Step B. LC-MS (ESI): m/z=421.3 [M+1]$^+$. $^1$H NMR (500 MHz, CD$_3$OD): δ 8.02 (d, J=8.5 Hz, 2H), 7.89 (d, J=8.7 Hz, 2H), 7.58 (d, J=8.5 Hz, 2H), 7.37 (d, J=8.7 Hz, 2H), 3.90 (s, 3H), 3.86 (s, 3H), 2.96 (br d, J=13.2 Hz, 2H), 2.35 (m, 1H), 2.05 (t, 2H), 1.96 (br d, 2H), 1.48 (q, 2H).

Step B: 4-[1-[4-(Methoxycarbonyl)phenyl]-4-(trifluoromethyl)cyclohexyl]benzoic acid To the title compound from the previous step (630 mg, 1.5 mmol) in 9.5 mL of 1,4-dioxane and 5 mL of water was added portionwise LiOH (49 mg, 2 mmol). The reaction mixture was heated at 40° C. for 2 h, acidified with 2N HCl (aq) and extracted twice with EtOAc. The organic phase was concentrated in vacuo and the resultant residue was separated by preparative thin layer chromatography on silica gel (15% MeOH in dichloromethane) to provide the title compound. LC-MS (ESI, neg. ion): m/z=405.2 [M−1]$^−$.

Step C: Methyl 4-[1-{4-[1-methyl-5-(trifluoromethyl)-1H-benzimidazol-2-yl]-phenyl}-4-(trifluoromethyl)cyclohexyl]benzoate To the title compound from the previous step (40 mg, 0.1 mmol) and 0.5 mL of POCl$_3$ was added 1-N-methyl-4-trifluoromethyl-1,2-phenylenediamine (23 mg, 0.12 mmol). The resulting mixture was heated at 80° C. for 2.5 h. Another 30 mg (0.16 mmol) of the phenylenediamine was introduced and the reaction mixture was heated at 80° C. for another 1 h. The reaction was concentrated in vacuo and the residue was purified on reverse phase HPLC (10% to 100% MeCN/$H_2O$, each containing 0.05% (v/v) of TFA) to provide the title compound as a mixture of isomers. LC-MS (ESI): m/z=561.3[M+1]$^+$.

Step D: N-{4-[1-{4-[1-Methyl-5-(trifluoromethyl)-1H-benzimidazol-2-yl]phenyl}-4(trifluoromethyl)cyclohexyl]benzoyl}-β-alanine To the title compound from the previous step (30 mg, 0.054 mmol) in 0.5 mL of 1,4-dioxane and 0.25 mL of water was added LiOH (17 mg, 0.7 mmol). The resultant mixture was stirred at ambient temperature for 16 h, acidified with 1N HCl, and extracted with EtOAc. The organic phase was concentrated to afford the acid. LC-MS (ESI): m/z=547.3 [M+1]$^+$.

The crude acid was treated with EDC (21 mg, 0.1 mmol), HOBt (17 mg, 0.12 mmol), β-alanine tert-butyl ester hydrochloride (20 mg, 0.11 mmol) and DIEA (0.033 mL, 0.2 mmol) in 0.5 mL DMF at ambient temperature for 2.5 h. The reaction mixture was partitioned between water and EtOAc. The organic phase was washed with water, concentrated and the residue was taken up in a mixture of 0.25 mL of TFA and 0.5 mL of dichloromethane. After 4 h, the solvent was removed and the residue was purified by reverse phase HPLC (30% to 100% MeCN/$H_2O$, each containing 0.05% (v/v) of TFA) to give the title compound as a mixture of two isomers. LC-MS (ESI): m/z=618.2 [M+1]$^+$.

EXAMPLE 16

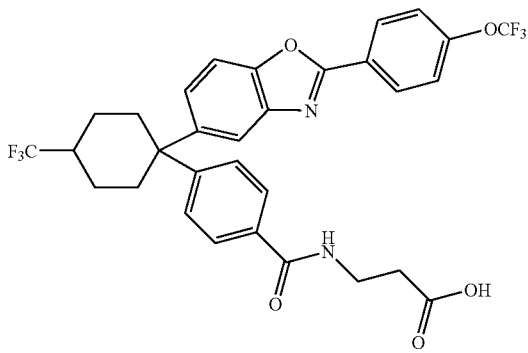

Step A: Methyl 4-[1-(4-hydroxy-3-nitrophenyl)-4-(trifluoromethyl)cyclohexyl]benzoate To Intermediate 5, Isomer B (228 mg, 0.6 mmol) in a mixture of 14 mL of acetonitrile and 5 mL of dichloromethane was added eerie ammonium nitrate (509 mg, 0.93 mmol). After 20 min the reaction mixture was partitioned between hexanes-EtOAc-DCM and aq. sodium bisulfite. The organic phase was purified by flash chromatography on silica gel eluting with 20% EtOAc/hexanes to provide the title compound. $^1$H NMR (500 MHz, CD$_2$Cl$_2$): δ (ppm) 10.41 (s, 1H), 8.03 (d, J=8.5 Hz, 2H), 7.98 (d, J=2.3 Hz, 1H), 7.46 (d, J=8.5 Hz, 2H), 7.37 (dd, J=8.9, 2.5 Hz, 1H), 7.03 (d, J=8.9 Hz, 1H), 3.90 (s, 3H), 2.86 (d, J=14.2 Hz, 2H), 2.23 (m, 1H).

Step B: Methyl 4-[1-(3-amino-4-hydroxyphenyl-4-(trifluoromethyl)cyclohexyl]benzoate The title compound from the previous step (124 mg, 0.29 mmol) in 1.4 mL of DMF and 0.14 mL of water was treated with tin(II) chloride dihydrate (335 mg, 1.5 mmol). The reaction was heated at 50° C. until reaction was complete as indicated by TLC. The reaction mixture was diluted with ca. 50 mL of 1:1 (v/v) hexanes:EtOAc and 10 mL of aq. sodium bicarbonate. The resulting slurry was filtered and the filtrate was partitioned between EtOAc/brine. The organic phase was purified by flash chromatography on silica gel eluting with a gradient of 33% to 50% EtOAc/hexanes to provide the title compound. $^1$H NMR (500 MHz, acetone-d$_6$): δ (ppm) 7.98 (d, J=8.2 Hz, 2H), 7.58 (d, J=8.6 Hz, 2H), 6.60 (m, 2H), 6.39 (dd, J=8.2, 2.3 Hz, 1H), 3.88 (s, 3H).

Step C: Methyl 4-[1-2-(4-fluorophenyl)-1,3-benzoxazol-5-yl]-4-(trifluoromethyl)cyclohexyl]benzoate A solution of the title compound from the previous step (19 mg, 0.05 mmol), 4-trifluoromethoxybenzoyl chloride (0.016 mL, 0.1 mmol) and triethylamine (0.023 mL, 0.17 mmol) in 0.5 mL of dichloromethane was stirred for 15 min. Solvent was removed in vacuo and the residue was taken up in 0.5 mL of MeOH and heated at 40° C. for 1 h. Solvent was removed in vacuo and to the resultant residue were added p-toluenesulfonic acid hydrate (37 mg, 0.2 mmol) and toluene (2 mL). The reaction mixture was heated at 120° C. for 50 min, and was partitioned between EtOAc and aq. sodium bicarbonate. The organic layer was concentrated to give the title compound which was used without further purification. LC-MS (ESI): m/z=564.3 [M+1]$^+$.

Step D: N-{4-[1-[2-(4-Fluorophenyl)-1,3-benzoxazol-5-yl]-4-(trifluoromethyl)cyclohexyl]benzoyl}-β-alanine The title compound from the previous step was treated with 0.5 mL of 1 N NaOH (aq) in 1 mL of 1,4-dioxane at 50° C. for 1 h 15 min. The mixture was acidified by addition of dilute HCl and extracted with EtOAc. The organic phase was concentrated and the resultant residue was taken up in DMF (1 mL) and treated with EDC (40 mg, 0.2 mmol), HOBt (40 mg, 0.2 mmol), β-alanine tert-butyl ester hydrochloride (40 mg, 0.2 mmol) and DIEA (0.06 mL, 0.4 mmol) at 50° C. for 25 min. The reaction mixture was partitioned between water and EtOAc. The organic phase was concentrated and the residue was taken up in a mixture of 0.5 mL of TFA and 1 mL of dichloromethane. After 2 h the solvent was removed and the residue was purified by reverse phase HPLC (45% to 100% MeCN/H$_2$O, each containing 0.05% (v/v) of TFA) to give the title compound. LC-MS (ESI): m/z=621.3 [M+1]$^+$. $^1$H NMR (500 MHz, acetone-d$_6$): δ (ppm) 8.34 (d, J=8.9 Hz, 2H), 7.91 (d, J=8.5 Hz, 2H), 7.82 (t, J=5.4 Hz, 1H), 7.69 (d, J=1.8 Hz, 1H), 7.64 (d, J=8.5 Hz, 2H), 7.56 (m, 3H), 7.34 (dd, J=8.7, 2.0 Hz, 1H), 3.64 (m, 2H), 3.08 (d, J=13.3 Hz, 2H), 2.65 (t, J=6.9 Hz, 2H), 2.46 (m, 1H), 2.16 (m, 2H), 1.99 (m, 2H), 1.52 (m, 2H).

EXAMPLE 17

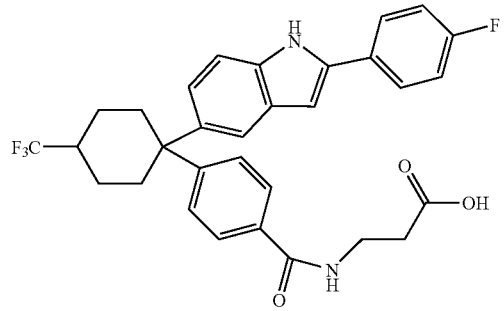

Step A: Methyl 4-[1-{4-[(4-fluorophenyl)ethynyl]-3-nitrophenyl}-4-(trifluoromethyl)cyclohexyl]benzoate To the title compound of Example 16, Step A (24 mg, 0.057 mmol) in DCM (1 mL) was added 0.03 mL each of pyridine and trifluoromethanesulfonic anhydride. After 1 h, aqueous workup provided the crude triflate. A portion of the crude triflate (22 mg) was taken up in THF (0.6 mL), then Pd(OAc)$_2$ (2.7 mg, 0.01 mmol), PPh$_3$ (7.6 mg, 0.03 mmol), 1-ethynyl-4-fluorobenzene (18 mg, 0.15 mmol) and triethylamine (0.3 mL) were added. The resultant mixture was heated to 70° C. for 2.5 h. The reaction mixture was concentrated in vacuo and the residue was purified by preparative TLC on silica gel (12% EtOAc/hexanes) to provide the title compound. $^1$H NMR (500 MHz, CDCl$_3$): δ (ppm) 8.07 (d, J=8.5 Hz, 2H), 7.96 (d, J=2.1 Hz, 1H), 7.33 (dd, J=8.5, 2.1 Hz, 1H), 7.07 (m, 2H), 3.93 (s, 3H), 2.88 (d, J=12.1 Hz, 2H), 2.21 (m, 1H), 1.53 (m, 2H).

Step B: Methyl 4-[1-{3-amino-4-[(4-fluorophenyl)ethynyl]phenyl}-4-(trifluoromethyl)cyclohexyl]benzoate To the title compound from the previous step (17 mg, 0.034 mmol) in 0.3 mL of DMF and 0.03 mL of water was added tin(II) chloride dihydrate (34 mg, 0.15 mmol). The reaction was heated at 40° C. for 1 h. The reaction mixture was partitioned between a 1:1 (v/v) mixture of hexane/EtOAc and aq. sodium bicarbonate. The organic layer was filtered and concentrated in vacuo. The resulting residue was purified by preparative TLC on silica gel (33% EtOAc/hexanes) to give the title compound. $^1$H NMR (500 MHz, DMF-$d_7$): δ (ppm) 7.98 (d, J=8.5 Hz, 2H), 7.63 (m, 4H), 7.21 (m, 2H), 7.15 (d, J=8.2 Hz, 1H), 6.73 (d, J=1.8 Hz, 1H), 6.54 (dd, J=8.2, 1.8 Hz, 1H), 3.88 (s, 3H), 3.67 (m, 2H), 1.38 (m, 2H).

Step C: Methyl 4-[1-[2-(4-fluorophenyl)-1H-indol-6-yl]-4-(trifluoromethyl)cyclohexyl]benzoate The title compound from the previous step (10 mg, 0.02 mmol) and PdCl$_2$ (1.1 mg, 0.006 mmol) were heated in 1 mL of acetonitrile for 1 h. Removal of solvent gave the crude product which was carried over to the next step without further purification. $^1$H NMR (500 MHz, CDCl$_3$): δ (ppm) 8.56 (s, 1H), 8.03 (d, J=8.5 Hz, 2H), 7.66 (m, 2H), 7.54 (d, J=8.7 Hz, 2H), 7.48 (d, J=8.4 Hz, 1H), 7.27 (s, 1H), 7.17 (m, 2H), 7.00 (dd, J=8.5, 1.6 Hz, 1H), 6.71 (s, 1H), 3.91 (s, 3H), 2.96 (d, J=13.3 Hz, 2H), 2.27 (m, 1H), 1.55 (m, 2H).

Step D: N-{4-[1-[2-(4-Fluorophenyl)-1H-indol-6-yl]-4-(trifluoromethyl)cyclohexyl]benzoyl}-β-alanine The title compound from the previous step was saponified in a mixture of 1 mL of 1,4-dioxane and 0.5 mL of 1 N NaOH at 50° C. for 3.5 h. The reaction mixture was acidified by addition of dilute HCl and extracted with EtOAc. The organic phase was concentrated and the resultant residue was taken up in DMF (1 mL) and treated with EDC (40 mg, 0.2 mmol), HOBt (40 mg, 0.2 mmol), β-alanine tert-butyl ester hydrochloride (40 mg, 0.2 mmol) and DIEA (0.6 mL, 0.4 mmol) at 50° C. for 25 min. The reaction mixture was partitioned between water and EtOAc. The organic phase was concentrated and the residue was taken up in a mixture of 0.5 mL of TFA and 1 mL of dichloromethane. After 2 h the solvent was removed and the residue was purified on reverse phase HPLC (45% to 100% MeCN/H$_2$O, each containing 0.05% (v/v) of TFA) to provide the title compound. $^1$H NMR (500 MHz, acetone-$d_6$): δ (ppm) 10.54 (s, 1H), 7.89 (d, J=8.5 Hz, 2H), 7.85 (m, 3H), 7.59 (d, J=8.5 Hz, 2H), 7.42 (d, J=8.5 Hz, 1H), 7.20 (m, 2H), 7.14 (s, 1H), 7.03 (dd, J=8.5, 1.6 Hz, 1H), 6.76 (d, J=1.8 Hz, 1H), 3.65 (m, 2H), 2.96 (d, J=13.7 Hz, 2H), 2.66 (t, J=6.9 Hz, 2H), 2.44 (m, 1H), 2.16 (m, 2H), 1.95 (m, 2H), 1.50 (m, 2H).

EXAMPLE 18, ISOMERS A AND B

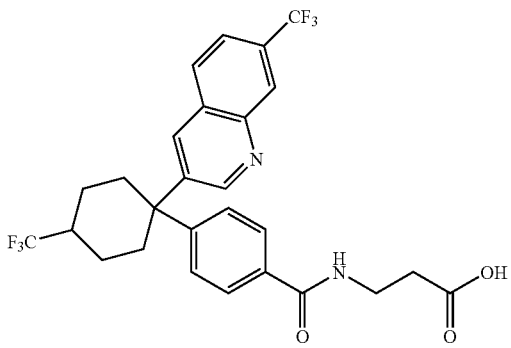

Step A: 4-(Trifluoromethyl)-1-[7-(trifluoromethyl)quinolin-3-yl]cyclohexanol

To a cold (−78° C.) anhydrous THF solution of 2-methoxy-6-bromoquinoline (300 mg, 1.09 mmol) was added BuLi (0.46 mL of a 2.5 M solution in hexanes, 1.14 mmol). The mixture was stirred at −78° C. under a nitrogen atmosphere for 15 min, then 4-(trifluoromethyl)cyclohexanone (180 mg, 1.14 mmol) was slowly added. After addition, the dry ice/acetone bath was allowed to warm to room temperature. The reaction mixture was quenched with saturated NH$_4$Cl solution, then extracted with EtOAc/hexanes. The organic layer was evaporated in vacuo. The crude residue was purified by flash chromatography on silica gel using gradient elution (0% to 20% EtOAc/hexanes, 60 mL; 20% to 35% EtOAc/hexanes, 100 mL; 35% to 75% EtOAc/hexanes, 246 mL) to give the title compound. LCMS (ESI): m/z=364.2 [M+1]$^+$.

Step B: 4-{4-(Trifluoromethyl)-1-[7-(trifluoromethyl)quinolin-3-yl]cyclohexyl}phenol To phenol (52 mg, 0.55 mmol) dissolved in trifluoromethanesulfonic acid (0.60 mL) was added the title compound from the previous step (134 mg, 0.37 mmol). The mixture was stirred at room temperature for 16 h and quenched by slow addition of saturated aqueous NaHCO$_3$. The resulting mixture was extracted with EtOAc. The organic phase was concentrated and the residue was purified by silica gel chromatography eluting with a gradient of 0% to 60% EtOAc/hexanes to provide the title compound as a mixture of isomers. LCMS (ESI): m/z=440.3 [M+1]$^+$.

Step C: Butyl 4-{4-(trifluoromethyl)-1-[7-(trifluoromethyl)quinolin-3-yl]cyclohexyl}benzoate To an anhydrous solution of the title compound from the previous step (80 mg, 0.18 mmol) in CH$_2$Cl$_2$ (2 mL) were added pyridine (0.022 mL, 0.27 mmol) and trifluoromethanesulfonic anhydride (0.037 mL, 0.22 mmol). The mixture was stirred at room temperature for 20 min, quenched with water, and the crude product was extracted with EtOAc/hexanes. The organic phase was washed with H$_2$O (2×) and brine, then dried over Na$_2$SO$_4$, and passed through a short silica plug. The filtrate was concentrated to dryness. The crude triflate was taken up in w-butanol (1.5 mL) and to the slurry was added dichloro[1,1'-bis(diphenylphosphino)ferrocene]palladium(II), dichloromethane adduct (14 mg, 0.018 mmol), and DIEA (0.10 mL, 0.57 mmol). The reaction mixture was stirred under CO (balloon) at 90° C. for 1 h. The resulting mixture was concentrated and purified by flash chromatography on silica gel eluting with a gradient of 16% to 50% EtOAc/hexanes to give the title compound as a mixture of isomers.
LCMS (ESI): m/z=524.3 [M+1]$^+$.

Step D: N-(4-{4-(Trifluoromethyl)-1-[7-(trifluoromethyl)quinolin-3-yl]cyclohexyl}benzoyl)-β-alanine, Isomers A and B To the title compound from the previous step (25 mg, 0.05) dissolved in a mixture of dioxane (0.4 mL) and MeOH (0.4 mL) was added NaOH (0.4 mL of a 3N solution). The mixture was stirred at 60° C. for 1 h, allowed to cool to room temperature and acidified with 1 N aq. HCl. The aqueous phase was extracted with EtOAc, and the organic phase was washed with brine, dried over Na$_2$SO$_4$ and concentrated in vacuo: LCMS (ESI): m/z=468.1 [M+1]$^+$.

To the crude carboxylic acid obtained above were added EDC (20 mg, 0.10 mmol), HOBt (16 mg, 0.10 mmol) and β-alanine tert-butyl ester hydrochloride (19 mg, 0.10 mmol). The combined solids were dissolved in DMF (0.80 mL), DIEA (0.028 mL, 0.16 mmol) was added, and the reaction mixture was stirred at 50° C. for 1 h. The reaction mixture was quenched by addition of water and the aqueous phase was extracted with EtOAc. The organic phase was washed with brine, dried over $Na_2SO_4$ and concentrated in vacuo. The crude residue was then dissolved in $CH_2Cl_2$ (0.2 mL) and TFA (0.2 mL) was added. After 30 min, the mixture was concentrated in vacuo. Purification by reverse phase HPLC (30% to 100% $CH_3CN/H_2O$, each with 0.05% (v/v) of TFA) provided the title compounds, with Isomer A as the faster-eluting product and Isomer B as the slower-eluting product.

Isomer A: LCMS (ESI): m/z=539.2 $[M+H]^+$. $^1H$ NMR (500 MHz, $d_6$-Acetone): δ 9.08 (s, 1H), 8.77 (s, 1H), 8.37 (s, 1H), 8.31 (d, J=8.5 Hz, 1H), 7.89 (d, J=8.5 Hz, 1H), 7.82 (d, J=8.7 Hz, 2H), 7.78-7.73 (broad, 1H), 7.49 (d, J=6.9 Hz, 2H), 3.64-3.58 (m, 2H), 3.24 (d, J=13.5 Hz, 2H), 2.63 (t, J=6.9 Hz, 2H), 2.60-2.48 (m, 1H), 2.27 (d, J=13.9 Hz, 2H), 2.11-2.05 (m, 2H), 1.59 (quart, J=12.1 Hz, 2H).

Isomer B: LCMS (ESI): m/z=539.2 $[M+H]^+$. $^1H$ NMR (500 MHz, $d_6$-Acetone): δ 8.99 (s, 1H), 8.43 (s, 1H), 8.33 (s, 1H), 8.22 (d, J=8.5 Hz, 1H), 7.95 (d, J=8.8 Hz, 2H), 7.78-7.73 (m, 2H), 7.74 (d, J=8.7 Hz, 2H), 3.71-3.62 (m, 2H), 3.22 (d, J=13.3 Hz, 2H), 2.68 (t, J=6.8 Hz, 2H), 2.60-2.48 (m, 1H), 2.29 (d, J=13.9 Hz, 2H), 2.12-2.02 (m, 2H), 1.60 (quart, J=12.1 Hz, 2H).

EXAMPLE 19

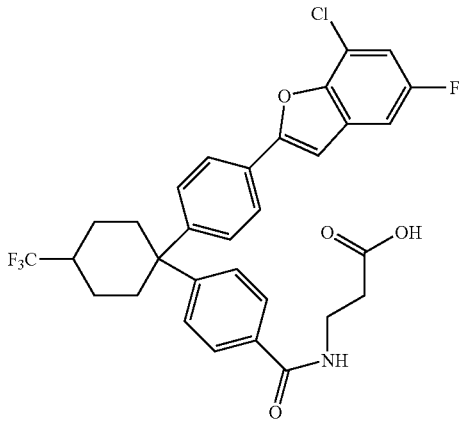

Step A: Methyl 4-(4-(trifluoromethyl)-1-{4-[(trimethylsilyl)ethynyl]phenyl}cyclohexyl)benzoate To a solution of the title compound from Example 2, step A (200 mg, 0.39 mmol) in 1.2 mL of DMF was added trimethylsilylacetylene (0.085 mL, 0.59 mmol), bis(triphenylphosphine)palladium (II) chloride (83 mg, 0.12 mmol) and triethylamine (0.27 mL, 2.0 mmol). The mixture was stirred at 70° C. under $N_2$ for 1 hour and then concentrated in vacuo. The residue was purified by flash chromatography on silica gel eluting with a gradient of 0% to 20% EtAOc/hexanes to provide the title compound. LC-MS (ESI): m/z=459.4 $[M+1]^+$.

Step B: 4-[1-(4-Ethynylphenyl)-4-(trifluoromethyl) cyclohexyl]benzoic acid

The title compound from the previous step (55 mg, 0.12 mmol) was dissolved in a mixture of 1,4-dioxane (2 mL) and LiOH (0.9 mL of a 1N solution). The mixture was stirred at 40° C. for 1 hour. The solvents were removed in vacuo. The residue was acidified with 2N HCl (2 mL) and the resultant mixture was extracted with ethyl acetate (3×2 mL). The combined organic layer was reduced in vacuo to provide the product as a brown solid. LC-MS (ESI, neg. ion): m/z=371.2 $[M-1]^-$.

Step C: tert-Butyl 3-({4-[1-(4-ethynylphenyl)-4-(trifluoromethyl)cyclohexyl]benzoyl}amino)propanoate To a solution of title compound from the previous step (44 mg, 0.118 mmol) in DMF (1 mL) was added β-alanine-tert-butyl ester hydrochloride (64 mg, 0.35 mmol), HOBt (54 mg, 0.35 mmol), EDC (91 mg, 0.47 mmol) and DIEA (0.31 mL, 1.8 mmol). The mixture was heated at 40° C. for 2 hours. The reaction mixture was diluted with 2 mL of ethyl acetate and washed with 2 mL of brine. The aqueous layer was extracted with ethyl acetate (2×2 mL). The organic layers were combined and dried over $Na_2SO_4$. The solvent was removed in vacuo and the title compound was purified by flash chromatography on silica using a gradient of 0% to 50% EtOAc/hexanes, then 50% to 80% EtOAc/hexanes to provide the title compound. LC-MS (ESI): m/z=444.4 $[M-tert-Bu+1]^+$.

Step D: tert-Butyl 3-({4-[1-[4-(7-chloro-5-fluoro-1-benzofuran-2-yl)phenyl]-4-(trifluoro-methyl)cyclohexyl]benzoyl}amino)propanoate To a solution title compound from the previous step (25 mg, 0.05 mmol) in DMF (0.5 mL was added 2-chloro-4-fluoro-6-iodophenol (27 mg, 0.1 mmol), bis(triphenylphosphine)palladium (II) dichloride (7 mg, 0.2 mmol), copper(I) iodide (1 mg, 0.1 mmol) and triethylamine (0.035 mL, 0.25 mmol) The reaction mixture was de-gassed in vacuo and was heated at 70° C. for 2 hours under $N_2$, then allowed to stand at ambient temperature for 16 h. Purification by reverse phase HPLC using a gradient of 45% to 100% $MeCN/H_2O$, both containing 0.1% TFA provided the title compound. LC-MS (ESI): m/z=588.1 $[M-tert-Bu+1]^+$.

Step E: 3-[({4-[1-[4-(7-Chloro-5-fluoro-1-benzofuran-2-yl)phenyl]-4-(trifluoromethyl)cyclohexyl] phenyl}carbonyl)amino]propanoic acid The title compound from the previous step (4.9 mg, 0.0076 mmol) was dissolved in a solution of 50% (v/v) TFA in DCM with 2% $H_2O$. The reaction mixture was allowed to stand at ambient temperature for 45 min. The solvents were removed in vacuo and the residue was purified by reverse phase HPLC (45% to 100% $MeCN/H_2O$, both containing 0.1% TFA). LC-MS (ESI): m/z=588.1 $[M+1]^+$. $^1H$ NMR (500 MHz, $CD_3OD$): δ (ppm) 7.82 (d, J=8.5 Hz, 2H), 7.77 (d, J=8.5 Hz, 2H), 7.57 (d, J=8.1 Hz, 2H), 7.38 (d, J=8.5 Hz, 2H), 7.26 (dd, J=8.6, 2.5 Hz, 1H), 7.19 (s, 1H), 7.13 (dd, J=8.9, 2.3 Hz, 1H), 3.63 (t, 3H), 2.95 (d, J=13.3 Hz, 2H), 2.63 (t, 2H), 2.34 (m, 1H), 2.09-1.93 (overlapping m, 5H), 1.48 (m, 3H).

The compounds in the following tables were prepared from Intermediates 1-11 using procedures similar to those described for Examples 1-19.

TABLE 1

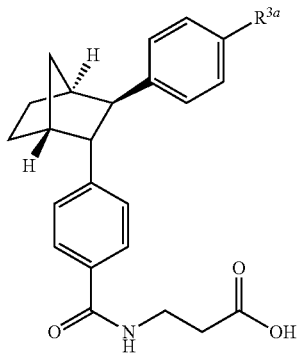

| Example | R³ᵃ | LC-MS |
|---|---|---|
| 20 | -O-CH₂-(benzothiazol-2-yl) | 527.2 (M + 1) |
| 21 | -O-CH₂-cyclohexyl | 476.4 (M + 1)<br>951.6 (2M + 1) |
| 22 | -O-CH₂-phenyl | 470.3 (M + 1)<br>939.5 (2M + 1) |
| 23 | -O-CH₂-(4-CF₃-phenyl) | 554.3 (M + 1) |
| 24 | -O-CH₂-(4-CF₃-phenyl) | 538.3 (M + 1) |
| 25 | -O-CH₂CH₂-phenyl | 484.3 (M + 1) |
| 26 | -O-(benzothiazol-2-yl) | 513.2 (M + 1) |
| 27 | -O-(4-Me-quinolin-2-yl) | 521.3 (M + 1) |
| 28 | -O-(4-tert-butyl-phenyl) | 512.4 (M + 1) |

TABLE 1-continued

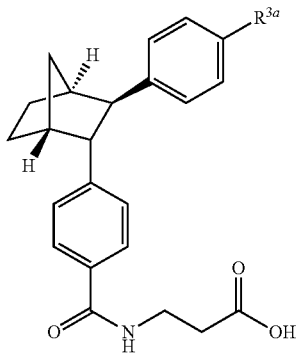

| Example | R³ᵃ | LC-MS |
|---|---|---|
| 29 | -O-(4-OCF₃-phenyl) | 540.3 (M + 1) |
| 30 | 4-tert-butyl-phenyl | 991.6 (2M + 1)<br>496.4 (M + 1) |
| 31 | 4-OCF₃-phenyl | 524.3 (M + 1) |
| 32 | 4-(pent-1-enyl)-phenyl | 891.5 (2M + 1)<br>446.3 (M + 1) |
| 33 | phenyl | 879.4 (2M + 1)<br>440.3 (M + 1) |
| 34 | 4-F-phenyl | 915.4 (2M + 1)<br>458.3 (M + 1) |
| 35 | -O-CH₂-(4-F-phenyl) | 975.3 (2M + 1)<br>448.2 (M + 1) |
| 36 | -O-CH₂-(4-Cl-phenyl) | 504.2 (M + 1) |
| 37 | -O-CH₂-(4-Br-phenyl) | 548.1 (M + 1)<br>550.3 (M + 1) |
| 38 | -O-CH₂-(3-CF₃-phenyl) | 538.2 (M + 1) |

TABLE 1-continued
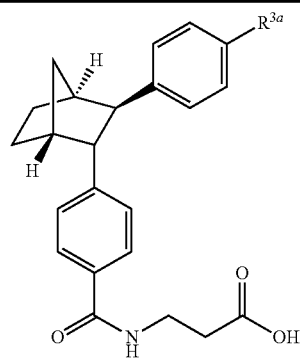 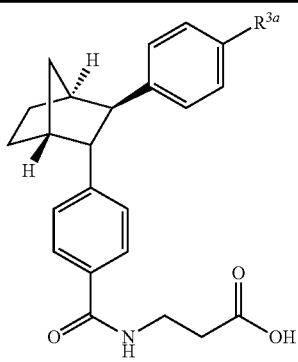
| Example | R³ᵃ | LC-MS | Example | R³ᵃ | LC-MS |
|---|---|---|---|---|---|
| 39 | -O-CH₂-(3-OCF₃-C₆H₄) | 554.1 (M + 1) | 49 | -O-CH₂-(4-tBu-C₆H₄) | 526.2 (M + 1) |
| 40 | -O-CH₂-(3,5-Cl₂-C₆H₃) | 538.2 (M + 1) 540.2 (M + 3) | 50 | -O-CH(CH₃)-C₆H₅ | 484.2 (M + 1) |
| 41 | -O-CH₂-(2-CF₃-C₆H₄) | 538.2 (M + 1) | 51 | -O-CH(CH₃)-C₆H₁₁ | 490.2 (M + 1) |
| 42 | 4-Me-C₆H₄- | 454.3 (M + 1) | 52 | -O-CH₂-(4-CN-C₆H₄) | 495.2 (M + 1) |
| 43 | 4-Cl-C₆H₄- | 474.2 (M + 1) | 53 | -O-CH₂-(4-OMe-C₆H₄) | 500.2 (M + 1) |
| 44 | 4-CF₃-C₆H₄- | 508.2 (M + 1) | 54 | -O-CH₂-(2,4-Cl₂-C₆H₃) | 538.1 (M + 1) 540.1 (M + 3) |
| 45 | -O-nBu | 436.2 (M + 1) | 55 | 3-CF₃-C₆H₄- | 508.2 (M + 1) |
| 46 | -O-CH₂-(2-Me-C₆H₄) | 484.3 (M + 1) | 56 | 3-OCF₃-C₆H₄- | 524.2 (M + 1) |
| 47 | -O-CH₂-(2-naphthyl) | 520.2 (M + 1) | 57 | 4-F-3-Me-C₆H₃- | 472.2 (M + 1) |
| 48 | -O-(1-tetralinyl) | 510.2 (M + 1) | | | |

TABLE 1-continued
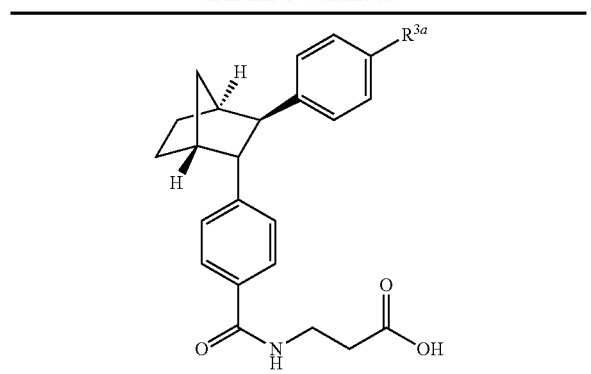
| Example | R³ᵃ | LC-MS |
|---|---|---|
| 58 | 2-MeO, 4-F phenyl | 488.2 (M + 1) |
| 59 | 4-OMe phenyl | 470.2 (M + 1) |
| 60 | 3,5-bis(CF₃) phenyl | 576.2 (M + 1) |
| 61 | 4-iPr phenyl | 482.2 (M + 1) |
| 62 | 4-OiPr phenyl | 498.2 (M + 1) |
| 63 | 3-OMe phenyl | 470.2 (M + 1) |
| 64 | 2-Cl phenyl | 474.2 (M + 1) |
| 65 | 3-Cl phenyl | 474.2 (M + 1) |
| 66 | 2-OCF₃ phenyl | 524.1 (M + 1) |
TABLE 1-continued
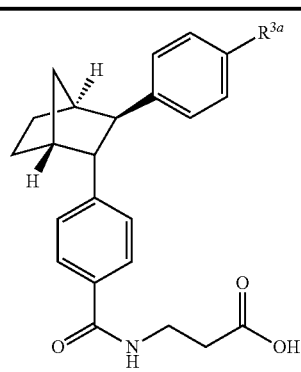
| Example | R³ᵃ | LC-MS |
|---|---|---|
| 67 | 3,5-diF phenyl | 476.2 (M + 1) |
| 68 | 2-F, 5-CF₃ phenyl | 526.2 (M + 1) |
| 69 | 4-OMe, 3-F phenyl | 488.2 (M + 1) |
| 70 | benzo[b]thiophen-2-yl | 496.2 (M + 1) |
| 71 | naphth-2-yl | 490.2 (M + 1) |
| 72 | 6-Cl-naphth-2-yl | 520.2 (M + 1) |
| 73 | -O-CH₂-(3-F-phenyl) | 975.4 (2M + 1) 488.3 (M + 1) |
| 74 | -O-CH₂-(3,4-diF-phenyl) | 506.3 (M + 1) |

TABLE 1-continued

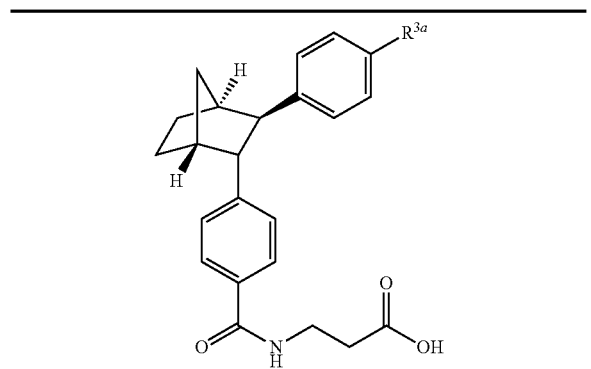

| Example | R³ᵃ | LC-MS |
|---|---|---|
| 75 | -OCH₂-(3,4-dichlorophenyl) | 538.2 (M + 1) 540.2 (M + 3) |
| 76 | -OCH₂-cyclobutyl | 895.5 (2M + 1) 448.4 (M + 1) |
| 77 | 2,4-dichlorophenyl | 508.1 (M + 1) |
| 78 | 3,4-difluorophenyl | 476.2 (M + 1) |
| 79 | 3-chloro-4-methoxyphenyl | 504.1 (M + 1) |
| 80 | 2,5-dichlorophenyl | 508.1 (M + 1) |
| 81 | naphthalen-1-yl | 490.2 (M + 1) |
| 82 | 4-nitrophenyl | 485.2 (M + 1) |
| 83 | benzofuran-2-yl | 480.2 (M + 1) |

TABLE 1-continued

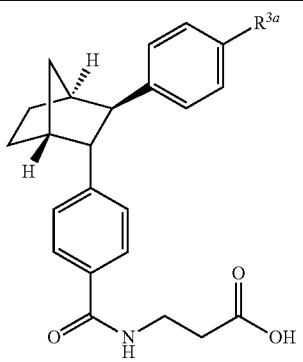

| Example | R³ᵃ | LC-MS |
|---|---|---|
| 84 | 2,4-difluorophenyl | 476.2 (M + 1) |
| 85 | 4-(dimethylamino)phenyl | 483.2 (M + 1) |
| 86 | -OCH₂-cyclopropyl | 434.2 (M + 1) |
| 87 | 3-fluoro-4-isopropoxyphenyl | 516.3 (M + 1) |
| 88 | 3-cyanophenyl | 465.2 (M + 1) |
| 89 | 1H-indazol-6-yl | 480.2 (M + 1) |
| 90 | 4-cyanophenyl | 645.2 (M + 1) |
| 91 | -OCH₂-cyclopentyl | 462.3 (M + 1) |
| 92 | -O-n-propyl | 422.3 (M + 1) |
| 93 | 4-(methylsulfonyl)phenyl | 518.3 (M + 1) |

TABLE 1-continued

| Example | R³ᵃ | LC-MS |
|---|---|---|
| 94 | 3,5-dimethylisoxazol-4-yl | 459.3 (M + 1) |
| 95 | -OCH₂-benzofurazan-5-yl | 512.3 (M + 1) |

TABLE 2

| Example | X | Y | R¹ᵃ | R²ᵃ | LC-MS m/z |
|---|---|---|---|---|---|
| 96 | H | H | -OCH₂-benzothiazol-2-yl | -HN-tetrazol-5-yl | 523.2 (M + 1) |
| 97 | H | H | 4-tert-butylphenyl | -HN-tetrazol-5-yl | 983.6 (2M + 1) 492.4 (M + 1) |
| 98 | H | H | 4-trifluoromethoxyphenyl | -HN-tetrazol-5-yl | 520.3 (M + 1) |
| 99 | H | H | hex-1-en-1-yl | -HN-tetrazol-5-yl | 883.5 (2M + 1) 442.3 (M + 1) |

TABLE 2-continued
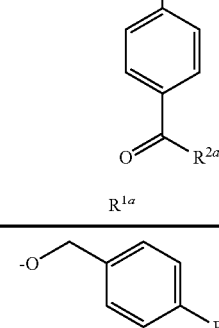
| Example | X | Y | R1a | R2a | LC-MS m/z |
|---------|---|---|-----|-----|-----------|
| 100 | Cl | Cl | 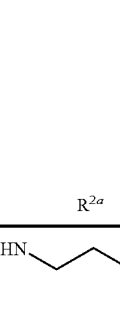 | 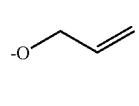 | 556.2 (M + 1)<br>558.2 (M + 3) |
| 101 | Cl | Cl | 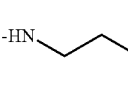 | 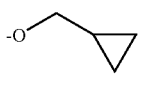 | 488.2 (M + 1)<br>490.2 (M + 3) |
| 102 | Cl | Cl | 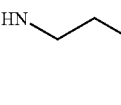 | 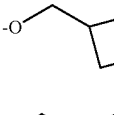 | 502.2 (M + 1)<br>504.2 (M + 3) |
| 103 | Cl | Cl | 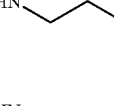 | 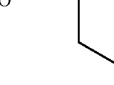 | 516.2 (M + 1)<br>518.2 (M + 3) |
| 104 | Cl | Cl |  | 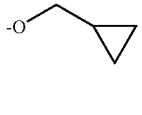 | 544.2 (M + 1)<br>546.1 (M + 3) |
| 105 | Cl | H | 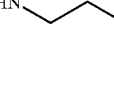 | 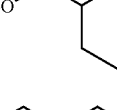 | 468.1 (M + 1) |
| 106 | Cl | H | 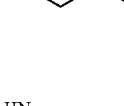 | 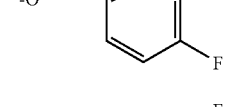 | 510.2 (M + 1) |
| 107 | Cl | H | 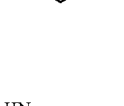 | 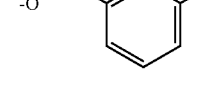 | 522.1 (M + 1) |
| 108 | Cl | H | 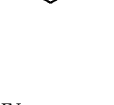 | 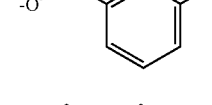 | 522.1 (M + 1) |
| 109 | Cl | Cl |  | 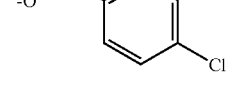 | 556.1 (M + 1)<br>558.0 (M + 3) |
| 110 | Cl | H |  | | 538.1 (M + 1) |

TABLE 2-continued

| Example | X | Y | R$^{1a}$ | R$^{2a}$ | LC-MS m/z |
|---|---|---|---|---|---|
| 111 | Cl | Cl | -O-CH$_2$-(4-Cl-phenyl) | -HN-CH$_2$CH$_2$-C(O)OH | 474.0 (M + 3)<br>472.0 (M + 1) |
| 112 | Cl | H | -O-CH$_2$-cyclopentyl | -HN-CH$_2$CH$_2$-C(O)OH | 496.2 (M + 1) |
| 113 | Cl | H | -O-propyl | -HN-CH$_2$CH$_2$-C(O)OH | 456.2 (M + 1) |
| 114 | Cl | H | 4-OCF$_3$-phenyl | -HN-CH$_2$CH$_2$-C(O)OH | 558.1 (M + 1) |
| 115 | Cl | H | 4-t-Bu-phenyl | -HN-CH$_2$CH$_2$-C(O)OH | 530.4 (M + 1) |
| 116 | —CH=CH$_2$ | H | -O-CH$_2$-cyclohexyl | -HN-CH$_2$CH$_2$-C(O)OH | 502.3 (M + 1) |
| 117 | —CH=CH$_2$ | —CH=CH$_2$ | -O-CH$_2$-cyclohexyl | -HN-CH$_2$CH$_2$-C(O)OH | 528.3 (M + 1) |
| 118 | Cl | Cl | -O-butyl | -HN-CH$_2$CH$_2$-C(O)OH | 504.2 (M + 1)<br>506.2 (M + 3) |
| 119 | Cl | Cl | -O-pentyl | -HN-CH$_2$CH$_2$-C(O)OH | 518.2 (M + 1)<br>520.2 (M + 3) |
| 120 | Cl | Cl | -O-CH$_2$CH$_2$-CH(CH$_3$)$_2$ | -HN-CH$_2$CH$_2$-C(O)OH | 518.2 (M + 1)<br>520.2 (M + 3) |
| 121 | Cl | Cl | -O-CH$_2$CH$_2$-CF$_3$ | -HN-CH$_2$CH$_2$-C(O)OH | 544.1 (M + 1)<br>546.1 (M + 3) |

TABLE 2-continued

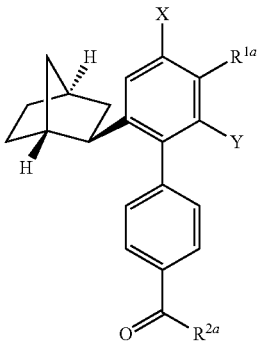

| Example | X | Y | R$^{1a}$ | R$^{2a}$ | LC-MS m/z |
|---|---|---|---|---|---|
| 122 | Cl | Cl | -O-(hexyl) | -HN-CH$_2$CH$_2$-C(O)OH | 532.2 (M + 1)<br>534.2 (M + 3) |

TABLE 3

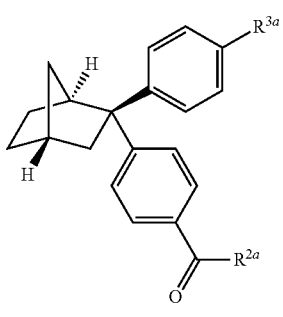

| Example | R$^{3a}$ | R$^{2a}$ | LC-MS m/z |
|---|---|---|---|
| 123 | -O-CH$_2$-(benzothiazol-2-yl) | -HN-(1H-tetrazol-5-yl) | 523.2 (M + 1) |
| 124 | -O-CH$_2$-(benzothiazol-2-yl) | -HN-CH$_2$CH$_2$-C(O)OH | 527.2 (M + 1) |
| 125 | -O-CH$_2$-cyclohexyl | -HN-CH$_2$CH$_2$-C(O)OH | 476.3 (M + 1) |
| 126 | 4-(OCF$_3$)phenyl | -HN-CH$_2$CH$_2$-C(O)OH | 524.2 (M + 1) |

TABLE 4

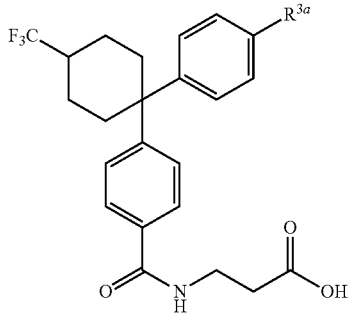

| Example | Isomer* | R$^{3a}$ | LC-MS |
|---|---|---|---|
| 127 | A | -O-CH$_2$-(4-fluorophenyl) | 544.3 (M + 1) |
| 128 | A | -O-CH$_2$-(3-fluorophenyl) | 544.3 (M + 1) |
| 129 | A | -O-CH$_2$-cyclohexyl | 532.3 (M + 1) |
| 130 | B | -O-CH$_2$-cyclohexyl | 532.3 (M + 1) |
| 131 | A | -O-CH$_2$-(2,4-dichlorophenyl) | 594.2 (M + 1) |
| 132 | B | -O-CH$_2$-(2,4-dichlorophenyl) | 594.2 (M + 1) |

TABLE 4-continued

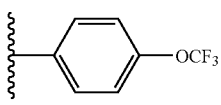

| Example | Isomer* | R³ᵃ | LC-MS |
|---|---|---|---|
| 133 | A | 4-OCF₃-phenyl | 580.3 (M + 1) |
| 134 | A | 4-Cl-phenyl | 530.3 (M + 1) |
| 135 | B | 4-Cl-phenyl | 530.3 (M + 1) |
| 136 | B | 4-OiPr-phenyl | 554.3 (M + 1) |
| 137 | B | 4-CF₃-phenyl | 564.3 (M + 1) |
| 138 | B | 4-tBu-phenyl | 552.3 (M + 1) |
| 139 | B | 3,4-diF-phenyl | 532.3 (M + 1) |
| 140 | B | benzofuran-2-yl | 536.3 (M + 1) |
| 141 | B | 2,4-diCl-phenyl | 564.2 (M + 1) |
| 142 | B | naphthalen-1-yl | 546.3 (M + 1) |
| 143 | B | 4-CN-phenyl | 521.3 (M + 1) |
| 144 | B | 4-SO₂Me-phenyl | 574.2 (M + 1) |
| 145 | B | 4-(pyrazol-1-yl)-phenyl | 562.4 (M + 1) |
| 146 | B | 4-NO₂-phenyl | 541.3 (M + 1) |
| 147 | B | cyclohexen-1-yl | 500.3 (M + 1) |
| 148 | B | cyclohexyl | 502.4 (M + 1) |
| 149 | B | hex-1-en-1-yl | 502.4 (M + 1) |
| 150 | B | 6-OMe-naphthalen-2-yl | 576.4 (M + 1) |
| 151 | B | 3-Cl-4-OMe-phenyl | 560.3 (M + 1) |
| 152 | B | 4-Me-phenyl | 510.3 (M + 1) |
| 153 | B | 4-Et-phenyl | 524.3 (M + 1) |

TABLE 4-continued

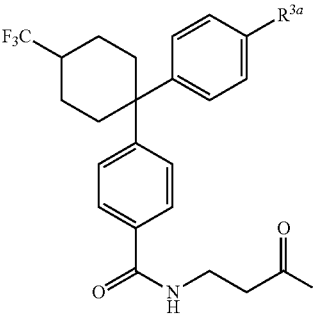

| Example | Isomer* | R³ᵃ | LC-MS |
|---|---|---|---|
| 154 | B | 4-isopropylphenyl | 538.4 (M + 1) |
| 155 | B | 3-chlorophenyl | 530.3 (M + 1) |
| 156 | B | 3,4-dichlorophenyl | 564.3 (M + 1) |
| 157 | B | 2,3-difluorophenyl | 532.4 (M + 1) |
| 158 | B | 2,5-dichlorophenyl | 564.3 (M + 1) |
| 159 | B | quinolin-3-yl | 547.4 (M + 1) |
| 160 | B | quinolin-5-yl | 547.3 (M + 1) |
| 161 | B | 3,5-dimethylisoxazol-4-yl | 515.4 (M + 1) |
| 162 | B | -O-CH₂-(pyridin-2-yl) | 527.2 (M + 1) |
| 163 | B | -O-CH₂-(pyridin-3-yl) | 527.2 (M + 1) |
| 164 | B | -O-CH₂-(5-CF₃-furan-2-yl) | 584.2 (M + 1) |
| 165 | B | -O-CH₂-(quinolin-8-yl) | 577.2 (M + 1) |
| 166 | B | -O-CH₂-(benzothiazol-2-yl) | 583.2 (M + 1) |
| 167 | B | 4-fluoro-2-methoxyphenyl | 544.4 (M + 1) |
| 168 | B | 6-fluoropyridin-3-yl | 515.4 (M + 1) |
| 169 | B | 6-chloronaphthalen-2-yl | 580.1 (M + 1) |
| 170 | B | 6-methoxypyridin-3-yl | 527.4 (M + 1) |

TABLE 4-continued

[Structure: F3C-cyclohexyl-C(phenyl-R3a)(phenyl-C(O)NH-CH2CH2-COOH)]

| Example | Isomer* | R3a | LC-MS |
|---|---|---|---|
| 171 | B | 2-MeO, 4-Cl-phenyl | 560.4 (M + 1) |
| 172 | B | 2-F, 5-OMe-phenyl | 544.4 (M + 1) |
| 173 | B | 4-(iPrS)-phenyl | 570.4 (M + 1) |
| 174 | B | 3-Cl, 4-OCF3-phenyl | 614.3 (M + 1) |
| 175 | B | benzothiazol-2-yl | 553.3 (M + 1) |
| 176 | B | indazol-1-yl | 536.4 (M + 1) |
| 177 | B | indazol-2-yl | 536.3 (M + 1) |
| 178 | B | benzo[1,2,5]thiadiazol-5-yl | 554.4 (M + 1) |
| 179 | B | benzothiophen-2-yl | 552.4 (M + 1) |
| 180 | B | benzo[1,2,5]oxadiazol-5-yl | 538.4 (M + 1) |
| 181 | B | 3-iPr-phenyl | 538.4 (M + 1) |
| 182 | B | 4-(iPrS(O))-phenyl | 586.4 (M + 1) |
| 183 | B | 4-(iPrSO2)-phenyl | 602.4 (M + 1) |
| 184 | B | 2-methyl-1,2,3,4-tetrahydroisoquinolin-N-yl | Neg. ion: 549.4 (M − 1)− |
| 185 | B | 5-F, 2-MeO-phenyl | 544.4 (M + 1) |
| 186 | B | 3-F, 6-CF3-phenyl | 582.4 (M + 1) |

TABLE 4-continued

[Structure: 4-(trifluoromethyl)cyclohexyl group bearing two phenyl substituents; one phenyl bears R³ᵃ, the other is a 4-substituted phenyl connected to C(=O)NH-CH₂CH₂-COOH]

| Example | Isomer* | R³ᵃ | LC-MS |
|---|---|---|---|
| 187 | B | 5-Cl, 2-EtO-phenyl | 574.4 (M + 1) |
| 188 | B | 5-chloro-1H-indol-2-yl | Neg. ion: 567.4 (M − 1)⁻ |
| 189 | B | 5-tBu-1,3,4-oxadiazol-2-yl | 544.4 (M + 1) |
| 190 | B | 3-Cl, 4-CF₃-phenyl | 598.4 (M + 1) |
| 191 | B | 4-Cl, 2-EtO-phenyl | 574.4 (M + 1) |
| 192 | B | 3-Cl, 4-OPr-phenyl | 588.4 (M + 1) |
| 193 | B | 6-chloropyridin-3-yl | 531.1 (M + 1) |
| 194 | B | 2,5-di-OMe-phenyl | 556.4 (M + 1) |
| 195 | B | 4-OMe-phenyl | 526.4 (M + 1) |
| 196 | B | 3-OMe-phenyl | 526.4 (M + 1) |
| 197 | B | 2-OMe-pyridin-3-yl | 527.1 (M + 1) |
| 198 | B | 2-F-pyridin-3-yl | 515.4 (M + 1) |
| 199 | B | 2-OMe-pyrimidin-5-yl | 528.1 (M + 1) |
| 200 | B | 2-Br, 5-OMe-pyridin-4-yl | 605.1 (M + 1) |
| 201 | B | 6-CF₃-pyridin-2-yl | 565.2 (M + 1) |
| 202 | B | benzoxazol-2-yl | 537.1 (M + 1) |
| 203 | B | 5-CF₃-pyridin-2-yl | 565.2 (M + 1) |
| 204 | B | 3-Cl, 5-Me-phenyl | 544.4 (M + 1) |

TABLE 4-continued

Structure (Examples 205-212):
4-(trifluoromethyl)cyclohexyl and 4-R³ᵃ-phenyl disubstituted at a quaternary carbon, linked to a 4-phenyl group bearing a C(=O)NH-CH₂CH₂-C(=O)OH substituent.

| Example | Isomer* | R³ᵃ | LC-MS |
|---|---|---|---|
| 205 | B | 3-chloro-2-methylphenyl | 544.4 (M + 1) |
| 206 | B | 2-chloropyridin-3-yl | 531.4 (M + 1) |
| 207 | B | 2-chloropyridin-4-yl | 531.4 (M + 1) |
| 208 | B | 5-chloro-2-fluorophenyl | 548.4 (M + 1) |
| 209 | B | 3-chloro-2-fluorophenyl | 548.4 (M + 1) |
| 210 | B | 2,3-dichlorophenyl | 564.4 (M + 1) |
| 211 | B | 2,6-dimethoxypyridin-3-yl | 557.4 (M + 1) |
| 212 | B | 5-methoxy-1H-indol-2-yl | Neg. ion: 563.4 (M − 1)⁻ |
| 213 | B | 5-cyano-1H-indol-2-yl | Neg. ion: 58.3 (M − 1)⁻ |
| 214 | B | 2-fluoro-5-methoxypyridin-3-yl | 545.4 (M + 1) |
| 215 | B | 2,5-dichloropyridin-3-yl | 565.3 (M + 1) |
| 216 | B | 4-chloro-2-(trifluoromethoxy)phenyl | 614.4 (M + 1) |
| 217 | B | 2-methoxy-5-methylphenyl | 540.5 (M + 1) |
| 218 | B | 5-chloro-2-methoxypyridin-3-yl | 561.4 (M + 1) |
| 219 | B | 2-fluoro-3-methoxyphenyl | 544.4 (M + 1) |

TABLE 4-continued

| Example | Isomer* | R³ᵃ | LC-MS |
|---|---|---|---|
| 220 | B | 2-Cl, 5-CF₃ phenyl | 598.4 (M + 1) |
| 221 | B | 1H-indazol-1-yl | 540.5 (M + 1) |
| 222 | B | 6-Cl-benzoxazol-2-yl | 571.3 (M + 1) |
| 223 | B | 5-Cl, 2-PrO phenyl | 588.4 (M + 1) |
| 224 | B | 4-Cl, 2-MeO phenyl | 560.4 (M + 1) |
| 225 | B | 5-Me-furo[2,3-b]pyridin-2-yl | 551.4 (M + 1) |
| 226 | B | 6-CF₃-pyridin-3-yl | 565.4 (M + 1) |
| 227 | B | 5-isopropyl, 2-MeO phenyl | 568.5 (M + 1) |
| 228 | B | 7-CF₃-1,2,3,4-tetrahydroquinolin-1-yl | 619.5 (M + 1) |
| 229 | B | 6-Me-1,2,3,4-tetrahydroquinolin-1-yl | 565.5 (M + 1) |
| 230 | B | 6-OMe-1,2,3,4-tetrahydroquinolin-1-yl | 581.5 (M + 1) |
| 231 | B | 6-(dimethylamino)pyridin-3-yl | 540.5 (M + 1) |
| 232 | B | 5-CF₃-benzofuran-2-yl | 604.2 (M + 1) |
| 233 | B | 5-CN-benzofuran-2-yl | 561.2 (M + 1) |
| 234 | B | 5-CF₃, 2-MeO phenyl | 594.4 (M + 1) |

TABLE 4-continued
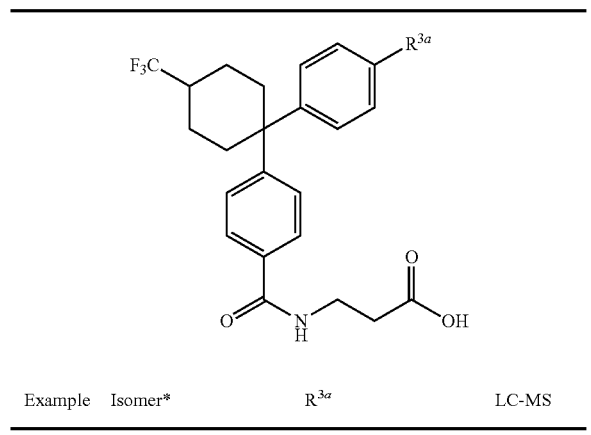
| Example | Isomer* | R³ᵃ | LC-MS |
|---|---|---|---|
| 235 | B | 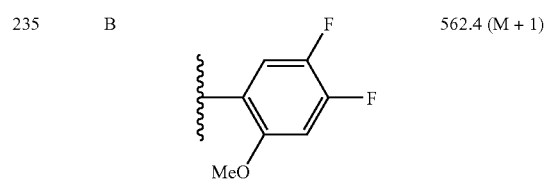 | 562.4 (M + 1) |
| 236 | B | 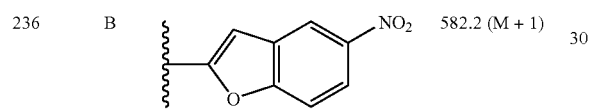 | 582.2 (M + 1) |
| 237 | B | 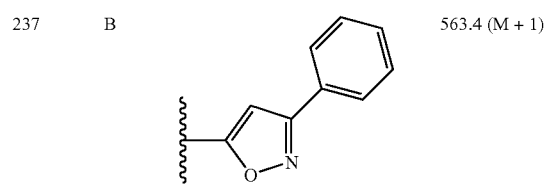 | 563.4 (M + 1) |
| 238 | B | 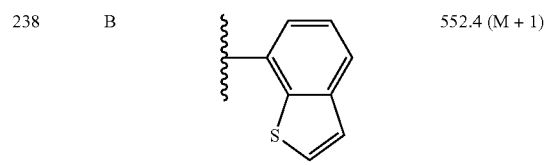 | 552.4 (M + 1) |
| 239 | B | 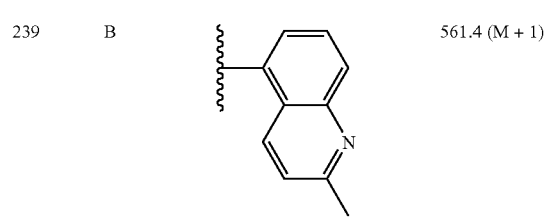 | 561.4 (M + 1) |
*Isomer A corresponds to the product derived from Intermediate 5, Isomer A; Isomer B corresponds to the product derived from Intermediate 5, Isomer B.
TABLE 5
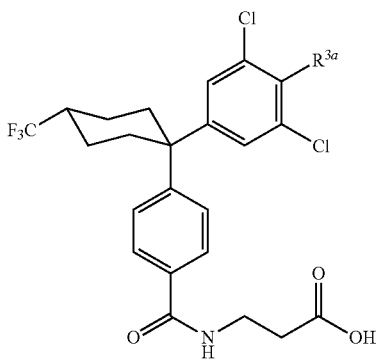
| Example | R³ᵃ | LC-MS |
|---|---|---|
| 240 | 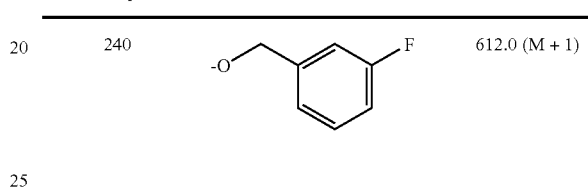 | 612.0 (M + 1) |
| 241 | 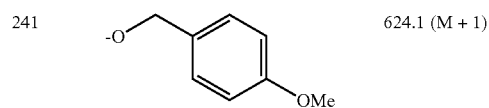 | 624.1 (M + 1) |
| 242 | 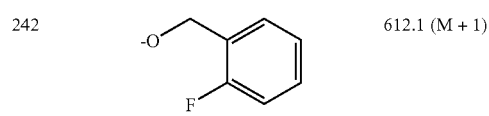 | 612.1 (M + 1) |
| 243 | 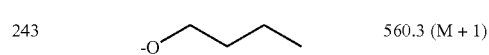 | 560.3 (M + 1) |
| 244 | 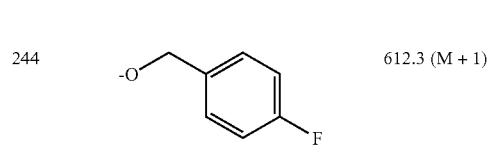 | 612.3 (M + 1) |
| 245 | 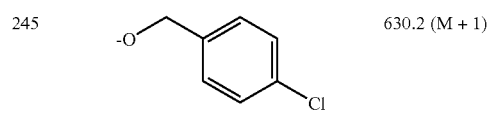 | 630.2 (M + 1) |
| 246 | 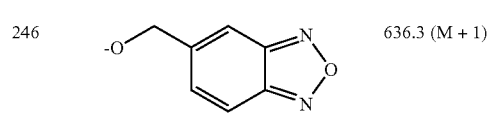 | 636.3 (M + 1) |

TABLE 6

[Structure: 4-(trifluoromethyl)cyclohexyl group attached to carbon bearing a phenyl-C(O)NH-CH2CH2-COOH chain and a pyridine with R³ᵃ substituent]

| Example | Isomer* | R³ᵃ | LC-MS |
|---|---|---|---|
| 247 | A | 5-chloro-2-methoxyphenyl | 561.3 (M + 1) |
| 248 | B | 5-chloro-2-methoxyphenyl | 561.3 (M + 1) |
| 249 | A | 4-chlorophenyl | 531.3 (M + 1) |
| 250 | B | 4-chlorophenyl | 531.3 (M + 1) |
| 251 | B | benzofuran-2-yl | 537.3 (M + 1) |
| 252 | B | 4-(trifluoromethoxy)phenyl | 581.4 (M + 1) |
| 253 | B | 2,4-dichlorophenyl | 565.3 (M + 1) |
| 254 | B | 4-(isopropylthio)phenyl | 571.4 (M + 1) |
| 255 | B | 3,5-dichlorophenyl | 565.3 (M + 1) |

TABLE 6-continued

| Example | Isomer* | R³ᵃ | LC-MS |
|---|---|---|---|
| 256 | B | 6-methoxynaphthalen-2-yl | 577.4 (M + 1) |
| 257 | B | 5-chloro-1H-indol-2-yl | 570.3 (M + 1) |
| 258 | B | 3-chloro-4-(trifluoromethyl)phenyl | 599.3 (M + 1) |
| 259 | B | 4-(trifluoromethyl)phenyl | 565.3 (M + 1) |
| 260 | B | 4-tert-butylphenyl | 553.3 (M + 1) |
| 261 | B | 5-chloro-4-methoxyphenyl | 561.3 (M + 1) |
| 262 | B | 3,5-bis(trifluoromethyl)phenyl | 633.6 (M + 1) |
| 263 | B | benzothiophen-2-yl | 553.3 (M + 1) |
| 264 | B | 6-chloronaphthalen-2-yl | 581.6 (M + 1) |

TABLE 6-continued

Structure: 4-(trifluoromethyl)cyclohexyl group attached to a pyridine bearing R³ᵃ and to a phenyl group, with a -C(O)NH-CH₂CH₂-COOH substituent.

| Example | Isomer* | R³ᵃ | LC-MS |
|---|---|---|---|
| 265 | B | 7-chloroquinolin-3-yl | 582.3 (M + 1) |
| 266 | B | 7-(trifluoromethyl)quinolin-3-yl | 616.4 (M + 1) |
| 267 | B | 6-(trifluoromethoxy)naphthalen-2-yl | 631.3 (M + 1) |
| 268 | B | quinolin-3-yl | 548.2 (M + 1) |
| 269 | B | naphthalen-2-yl | 547.4 (M + 1) |
| 270 | B | quinolin-7-yl | 548.3 (M + 1) |

*Isomer A corresponds to the product derived from Intermediate 10, Isomer A. Isomer B corresponds to the product derived from Intermediate 10, Isomer B.

TABLE 7

Structure: 4-(trifluoromethyl)cyclohexyl group attached to a naphthalene bearing R³ᵃ and to a phenyl group with -C(O)NH-CH₂CH₂-COOH substituent.

| Example | Isomer* | R³ᵃ | LC-MS |
|---|---|---|---|
| 271 | A | —OMe | 500.3 (M + 1) |
| 272 | B | —OMe | 500.3 (M + 1) |
| 273 | A | 4-(trifluoromethoxy)phenyl | Neg. ion: 629.2 (M − 1) |
| 274 | A | —O-cyclopentyl | 554.4 (M + 1) |
| 275 | A | —O-isobutyl | 542.4 (M + 1) |

TABLE 7-continued
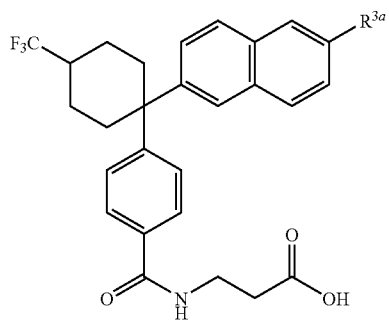
| Example | Isomer* | R³ᵃ | LC-MS |
|---|---|---|---|
| 276 | A | 4-OMe, 3-Cl phenyl | 610.4 (M + 1) |
| 277 | A | benzofuran-2-yl | 586.3 (M + 1) |
| 278 | A | 2,5-dichlorophenyl | 614.2 (M + 1) |
| 279 | A | -OEt | 514.3 (M + 1) |
| 280 | A | -OiPr | 528.3 (M + 1) |
| 281 | A | -OCH₂(3-F-phenyl) | 594.4 (M + 1) |
| 282 | A | -O-n-butyl | 542.1 (M + 1) |
| 283 | A | -O-n-pentyl | 556.5 (M + 1) |
| 284 | A | -O-n-propyl | 528.3 (M + 1) |
| 285 | A | 3-OCF₃ phenyl | Poor ionization: ¹H NMR of aromatic region (500 MHz, acetone-d₆): δ 8.20 (s, 1H), 8.08 (br, 2H), 8.00 (d, J = 8.7 Hz, 1H), 7.93-7.85 (m, 5H), 7.80 (t, 1H), 7.74 (m, 2H), 7.65 (d, J = 8.5 Hz, 2H), 7.45 (dd, J = 8.7, 2.1 Hz, 1H). |
| 286 | A | -OCH₂(3-CF₃-phenyl) | 644.4 (M + 1) |

TABLE 7-continued
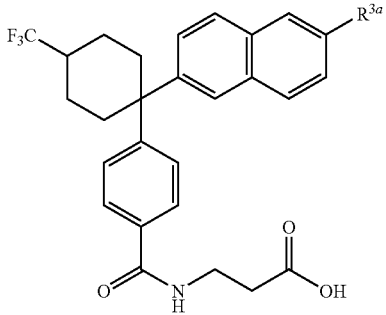
| Example | Isomer* | R³ᵃ | LC-MS |
|---|---|---|---|
| 287 | A | -O-CH2-(3,4-difluorophenyl) | 612.2 (M + 1) |
| 288 | A | 3-Cl-4-CF3-phenyl | 648.3 (M + 1) |
| 289 | A | 3,4-difluorophenyl | 582.6 (M + 1) |
| 290 | A | 5-chloro-1H-indol-2-yl | 619.2 (M + 1) |
| 291 | A | 3,4-dichlorophenyl | 614.2 (M + 1) |
| 292 | A | -O-CH2-(3-OCF3-phenyl) | 660.2 (M + 1) |
| 293 | A | -O-CH2-cyclobutyl | 554.3 (M + 1) |
| 294 | A | -O-CH2-(3-Cl-phenyl) | 610.2 (M + 1) |
| 295 | A | -O-CH2-cyclohexyl | 582.3 (M + 1) |
| 296 | A | 6-chloropyridin-3-yl | 581.4 (M + 1) |

TABLE 7-continued
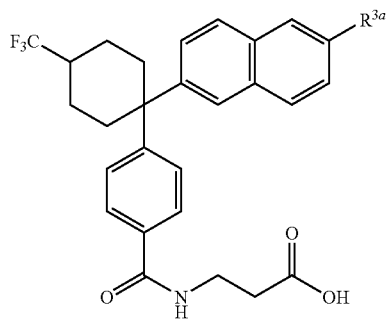
| Example | Isomer* | R³ᵃ | LC-MS |
|---|---|---|---|
| 297 | A | 2-chloropyridin-3-yl | 581.4 (M + 1) |
| 298 | A | 3,5-difluorophenyl | 582.4 (M + 1) |
| 299 | A | 3-chloro-4-fluorophenyl | 598.3 (M + 1) |
| 300 | A | 2-chloropyridin-4-yl | 581.5 (M + 1) |
| 301 | A | 4-chloro-3-(trifluoromethyl)phenyl | 648.2 (M + 1) |
| 302 | A | 3,5-dichlorophenyl | 614.2 (M + 1) |
| 303 | A | 2,3-dichlorophenyl | 614.1 (M + 1) |
| 304 | A | 3-fluorophenyl | 564.2 (M + 1) |

TABLE 7-continued
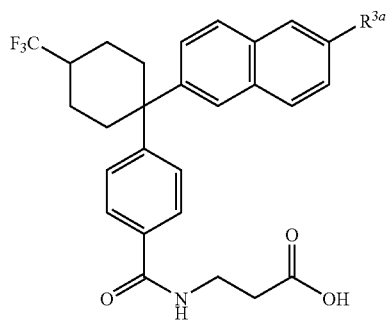
| Example | Isomer* | R³ᵃ | LC-MS |
|---|---|---|---|
| 305 | A | -O-CH₂-(5-(2-chloropyridyl)) | 610.3 (M + 1) |
| 306 | A | 5-(2-methoxypyridyl) | 577.4 (M + 1) |
| 307 | A | -CH₂-(3-fluorophenyl) | 592.3 (M + 1) |
| 308 | A | -pentyl | 540.3 (M + 1) |
| 309 | A | -CH₂-cyclohexyl | Neg. ion: 578.5 (M − 1) |
| 310 | A | 5-(2-methoxypyrimidyl) | 579.6 (M + 1) |
| 311 | A | 4-(3-fluoropyridyl) | 565.7 (M + 1) |
| 312 | A | 5-(2-dimethylaminopyridyl) | 590.7 (M + 1) |
| 313 | A | 4-(2-methoxy-5-fluoropyridyl) | 595.7 (M + 1) |
| 314 | A | 3-chlorophenyl | 580.0 (M + 1) |

TABLE 7-continued
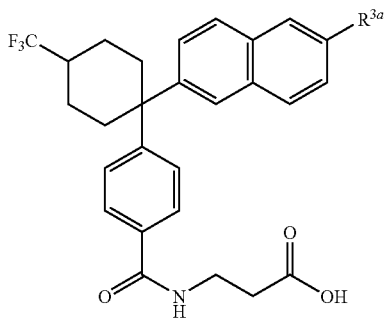
| Example | Isomer* | $R^{3a}$ | LC-MS |
|---|---|---|---|
| 315 | A | 2-F, 3-Me-phenyl | 578.5 (M + 1) |
| 316 | A | 4-isopropylphenyl | 588.2 (M + 1) |
| 317 | A | 1-methyl-1H-pyrazol-4-yl | 550.4 (M + 1) |
| 318 | A | thiophen-3-yl | 552.3 (M + 1) |
| 319 | A | furan-3-yl | 536.2 (M + 1) |
| 320 | A | 3,5-dimethylisoxazol-4-yl | 565.4 (M + 1) |
| 321 | A | cyclopentyl | 538.3 (M + 1) |
| 322 | A | cyclohexyl | 552.3 (M + 1) |
| 323 | A | —OCF$_2$H | 536.1 (M + 1) |
*Isomer A corresponds to the product derived from Intermediate 8, Isomer A.
Isomer B corresponds to the product derived from Intermediate 8, Isomer B.

TABLE 8
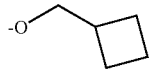
| Example | Isomer* | R³ᵃ | LC-MS |
|---|---|---|---|
| 324 | A | —OMe | 501.3 (M + 1) |
| 325 | B | —OMe | 501.3 (M + 1) |
| 326 | A | —OPr | 529.3 (M + 1) |
| 327 | B | —OPr | 529.2 (M + 1) |
| 328 | A | —OBu | 543.3 (M + 1) |
| 329 | B | —OBu | 543.3 (M + 1) |
| 330 | A | 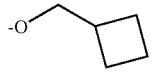 | 555.4 (M + 1) |
| 331 | B | 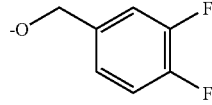 | 555.4 (M + 1) |
| 332 | A | 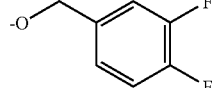 | 613.4 (M + 1) |
| 333 | B | 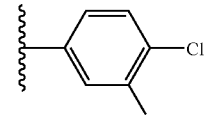 | 613.3 (M + 1) |
| 334 | A | 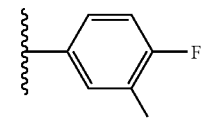 | 615.2 (M + 1) |
| 335 | A | 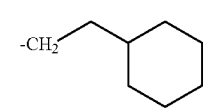 | 583.2 (M + 1) |
| 336 | A | 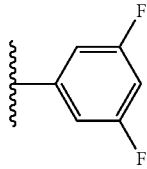 | 581.3 (M + 1) |
| 337 | A | -n-pentyl | 541.3 (M + 1) |
| 338 | A | -n-hexyl | 555.4 (M + 1) |
| 339 | A | 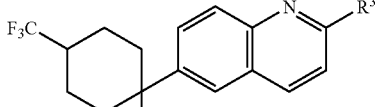 | 583.3 (M + 1) |
TABLE 8-continued
| Example | Isomer* | R³ᵃ | LC-MS |
|---|---|---|---|
| 340 | A | 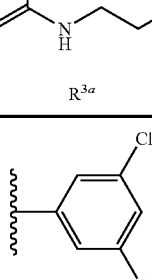 | 615.2 (M + 1) |
| 341 | A | 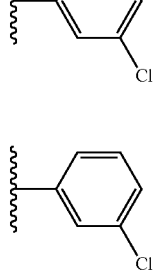 | 581.3 (M + 1) |
| 342 | A | 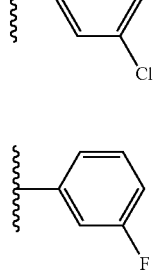 | 565.2 (M + 1) |
| 343 | A | 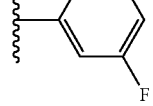 | 529.3 (M + 1) |
| 344 | A |  | 555.3 (M + 1) |
| 345 | A |  | 593.3 (M + 1) |
| 346 | A | 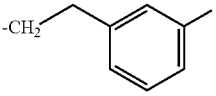 | 575.3 (M + 1) |
| 347 | A | 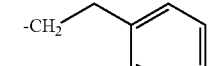 | 593.3 (M + 1) |

TABLE 8-continued
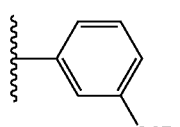
| Example | Isomer* | R³ᵃ | LC-MS |
|---|---|---|---|
| 348 | A | 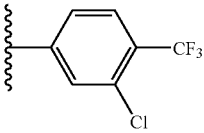 | 631.4 (M + 1) |
| 349 | A | 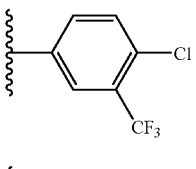 | 649.3 (M + 1) |
TABLE 8-continued
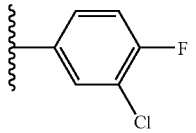
| Example | Isomer* | R³ᵃ | LC-MS |
|---|---|---|---|
| 350 | A | 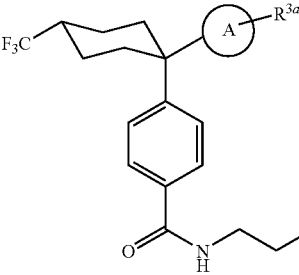 | 649.4 (M + 1) |
| 351 | A | 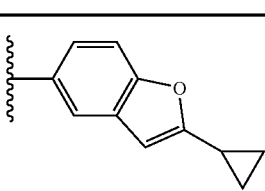 | 599.4 (M + 1) |
*Isomer A corresponds to the product derived from Intermediate 9, Isomer A.
Isomer B corresponds to the product derived from Intermediate 9, Isomer B.
TABLE 9
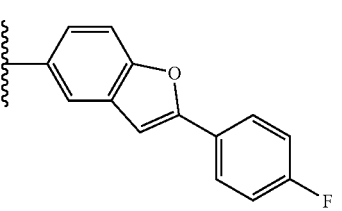
| Example | A—R³ᵃ | LC-MS |
|---|---|---|
| 352 | (5-(2-cyclopropylbenzofuran-5-yl)) | 500.2 (M + 1) |
| 353 | (5-(2-(4-fluorophenyl)benzofuran-5-yl)) | 554.2 (M + 1) |

TABLE 9-continued
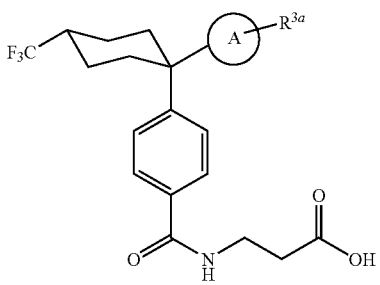
| Example | A—R³ᵃ | LC-MS |
|---|---|---|
| 354 | 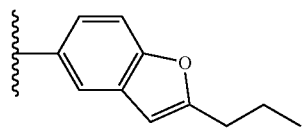 | 502.1 (M + 1) |
| 355 | 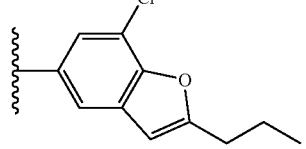 | 536.1 (M + 1) |
| 356 | 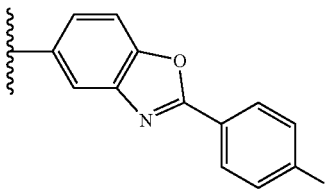 | 555.3 (M + 1) |
| 357 | 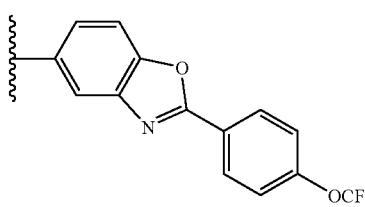 | 621.3 (M + 1) |
| 358 | 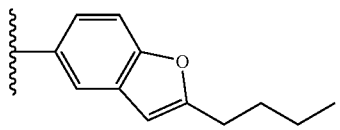 | 516.3 (M + 1) |
| 359 | 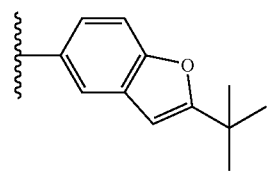 | 516.2 (M + 1) |
| 360 | 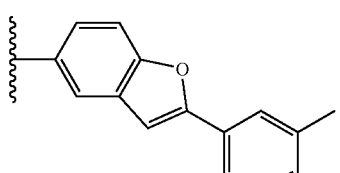 | 564.2 (M + 1) |

TABLE 9-continued
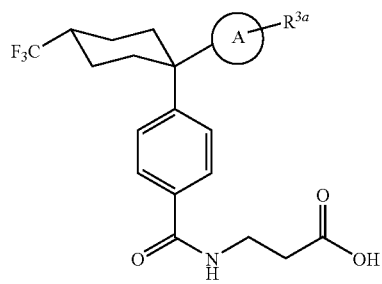
| Example | A—R³ᵃ | LC-MS |
|---|---|---|
| 361 | 5-(2-methoxyphenyl)benzofuran-5-yl | 566.2 (M + 1) |
| 362 | 1,3-dichloro-2-butoxynaphthalen-6-yl | 625.3 (M + 23) |
| 363 | 2-cyclohexylbenzofuran-5-yl | 542.4 (M + 1) |
| 364 | 2-(3-fluorophenyl)benzofuran-5-yl | 554.4 (M + 1) |
| 365 | 3,4-dipropyl-2-oxo-2H-chromen-6-yl | 572.5 (M + 1) |
| 366 | 7-chloro-2-(4-fluorophenyl)benzofuran-5-yl | 588.2 (M + 1) |

TABLE 9-continued
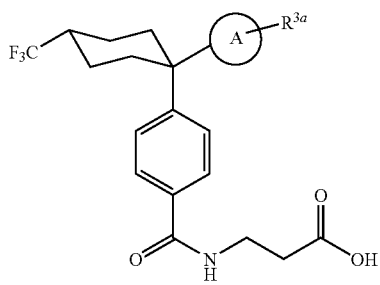
| Example | 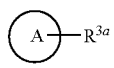 | LC-MS |
|---|---|---|
| 367 | 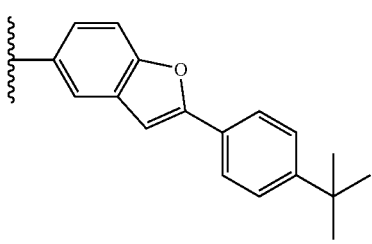 | 592.3 (M + 1) |
| 368 | 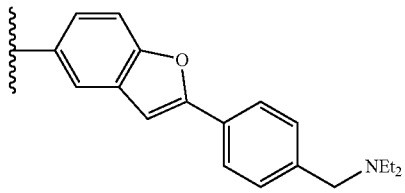 | 545.3 (M + 1) |
| 369 | 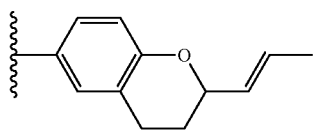 | 516.3 (M + 1) |
| 370 | 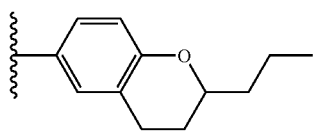 | 518.3 (M + 1) |
| 371 | 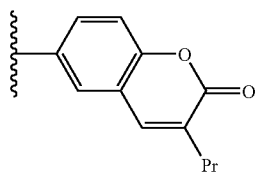 | 530.1 (M + 1) |
| 372 | 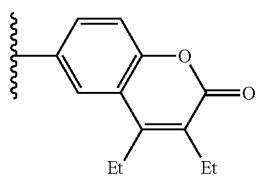 | 544.1 (M + 1) |

TABLE 10
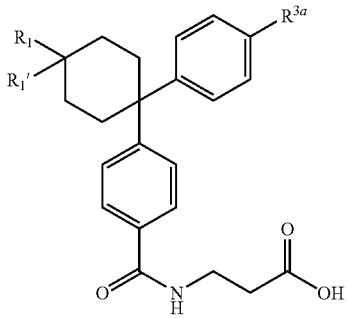
| Example | Isomer | R¹, R¹' | R³ᵃ | LC-MS |
|---|---|---|---|---|
| 373 | A* | H, t-Bu | 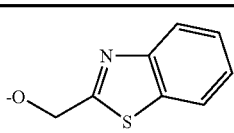 -O-CH₂-(benzothiazol-2-yl) | 571.1 (M + 1) |
| 374 | B* | H, t-Bu | 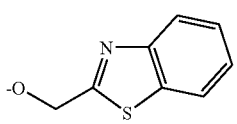 -O-CH₂-(benzothiazol-2-yl) | 571.1 (M + 1) |
| 375 | A* | H, Ph | 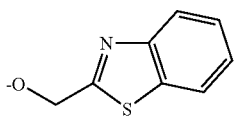 -O-CH₂-(benzothiazol-2-yl) | 591.1 (M + 1) |
| 376 | B* | H, Ph | 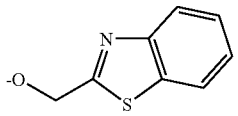 -O-CH₂-(benzothiazol-2-yl) | 591.1 (M + 1) |
| 377 | | Me, Me | 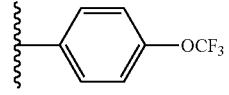 4-OCF₃-phenyl | 540.2 (M + 1) |
| 378 | A* | H, t-Bu | 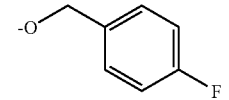 -O-CH₂-(4-F-phenyl) | 532.2 (M + 1) |
| 379 | B* | H, t-Bu | 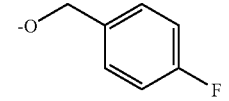 -O-CH₂-(4-F-phenyl) | 532.2 (M + 1) |
| 380 | B** | H, t-Bu | 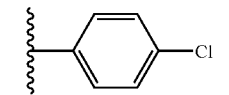 4-Cl-phenyl | 518.2 (M + 1) |
| 381 | A** | H, t-Bu | 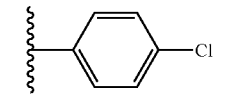 4-Cl-phenyl | 518.2 (M + 1) |
| 382 | A*** | H, t-Bu | 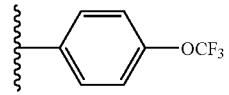 4-OCF₃-phenyl | 568.4 (M + 1) |

TABLE 10-continued

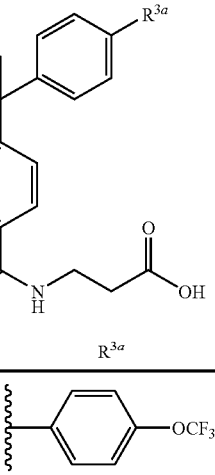

| Example | Isomer | R¹, R¹' | R³ᵃ | LC-MS |
|---|---|---|---|---|
| 383 | B*** | H, t-Bu | 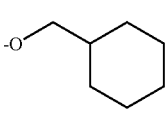 | 568.4 (M + 1) |
| 384 | B** | H, t-Bu | 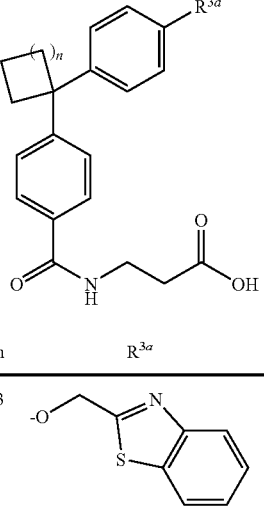 | 520.4 (M + 1) |

*Isomer A is the faster-eluting isomer and Isomer B is the slower-eluting isomer by reverse-phase HPLC (C18, MeCN/H₂O gradient, each containing 1% (v/v) of TFA)
**Isomer A is the faster-eluting isomer and Isomer B is the slower-eluting isomer by chiral HPLC (OJ column, 10% EtOH/heptane)
***Isomer A is the faster-eluting isomer and Isomer B is the slower-eluting isomer by chiral HPLC (OC column, 10% EtOH/heptane)

TABLE 11

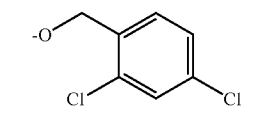

| Example | n | R³ᵃ | LC-MS |
|---|---|---|---|
| 385 | 3 | 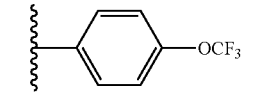 | 515.2 (M + 1) |
| 386 | 1 | 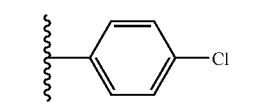 | 498.2 (M + 1) |
| 387 | 1 | 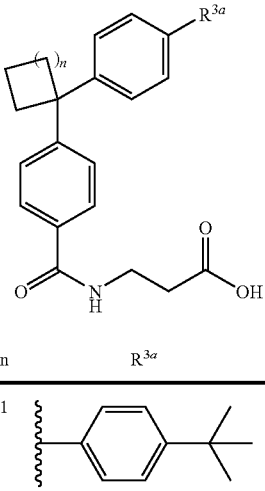 | 482.1 (M + 1) |
| 388 | 1 | 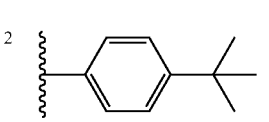 | 432.1 (M + 1) |

TABLE 11-continued

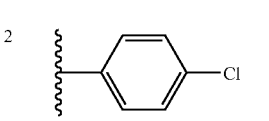

| Example | n | R³ᵃ | LC-MS |
|---|---|---|---|
| 389 | 1 | 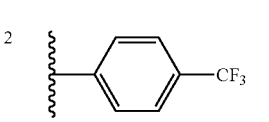 | 454.2 (M + 1) |
| 390 | 2 | 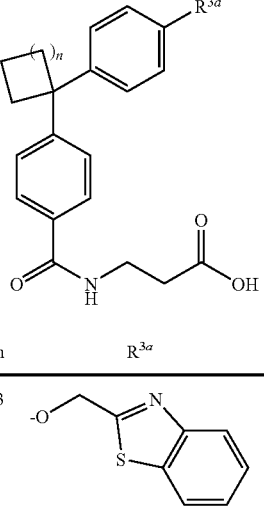 | 470.3 (M + 1) |
| 391 | 2 | 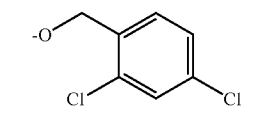 | 448.2 (M + 1) |
| 392 | 2 | 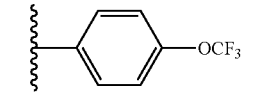 | 482.3 (M + 1) |

TABLE 12

[Structure: indane-spiro compound with (R³ᵃ) substituted phenyl and a phenyl-C(O)NH-CH₂CH₂-C(O)OH group]

| Example | n | R | LC-MS |
|---|---|---|---|
| 393 | 2 | 4-tert-butylphenyl | Neg. ion 530.2 (M − 1) |
| 394 | 2 | 4-OCF₃-phenyl | Neg. ion 558.2 (M − 1) |
| 395 | 2 | 4-Cl-phenyl | Neg. ion 508.1 (M − 1) |
| 396 | 1 | 4-tert-butylphenyl | 518.2 (M + 1) |
| 397 | 1 | 4-Cl-phenyl | 496.3 (M + 1) |

BIOLOGICAL ASSAYS

The ability of the compounds of the present invention to inhibit the binding of glucagon and their utility in treating or preventing type 2 diabetes mellitus and the related conditions can be demonstrated by the following in vitro assays.

Glucagon Receptor Binding Assay

A stable CHO (Chinese hamster ovary) cell line expressing cloned human glucagon receptor was maintained as described (Chicchi et al. *J Biol Chem* 272, 7765-9(1997); Cascieri et al. *J Biol Chem* 274, 8694-7(1999)). To determine antagonistic binding affinity of compounds 0.002 mg of cell membranes from these cells were incubated with $^{125}$I-Glucagon (New England Nuclear, MA) in a buffer containing 50 mM Tris-HCl (pH 7.5), 5 mM MgCl, 2 mM EDTA, 12% Glycerol, and 0.200 mg WGA coated PVT SPA beads (Amersham), +/−compounds or 0.001 MM unlabeled glucagon. After 4-12 hours incubation at room temperature, the radioactivity bound to the cell membranes was determined in a radioactive emission detection counter (Wallac-Microbeta). Data was analyzed using the software program Prism from GraphPad. The IC$_{50}$ values were calculated using non-linear regression analysis assuming single site competition. IC$_{50}$ values for the compounds of the invention are generally in the range of as low as about 1 nM to as high as about 500 nM, and thus have utility as glucagon antagonists.

Inhibition of Glucagon-Stimulated Intracellular cAMP Formation

Exponentially growing CHO cells expressing human glucagon receptor were harvested with the aid of enzyme-free dissociation media (Specialty Media), pelleted at low speed, and re-suspended in the Cell Stimulation Buffer included in the Flash Plate cAMP kit (New England Nuclear, SMP0004A). The adenylate cyclase assay was setup as per manufacturer instructions. Briefly, compounds were diluted from stocks in DMSO and added to cells at a final DMSO concentration of 5%. Cells prepared as above were preincubated in flash plates coated with anti-cAMP antibodies (NEN) in presence of compounds or DMSO controls for 30 minutes, and then stimulated with glucagon (250 pM) for an additional 30 minutes. The cell stimulation was stopped by addition of equal amount of a detection buffer containing lysis buffer as well as $^{125}$I-labeled cAMP tracer (NEN). After 3 hours of incubation at room temperature the bound radioactivity was determined in a liquid scintillation counter (TopCount-Packard Instruments). Basal activity (100% inhibition) was determined using the DMSO control while 0% inhibition was defined at the amount of pmol cAMP produced by 250 pM glucagon.

Certain embodiments of the invention has been described in detail; however, numerous other embodiments are contemplated as falling within the invention. Thus, the claims are not limited to the specific embodiments described herein. All patents, patent applications and publications that are cited herein are hereby incorporated by reference in their entirety.

What is claimed is:

1. A a compound represented by formula I:

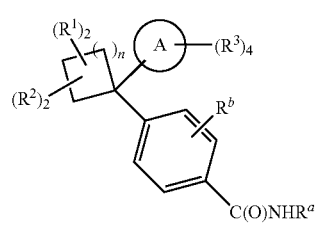

or a pharmaceutically acceptable salt thereof, wherein:

Ring A represents a 6-10 membered Aryl group or a 5-10 membered heteroaryl or partially aromatic heterocyclic group containing 1-4 heteroatoms, 0-4 of which are N atoms, and 0-1 of which are O or S atoms;

two R¹ and two R² groups are present and represent hydrogen, or one or two R¹ and R² groups are selected from (a), (b) and (c) below:

(a) halo, OH, CO₂R⁴, SO$_p$R⁵, CN, NO₂ C(O)NR⁶R⁷ or NR⁶R⁷;

(b) C$_{1-10}$alkyl, C(O)C$_{1-10}$alkyl, OC$_{1-6}$alkyl, C$_{2-6}$alkenyl, the alkyl portions being optionally substituted with: (1) 1-5 halo groups, up to perhalo, and 1-2 OH groups;

(c) a 6-10 membered Aryl, O-Aryl or S-Aryl group, or a 5-10 membered HAR, O-HAR or S-HAR group containing 0-4 nitrogen and 0-1 O or S atoms, said group being optionally substituted with 1-3 groups selected from (a) and (b) above, or two R² groups can be taken together in combination and represent a methylene or ethylene bridge forming a carbocyclic ring containing 5 or 6 atoms, or a fused phenyl ring optionally substituted with 1-3 halo groups and 1-2 CN, SO$_p$R⁵, C$_{1-3}$alkyl, C$_{1-3}$ alkoxy, haloC$_{1-3}$ alkyl, haloC$_{1-3}$ alkoxy groups, and the R¹ groups represent H or are selected from (a) through (c) above;

four R³ groups are present as follows:
1) 0-1 R³ group is selected from the group consisting of: Aryl, HAR, —(CH₂)₁₋₄Aryl, —(CH₂)₁₋₄HAR, —X-Aryl, —X-HAR, —X—C₁₋₄Alkyl-Aryl and —X—C₁₋₄Alkyl-HAR; wherein X represents O, S, S(O) or S(O)₂;

said Aryl and HAR groups and portions of the groups above being optionally substituted with 1-4 halo atoms, and 1-2 members selected from: OH, CN, C₁₋₆alkyl, OC₁₋₆allyl, haloC₁₋₆allyl, OC₁₋₆haloalkyl, NO₂, SO$_p$R⁵, C₂₋₆alkenyl, OC₂₋₆alkenyl, NR⁶R⁷ and HAR;

2) 0-3 R³ groups are selected from: OH, CN, oxo, NO₂, SO$_p$R⁵, NR⁶R⁷, C₁₋₁₀alkyl, haloC₁₋₁₀ alkyl, OC₁₋₁₀alkyl, OC₁₋₁₀haloalkyl, C₂₋₁₀alkenyl, OC₂₋₆alkenyl and haloC₂₋₄alkenyl, and 3) the remaining R³ groups are H or halo atoms;

R⁴ is H or C₁₋₆alkyl, and

R⁵ represents a member selected from the group consisting of: C₁₋₁₀alkyl, Aryl or Ar—C₁₋₄-alkyl;

R⁶ and R⁷ each independently represent H or C₁₋₆alkyl;

n represents an integer of from 0-5;

p is 0, 1 or 2;

R$^a$ represents CH₂CH₂CO₂R⁴, CH₂CH(OH)CO₂R⁴ or 5-tetrazolyl; and

R$^b$ is H or is selected from the group consisting of: halo, CN, NO₂, OH, C₁₋₃alkyl, OC₁₋₃alkyl, haloC₁₋₃alkyl and haloC₁₋₃alkoxy.

2. A compound in accordance with claim 1, or a pharmaceutically acceptable salt thereof, wherein Ring A represents an Aryl group selected from phenyl, naphthyl and tetrahydronaphthyl, a HAR group which is a 6-10 membered aromatic heteroaryl or partially aromatic heterocyclyl containing 1-2 heteroatoms, 0-1 of which is O and 0-2 of which are N atoms.

3. A compound in accordance with claim 2, or a pharmaceutically acceptable salt thereof, wherein Ring A represents a member selected from the group consisting of:

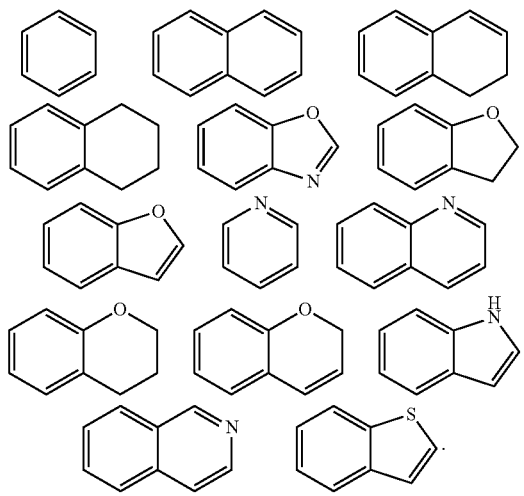

4. A compound in accordance with claim 3, or a pharmaceutically acceptable salt thereof, wherein Ring A represents a member selected from the group consisting of:

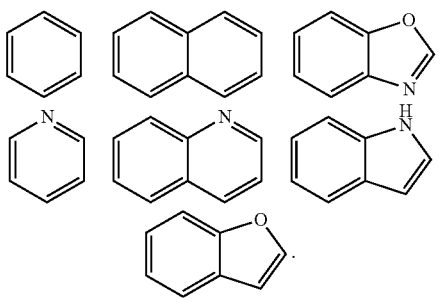

5. A compound in accordance with claim 1, or a pharmaceutically acceptable salt thereof, wherein n represents an integer selected from 1, 2 and 3.

6. A compound in accordance with claim 5 or a pharmaceutically acceptable salt thereof, wherein n represents an integer selected from 1 and 2.

7. A compound in accordance with claim 6, or a pharmaceutically acceptable salt thereof, wherein n represents 2.

8. A compound in accordance with claim 1, or a pharmaceutically acceptable salt thereof, wherein the R¹ and R² groups represent hydrogen or 1-2 of the R¹ and R² groups are independently selected from the group consisting of: halo; OH; C₁₋₆alkyl optionally substituted with 1-3 halo groups; CN; NR⁶R⁷; SO$_p$R⁵; C₂₋₄-alkenyl, and a 6-10 membered Aryl group, or the R² groups are taken in combination and represent a —CH₂— or —CH₂CH₂— group, or a fused phenyl ring, unsubstituted or substituted with 1-3 groups, up to 3 of which are halo groups, and up to 2 of which are C₁₋₃alkyl, haloC₁₋₃alkyl, C₁₋₃alkoxy or haloC₁₋₃alkoxy groups.

9. A compound in accordance with claim 8 or a pharmaceutically acceptable salt thereof, wherein the R¹ groups represent hydrogen halo; C₁₋₃alkyl optionally substituted with 1-3 halo groups; CN or NR⁶R⁷; and the R² groups represent H, or are taken in combination and represent a —CH₂— or a fused phenyl ring, unsubstituted or substituted with 1-3 groups, up to 3 of which are halo groups, and up to 2 of which are C₁₋₃alkyl, haloC₁₋₃alkyl, C₁₋₃alkoxy or haloC₁₋₃alkoxy groups.

10. A compound in accordance with claim 9 or a pharmaceutically acceptable salt thereof, wherein the R¹ groups represent hydrogen, halo; CH₃ or CF₃, and the R² groups represent H, or are taken in combination and represent a —CH₂— or a fused phenyl ring.

11. A compound in accordance with claim 1, or a pharmaceutically acceptable salt thereof, wherein R$^a$ is selected from

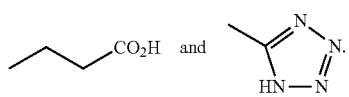

12. A compound in accordance with claim 11, or a pharmaceutically acceptable salt thereof, wherein R$^a$ represents

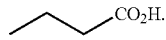

13. A compound in accordance with claim 1, or a pharmaceutically acceptable salt thereof, wherein R$^b$ represents H.

14. A compound in accordance with claim 1, or a pharmaceutically acceptable salt thereof, wherein each R³ is selected as follows:

1) 0-1 R³ group is selected from the group consisting of: Aryl, HAR, —CH₂-Aryl, —CH₂-HAR, —O-Aryl, —O-HAR, —O—CH₂-Aryl and —O—CH₂-HAR;
said Aryl and HAR groups and portions of the groups above being optionally substituted with 1-2 halo atoms, and 1-2 members selected from: CN, $C_{1-6}$alkyl, $OC_{1-6}$allyl, haloC$_{1-3}$alkyl, $OC_{1-3}$haloalkyl, NO₂, $S(O)_pR^5$, $C_{2-6}$alkenyl, NH₂, NMe₂ and HAR;
2) 0-3 R³ groups are selected from: CN, oxo, NO₂, $S(O)_pC_{1-8}$allyl, NH₂, NMe₂, $C_{1-7}$alkyl, haloC$_{1-3}$alkyl, $OC_{1-7}$alkyl, $OC_{1-3}$haloalkyl and $C_{2-6}$alkenyl, and
3) the remaining R³ groups are H or halo atoms.

15. A compound in accordance with claim 14, or a pharmaceutically acceptable salt thereof, wherein each R³ is selected as follows:
1) 0-1 R³ group is selected from the group consisting of: Aryl, HAR, —CH₂-Aryl, —CH₂-HAR, —O-Aryl, —O-HAR, —O—CH₂-Aryl and —O—CH₂-HAR;
said Aryl and HAR groups and portions of the groups above being optionally substituted with 1-2 halo atoms and 1-2 members selected from: CN, $C_{1-4}$alkyl, $OC_{1-6}$alkyl, $S(O)_pC_{1-6}$alkyl, halomethyl, halomethoxy, NO₂, NMe₂ and pyrazolyl;
2) 0-1 R³ group is selected from: CN, oxo, NO₂, SO₂CH₃, NMe₂, $C_{1-7}$alkyl, haloC$_{1-3}$alkyl, $OC_{1-7}$alkyl, $OC_{1-3}$haloalkyl and $C_{2-6}$alkenyl, and
3) the remaining R³ groups are H or halo atoms.

16. A compound in accordance with claim 15 or a pharmaceutically acceptable salt thereof, wherein each R³ is selected as follows:
1) 0-1 R³ group represents: Aryl, wherein Aryl is selected from phenyl, naphthyl and tetrahydronaphthyl; HAR selected from pyridyl, quinolinyl, pyrimidinyl, isoxazolyl, benzoxazolyl, benzopyrazolyl, benzooxadiazolyl, indazolyl, benzofuranyl, tetrahydroquinolinyl, benzothiophene, benzothiazole and benzoimidazolyl; —CH₂-Aryl selected from benzyl; —O-Aryl selected from phenyloxy; —O-HAR selected from pyridyloxy, benzothiazoloxy and quinolinyloxy; —O—CH₂-Aryl selected from benzyloxy or —O—CH₂-HAR selected from: pyridylmethoxy, furanylmethoxy, benzothiazolmethoxy and quinolinylmethoxy;
said Aryl and HAR groups and portions of the groups above being optionally substituted with 1-2 halo atoms and 1 member selected from: CN, $C_{1-4}$alkyl, methoxy, trifluoromethyl, trifluoromethoxy, NO₂, and NMe₂;
2) 0-1 R³ group is selected from: $C_{1-7}$alkyl, haloC$_{1-3}$alkyl, $OC_{1-7}$alkyl and $OC_{1-3}$haloalkyl, and
3) the remaining R³ groups are H or halo atoms.

17. A compound in accordance with claim 1, or a pharmaceutically acceptable salt thereof, wherein:
Ring A represents an Aryl group selected from phenyl, naphthyl and tetrahydronaphthyl, a HAR group which is a 6-10 membered aromatic heteroaryl or partially aromatic heterocyclyl containing 1-2 heteroatoms, 0-1 of which is O and 0-2 of which are N atoms;
n represents an integer selected from 1, 2 and 3;
the R¹ and R² groups represent hydrogen or 1-2 of the R¹ and R² groups are independently selected from the group consisting of: halo; OH; $C_{1-6}$alkyl optionally substituted with 1-3 halo groups; CN; NR⁶R⁷; $SO_pR^5$; $C_{2-4}$alkenyl, and a 6-10 membered Aryl group, or the R² groups are taken in combination and represent a —CH₂— or —CH₂CH₂— group, or a fused phenyl ring, unsubstituted or substituted with 1-3 groups, up to 3 of which are halo groups, and up to 2 of which are $C_{1-3}$alkyl, haloC$_{1-3}$alkyl, $C_{1-3}$alkoxy or haloC$_{1-3}$alkoxy groups;
Rᵃ is selected from

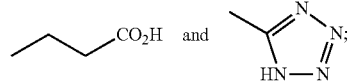

Rᵇ represents H, and
each R³ is selected as follows:
1) 0-1 R³ group is selected from the group consisting of: Aryl, HAR, —CH₂-Aryl, —CH₂-HAR, —O-Aryl, —O-HAR, —O—CH₂-Aryl and —O—CH₂-HAR;
said Aryl and HAR groups and portions of the groups above being optionally substituted with 1-2 halo atoms, and 1-2 members selected from: CN, $C_{1-6}$alkyl, $OC_{1-6}$alkyl, haloC$_{1-3}$alkyl, $OC_{1-3}$haloalkyl, NO₂, $SO_pR^5$, $C_{2-6}$alkenyl, NH₂, NMe₂ and HAR;
2) 0-3 R³ groups are selected from: CN, oxo, NO₂, $S(O)_pC_{1-8}$alkyl, NH₂, NMe₂, $C_{1-7}$alkyl, haloC$_{1-3}$alkyl, $OC_{1-7}$alkyl, $OC_{1-3}$haloalkyl and $C_{2-6}$alkenyl, and
3) the remaining R³ groups are H or halo atoms.

18. A pharmaceutical composition comprising a compound in accordance with claim 1, or a pharmaceutically acceptable salt thereof, in combination with a pharmaceutically acceptable carrier.

* * * * *